US012697048B2

(12) United States Patent
Miyake et al.

(10) Patent No.: US 12,697,048 B2
(45) Date of Patent: Aug. 4, 2026

(54) SENSOR SYSTEM, READER, AND SENSOR

(71) Applicant: WASEDA UNIVERSITY, Tokyo (JP)

(72) Inventors: Takeo Miyake, Tokyo (JP); Taiki Takamatsu, Tokyo (JP)

(73) Assignee: WASEDA UNIVERSITY, Tokyo (JP)

( * ) Notice: Subject to any disclaimer, the term of this patent is extended or adjusted under 35 U.S.C. 154(b) by 290 days.

(21) Appl. No.: 18/551,595

(22) PCT Filed: Mar. 22, 2022

(86) PCT No.: PCT/JP2022/013031
§ 371 (c)(1),
(2) Date: Sep. 20, 2023

(87) PCT Pub. No.: WO2022/202773
PCT Pub. Date: Sep. 29, 2022

(65) Prior Publication Data

US 2024/0138731 A1 May 2, 2024

(30) Foreign Application Priority Data

Mar. 22, 2021 (JP) ................................. 2021-047975

(51) Int. Cl.
*A61B 5/145* (2006.01)
*A61B 5/00* (2006.01)
*A61B 5/1473* (2006.01)

(52) U.S. Cl.
CPC ...... *A61B 5/14503* (2013.01); *A61B 5/14532* (2013.01); *A61B 5/6821* (2013.01); *A61B 5/1473* (2013.01)

(58) Field of Classification Search
CPC ............ A61B 5/14503; A61B 5/14532; A61B 5/6821; A61B 5/1473; A61B 5/14507; A61B 5/14546
See application file for complete search history.

(56) References Cited

U.S. PATENT DOCUMENTS 5,703,576 A 12/1997 Spillman, Jr. et al.
2008/0012579 A1 1/2008 Kuhns et al.
(Continued)

FOREIGN PATENT DOCUMENTS

WO 2007/136966 A1 11/2007

OTHER PUBLICATIONS

Extended European Search Report issued in EP 22 77 5557.6-1113 by the European Patent Office on Feb. 10, 2025, which is related to U.S. Appl. No. 18/551,595.
(Continued)

*Primary Examiner* — Catherine M Voorhees
(74) *Attorney, Agent, or Firm* — Studebaker Brackett PLLC

(57) ABSTRACT

A sensor system includes a reader side resonant circuit (10) and a sensor side resonant circuit (20). The reader side resonant circuit (10) is an LCR parallel resonant circuit and a gain circuit. The sensor side resonant circuit (20) is an LCR parallel resonant circuit and a loss circuit having, as a resistance portion, a sensor element whose resistance value changes according to an object to be sensed. The reader side resonant circuit (10) and the sensor side resonant circuit (20) are wirelessly connected to each other through magnetic field resonant coupling to constitute a gain-loss coupling circuit, and the reader side resonant circuit (10) and the sensor side resonant circuit (20) are formed such that the gain-loss coupling circuit has parity-time symmetry.

29 Claims, 35 Drawing Sheets

(56) References Cited

U.S. PATENT DOCUMENTS

| | | | |
|---|---|---|---|
| 2010/0249548 A1* | 9/2010 | Muller | A61B 5/14532 |
| | | | 600/318 |
| 2015/0057516 A1 | 2/2015 | Mujeeb-U-Rahman et al. | |
| 2015/0282743 A1 | 10/2015 | Etzkorn et al. | |
| 2020/0012008 A1* | 1/2020 | Chen | G01L 9/14 |
| 2020/0257946 A1* | 8/2020 | Kananian | G06K 19/00 |

OTHER PUBLICATIONS

International Search Report issued in PCT/JP2022/013031; mailed May 17, 2022.

Pai-Yen Chen at al. "Generalized parity-time symmetry condition for enhanced sensor telemetry", Nature Electronics, vol. 1, pp. 297-304.; May 24, 2018.

Zhenya Dong et al. "Sensitive readout of implantable microsensors using a wireless system locked to an exceptional point", Nature Electronics, vol. 2, pp. 335-342.; Aug. 15, 2019.

Ming Xing Chu et al. "Soft contact lens biosensor for in situ monitoring of tear glucose as non-invasive blood sugar assessment", Talanta, vol. 83, pp. 960-965.; Nov. 4, 2010.

Huanfen Yao et al. "A contact lens with embedded sensor for monitoring tear glucose level", Biosensors and Bioelectronics, vol. 26, (7), pp. 3290-3296.; Dec. 31, 2010.

Do Hee Keum et al. "Wireless smart contact lens for diabetic diagnosis and therapy", Sci. Adv., vol. 6 (17): eaba3252.; Apr. 24, 2020.

Joohee Kim et al. "Wearable smart sensor systems integrated on soft contact lenses for wireless ocular diagnostics", Nature Communications, vol. 8:14997.; Apr. 27, 2017.

Shiqi Guo et al. "Integrated contact lens sensor system based on multifunctional ultrathin MoS2 transistors", Matter, vol. 4, pp. 969-985.; Mar. 3, 2021.

Jihun Park et al. "Soft, smart contact lenses with integrations of wireless circuits, glucose sensors, and displays", Sci. Adv., vol. 4, eaap9841.; Jan. 24, 2018.

Jennifer D. Lane et al. "Tear Glucose Dynamics in Diabetes Mellitus", Current Eye Research, vol. 31 (11), pp. 895-901.; Jul. 2, 2009.

Carl M. Bender et al. "Real Spectra in Non-Hermitian Hamiltonians Having PT Symmetry", Phys. Rev. Lett. 80 (24), 5243.; Jun. 15, 1998.

A. Guo et al. "Observation of PT-Symmetry Breaking in Complex Optical Potentials", Phys. Rev. Lett., vol. 103 (9), 093902.; Aug. 28, 2009.

Xu-Lin Zhang et al. "Dynamically encircling an exceptional point in anti-PT-symmetric systems: asymmetric mode switching for symmetry-broken states", Light: Science & Applications, vol. 8:88.; Oct. 2, 2019.

H. Jing et al. "Optomechanically-induced transparency in parity-time-symmetric microresonators", Scientific Reports, vol. 5, 9663.; Jun. 12, 2015.

Bo Peng et al. "Parity-time-symmetric whispering-gallery microcavities", Nature Physics, vol. 10, pp. 394-398.; Apr. 6, 2014.

"Jing Zhang et al. "A phonon laser operating at an exceptional point", Nature Photonics, vol. 12, pp. 479-484."; Jul. 9, 2018.

Hossein Hodaei et al. "Enhanced sensitivity at higher-order exceptional points", Nature, vol. 548, pp. 187-191.; Aug. 10, 2017.

Henri Benisty et al. "Implementation of PT symmetric devices using plasmonics: principle and applications", Optics Express, vol. 19 (19), pp. 18004-18019.; Aug. 30, 2011.

E. Persson et al. "Observation of resonance trapping in an open microwave cavity", Phys. Rev. Lett., vol. 85 (12), 2478.; Sep. 18, 2000.

C. Dembowski et al. "Experimental Observation of the Topological Structure of Exceptional Points", Phys. Rev. Lett., vol. 86 (5), 787.; Jan. 29, 2001.

Liang Feng et al. "Single-mode laser by parity-time symmetry breaking", Science, vol. 346 (6212), pp. 972-975.; Nov. 21, 2014.

M. Brandstetter et al. "Reversing the pump dependence of a laser at an exceptional point", Nature Communications, vol. 5, 4034.; Jun. 13, 2014.

Weilin Liu et al. "An integrated parity-time symmetric wavelength-tunable single-mode microring laser", Nature Communications, vol. 8, 15389.; May 12, 2017.

Holger Cartarius et al. "Exceptional Points in Atomic Spectra", Phys. Rev. Lett. vol. 99, 173003.; Oct. 26, 2007.

Carl M. Bender et al. "Observation of PT phase transition in a simple mechanicalsystem", American Journal of Physics, vol. 81 (3), 173-179.; Jun. 22, 2012.

Romain Fleury et al. "An invisible acoustic sensor based on parity-time symmetry", Nature Communications, vol. 6, 5905.; Jan. 6, 2015.

Yuzhen Yang et al. "Experimental Demonstration of an Acoustic Asymmetric Diffraction Grating Based on Passive Parity-Time-Symmetric Medium", Phys. Rev. Applied, vol. 12, 034040.; Sep. 19, 2019.

Joseph Schindler et al. "Experimental study of active LRC circuits with PT symmetries", Phys. Rev. A, vol. 84 (4), 040101(R).; Oct. 13, 2011.

Yun Jing Zhang et al ."Noninvasive Glucose Sensor Based on Parity-Time Symmetry", Phys. Rev. Applied, vol. 11 (4), 044049.; Apr. 16, 2019.

Seung Ho Lee et al. "Noninvasive Self-diagnostic Device for Tear Collection and Glucose Measuremnt", Scientific Reports, vol. 9, 4747.; Mar. 18, 2019.

Wei Huang et al. "Analysis and Optimization of Wireless Power Transfer Efficiency Considering the Tilt Angle of a Coil", Journal of Electromagnetic Engineering and Science, vol. 18 (1), pp. 13-19.; Jan. 31, 2018.

Daniel A. del Portal, MD et al. "Emergency Department Lactate Is Associated with Mortality in Older Adults Admitted With and Without Infections", Academic Emergency Medicine, vol. 17 (3), pp. 260-268.; Mar. 1, 2010.

Masashi Hotta et al. "Effect of Water and/or Dielectric Materials for Resonant Type Wireless Power Transfer System", The Japanese Journal of the Institute of Industrial Applications Engineers, vol. 2 (2), pp. 23-31.; Jun. 23, 2014.

Li Changsheng et al. "Transfer Characteristics of the Nonlinear Parity-Time-Symmetric Wireless Power Transfer System at Detuning", Energies, vol. 13 (19) , pp. 1-3.; Ot. 5, 2020.

Hamidreza Kazemi et al. "Ultra-Sensitive Radio Frequency Biosensor at an Exceptional Point of Degeneracy induced by Time Modulation". [online] [retrieval date Apr. 27, 2022], internet: <https://doi.org/10.48550/arXiv.1909.03344>, p. 1, fig. 1; Jul. 19, 2020.

Office Action issued in CN 202280021763.7; mailed by the State Intellectual Property Office of the People's Republic of China on Jan. 21, 2026.

Communication pursuant to Article 94(3) EPC issued in EP 22 775 557.6-1113 by the European Patent Office on Mar. 31, 2026.

* cited by examiner ( a ) LOSS-LOSS COUPLING CIRCUIT ( b ) GAIN-LOSS COUPLING CIRCUIT (a)

(b)

(c)

(a)

(b)

(c)

(a)

(b)

Reading resonator          Sensing resonator (a)

Sweep (b)

FIG. 40

SENSOR SYSTEM, READER, AND SENSOR

TECHNICAL FIELD

The present invention relates to a sensor system, a reader, and a sensor having a reader side resonant circuit and a sensor side resonant circuit wirelessly connected to each other through magnetic field resonant coupling.

BACKGROUND ART

A sensor system is known that measures a very small amount of glucose (approximately 0 to 1.0 (mM)) contained in tears by wirelessly connecting a reader side resonant circuit connected to a measurement device and a sensor side resonant circuit formed on a contact lens, and that attempts to estimate a change in blood glucose level from the value (for example, Non-Patent Document 5).

In Non-Patent Document 5, a sensor side resonant circuit is formed on the contact lens, and a resistance portion of the resonant circuit is a sensor element (glucose sensing element). The reader side resonant circuit and the sensor side resonant circuit are wirelessly connected to each other through magnetic field resonant coupling, and thus a signal corresponding to the glucose concentration generated in the sensor side resonant circuit can be measured through the reader side resonant circuit.

In the sensor system of Non-Patent Document 5, both the reader side resonant circuit and the sensor side resonant circuit are loss circuits. A circuit in which two such loss circuits are coupled is called a loss-loss coupling circuit.

A "loss circuit" is a circuit configured by inductance: L (proportional constant representing energy of magnetic field stored in coil), capacitance: C (proportional constant representing energy of charge stored in capacitor), and resistance: R (constant representing energy loss), and is a circuit that loses energy at a specific resonance frequency.

On the other hand, there is a "gain circuit" as a circuit having a property opposite to that of the "loss circuit".

A "gain circuit" is a circuit configured by inductance: L, capacitance: C, and a negative resistance: −R (constant representing energy gain), and is a circuit that supplies energy at a specific resonance frequency.

Since a loss-loss coupling circuit can be configured by a general dissipative resonant circuit and has the advantage of being simple to implement, the sensor system of Non-Patent Document 5 employs the loss-loss coupling circuit. However, since the loss-loss coupling circuit detects a value obtained by superimposing a resonant load on the reading side and a resonant load on the sensor side, it cannot sufficiently detect weak signals. The amount of glucose in tears is very small, and the electrical signal obtained by the sensor element is also very weak. Accordingly, it is difficult to actually provide a desirable sensor system product with the loss-loss coupling circuit as in Non-Patent Document 5.

On the other hand, in the sensor system described in Patent Document 1, the reader side resonant circuit is a gain circuit, the sensor side resonant circuit is a loss circuit, and these gain circuit and loss circuit are wirelessly connected through magnetic field resonant coupling to constitute a gain-loss coupling circuit. The gain-loss coupling circuit has a characteristic that the energy dissipated by a resonant load on the loss side is compensated for by an oscillation circuit on the gain side, and as a result, has an advantage of constructing an ideal lossless LC circuit (conservative system) near the resonance frequency.

The sensor system of Patent Document 1 is for sensing changes in intraocular pressure, and an external reader side resonant circuit and a sensor side resonant circuit formed on a contact lens are wirelessly connected. The sensor side resonant circuit is an LCR resonant circuit that includes a sensor element. The sensor element is an element that senses intraocular pressure. When the eyeball expands/contracts in response to changes in intraocular pressure, the sensor element deforms accordingly, and the capacitance of the sensor element changes according to the deformation. That is, the sensor element is a kind of variable capacitor. A change in the capacitance of the sensor element also appears in the reader side resonant circuit, and the change in intraocular pressure is detected by measuring the change using a vector network analyzer (VNA) or the like.

In the sensor system of Patent Document 1, the reader side resonant circuit is an LCR series resonant circuit in which a coil, a capacitor, and a resistor are connected in series, and the sensor side resonant circuit is also an LCR series resonant circuit in which a coil, a sensor element (variable capacitor), and a resistor are connected in series. The reader side resonant circuit and the sensor side resonant circuit are wirelessly connected to each other through magnetic field resonant coupling between the respective coils.

In the gain-loss coupling circuit in the sensor system of Patent Document 1, a capacitance value, an inductance value, and a resistance value in the two resonant circuits are further determined such that the parity-time symmetry of the gain circuit and the loss circuit are maintained. According to such a gain-loss coupling circuit having parity-time symmetry, it is possible to sharpen the resonance frequency, and therefore highly sensitive wireless measurement can be achieved.

RELATED DOCUMENT

Patent Document

[Patent Document 1] U.S. Unexamined Patent Publication No. 2020/012008 A1

Non-Patent Document

[Non-Patent Document 1] "Generalized parity-time symmetry condition for enhanced sensor telemetry", NATURE ELECTRONICS, 1, 297-304, (2018)

[Non-Patent Document 2] "Sensitive readout of implantable microsensors using a wireless system locked to an exceptional point", NATURE ELECTRONICS, 2, 335-342, (2019)

[Non-Patent Document 3] "Soft contact lens biosensor for in situ monitoring of tear glucose as non-invasive blood sugar assessment", Talanta, 83, 960-965, (2011)

[Non-Patent Document 4] "A contact lens with embedded sensor for monitoring tear glucose level", Biosens Bioelectron, 26, 7, 3290, (2011)

[Non-Patent Document 5] "Wireless smart contact lens for diabetic diagnosis and therapy", Sci. Adv., 6: eabb2891, (2020)

[Non-Patent Document 6] "Wearable smart sensor systems integrated on soft contact lenses for wireless ocular diagnostics", Nature Communications, 8:14997, (2017)

[Non-Patent Document 7] "Integrated contact lens sensor system based on multifunctional ultrathin MoS2 transistors", Matter, 4, 1-17, (2020)

[Non-Patent Document 8] "Soft, smart contact lenses with integrations of wireless circuits, glucose sensors, and displays", Sci. Adv., 4, eaap9841, (2018)

[Non-Patent Document 9] "Tear Glucose Dynamics in Diabetes Mellitus", Current Eye Research, 31, 895-901, (2006)

[Non-Patent Document 10] "Real Spectra in Non-Hermitian Hamiltonians Having PT Symmetry", Phys. Rev. Lett. 80, 5243, (1998)

[Non-Patent Document 11] "Observation of PT-Symmetry Breaking in Complex Optical Potentials", Phys. Rev. Lett., 103, 093902, (2009)

[Non-Patent Document 12] "Dynamically encircling an exceptional point in anti-PT-symmetric systems: asymmetric mode switching for symmetry-broken states", Light: Science & Applications, 8:88, (2019)

[Non-Patent Document 13] "Optomechanically-induced transparency in parity-time-symmetric microresonators", Scientific Reports, 5:9663, (2015)

[Non-Patent Document 14] "Parity-time-symmetric whispering-gallery microcavities", Nature Physics, 10, 394-398, (2014)

[Non-Patent Document 15] "A phonon laser operating at an exceptional point", Nature Photonics, 12, 479-484, (2018)

[Non-Patent Document 16] "Enhanced sensitivity at higher-order exceptional points", Nature, 548, 187-191, (2017)

[Non-Patent Document 17] "Implementation of PT symmetric devices using plasmonics: principle and applications", Optics Express, 19, 19, 18004-18019, (2011)

[Non-Patent Document 18] "Observation of resonance trapping in an open microwave cavity", Phys. Rev. Lett., 85, 2478, (2000)

[Non-Patent Document 19] "Experimental Observation of the Topological Structure of Exceptional Points", Phys. Rev. Lett., 86, 787, (2001)

[Non-Patent Document 20] "Single-mode laser by parity-time symmetry breaking", Science, 346, 6212, 972-975, (2014)

[Non-Patent Document 21] "Reversing the pump dependence of a laser at an exceptional point", Nature Communications, 5, 4034, (2014)

[Non-Patent Document 22] "An integrated parity-time symmetric wavelength-tunable single-mode microring", Nature Communications, 8:15389, (2017)

[Non-Patent Document 23] "Exceptional Points in Atomic Spectra", Phys. Rev. Lett. 99, 173003, (2007)

[Non-Patent Document 24] "Observation of PT phase transition in a simple mechanical system", American Journal of Physics, 81, 173, (2013)

[Non-Patent Document 25] "An invisible acoustic sensor based on parity-time symmetry", Nature Communications, 6, 5905, (2015)

[Non-Patent Document 26] "Experimental Demonstration of an Acoustic Asymmetric Diffraction Grating Based on Passive Parity-Time-Symmetric Medium", Phys. Rev. Applied, 12, 034040, (2019)

[Non-Patent Document 27] "Experimental study of active LRC circuits with PT symmetries", Phys. Rev. A 84, 040101(R), (2011)

[Non-Patent Document 28] "Noninvasive Glucose Sensor Based on Parity-Time Symmetry", Phys. Rev. Applied, 11, 044049, (2019)

[Non-Patent Document 29] "Noninvasive Self-diagnostic Device for Tear Collection and Glucose Measurement", Scientific Reports, 9, 4747, (2019)

[Non-Patent Document 30] "Analysis and Optimization of Wireless Power Transfer Efficiency Considering the Tilt

4

Angle of a Coil", Journal of Electromagnetic Engineering and Science 2018, 18, 13, (2018)

[Non-Patent Document 31] Daniel A. del Portal, MD, Frances Shofer, PhD, Mark E. Mikkelsen, MD, MSCE, Philip J. Dorsey, Jr., MD, MPH, David F. Gaieski, MD, Munish Goyal, MD, Marie Synnestvedt, PhD, Mark G. Weiner MD, Jesse M. Pines, MD, MBA, MSCE, "Emergency Department Lactate Is Associated with Mortality in Older Adults Admitted With and Without Infections", Academic Emergency Medicine, Vol. 17, Issue 3, 2010

[Non-Patent Document 32] Masashi Hotta, Akinori Nobu, Takayuki Haruyama, Tohru Yuki, Mitsuo Hano, "Effect of Water and/or Dielectric Materials for Resonant Type Wireless Power Transfer System", The Japanese Journal of the Institute of Industrial Applications Engineers, Vol. 2, No. 2, pp. 23-31, 2014

SUMMARY OF THE INVENTION

Technical Problem

However, it is technically difficult to incorporate a sensor element (hereinafter referred to as a "variable resistance sensor element) that senses an object based on a change in resistance value (especially minute changes in the high resistance value region, that is, minute changes in low current values), such as an enzyme electrode for sensing glucose, into the sensor side resonant circuit (LCR series resonant circuit) of Patent Document 1. The reason for this is that it is difficult to measure the glucose response in the sensor element with the alternating current required for resonance, and in addition, it is difficult to implement a high negative resistance in the gain circuit (LCR series resonant circuit). In addition, although Patent document 1 also describes the concept of a system in which two LCR parallel resonant circuits are magnetic field resonant coupled, there is no description about using a high-resistance variable resistance sensor element as the resistance portion in the sensor side resonant circuit, and no specific circuit that enables signal reception is illustrated.

As described above, a sensor system has not yet been provided in which a variable resistance sensor element that senses not only glucose in tears but also various objects to be sensed is disposed as a resistance portion in a sensor side resonant circuit, and a signal can be received wirelessly with high sensitivity.

An object of the present invention is to solve the above issues and to provide a sensor system, a reader, and a sensor that have a variable resistance sensor element in a sensor side resonant circuit and that can wirelessly receive sensing signals with high sensitivity.

Solution to Problem

According to one aspect of the present invention,
there is provided a sensor system including a reader side resonant circuit and a sensor side resonant circuit,
in which the reader side resonant circuit is an LCR parallel resonant circuit and a gain circuit,
the sensor side resonant circuit is an LCR parallel resonant circuit and a loss circuit having, as a resistance portion, a sensor element whose resistance value changes according to an object to be sensed,
the reader side resonant circuit and the sensor side resonant circuit are wirelessly connected to each other through magnetic field resonant coupling to constitute a gain-loss coupling circuit, and the reader side resonant circuit and the sensor side resonant circuit are formed such that the gain-loss coupling circuit has parity-time symmetry.

According to one aspect of the present invention, there is provided a reader used in a sensor system including a reader side resonant circuit and a sensor side resonant circuit, the reader including the reader side resonant circuit, in which the reader side resonant circuit is an LCR parallel resonant circuit and a gain circuit, the sensor side resonant circuit is an LCR parallel resonant circuit and a loss circuit having, as a resistance portion, a sensor element whose resistance value changes according to an object to be sensed, the reader side resonant circuit and the sensor side resonant circuit are wirelessly connected to each other through magnetic field resonant coupling to constitute a gain-loss coupling circuit, and the reader side resonant circuit and the sensor side resonant circuit are formed such that the gain-loss coupling circuit has parity-time symmetry.

According to one aspect of the present invention, there is provided a sensor used in a sensor system including a reader side resonant circuit and a sensor side resonant circuit, the sensor including the sensor side resonant circuit, in which the reader side resonant circuit is an LCR parallel resonant circuit and a gain circuit, the sensor side resonant circuit is an LCR parallel resonant circuit and a loss circuit having, as a resistance portion, a sensor element whose resistance value changes according to an object to be sensed, the reader side resonant circuit and the sensor side resonant circuit are wirelessly connected to each other through magnetic field resonant coupling to constitute a gain-loss coupling circuit, and the reader side resonant circuit and the sensor side resonant circuit are formed such that the gain-loss coupling circuit has parity-time symmetry.

Advantageous Effects of Invention

In the present invention, the reader side resonant circuit is configured to be a parallel resonant circuit and a gain circuit, the sensor side resonant circuit is configured to be a parallel resonant circuit and a loss circuit, and a variable resistance sensor element is disposed as a resistance portion in the sensor side resonant circuit. The reader side resonant circuit and the sensor side resonant circuit are wirelessly magnetic field resonant coupled to constitute a gain-loss coupling circuit. Further, a reader side resonant circuit (gain circuit) and a sensor side resonant circuit (loss circuit) are formed such that the gain-loss coupling circuit satisfies parity-time symmetry. With the above configuration, it is possible to sharpen the resonance frequency while using the variable resistance sensor element in the sensor side resonant circuit, and the reader side resonant circuit can receive a minute sensing signal generated by the variable resistance sensor element with high sensitivity.

BRIEF DESCRIPTION OF THE DRAWINGS

FIG. 19(a) relates to a loss-loss coupling circuit, and FIG. 19(b) relates to a gain-loss coupling circuit.

FIG. 40 shows measured values of the input impedance real part of a magnetic resonant coupling system having PT symmetry.

DESCRIPTION OF EMBODIMENTS

Hereinafter, the present invention will be described in detail while citing configuration examples of circuits as examples.

Figure 1:
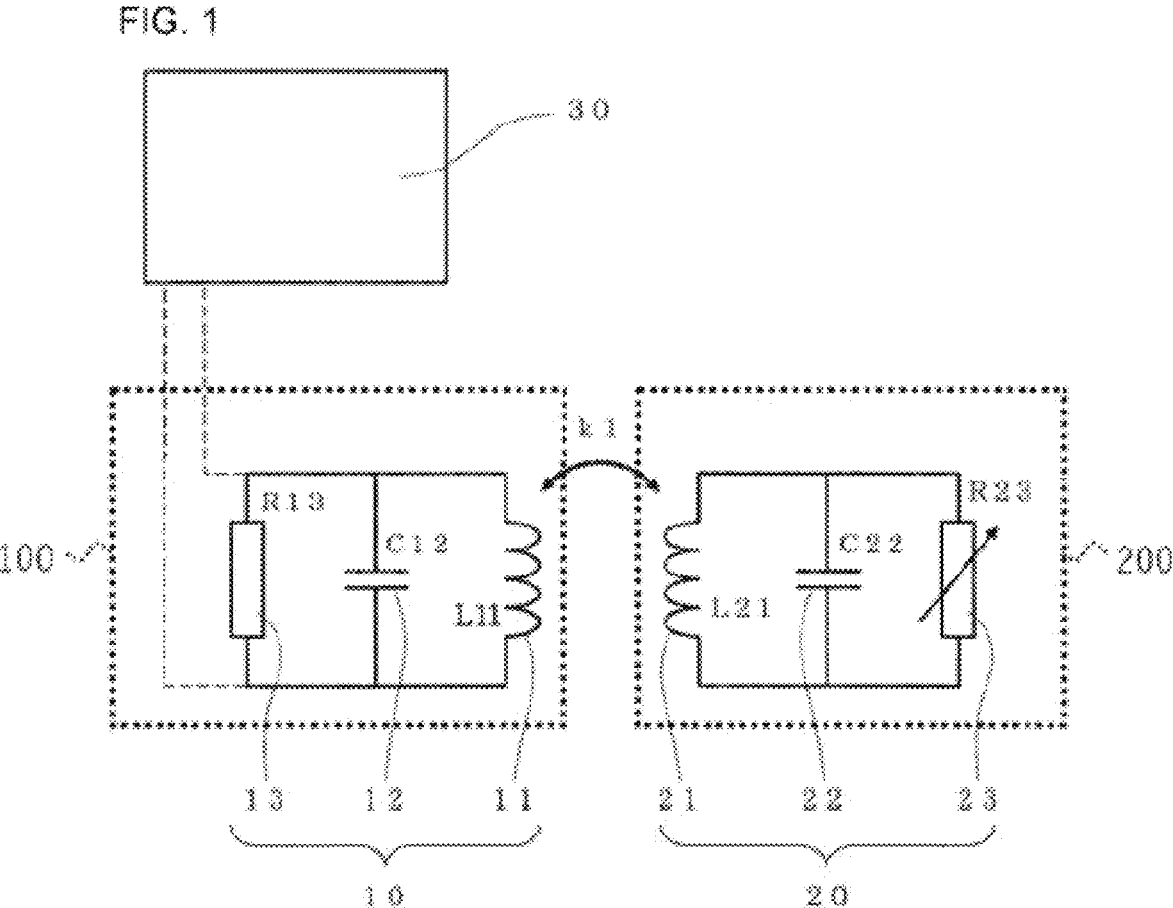
FIG. 1 is a block diagram showing a configuration of a sensor system of the present invention.

A sensor system according to the present invention includes a reader side resonant circuit 10 and a sensor side resonant circuit 20, as shown in an example of the configuration in FIG. 1. In the example shown in FIG. 1, a device 30 is connected to both ends of the resistance portion 13 of the reader side resonant circuit 10 to measure frequency characteristics of transmitted and reflected powers of a connected device under test.

A reader 100 according to the present invention is used as a part of a sensor system having a reader side resonant circuit 10 and a sensor side resonant circuit 20. The reader 100 includes the reader side resonant circuit 10. The reader 100 may be used as a measurement device together with the device 30 (such as a VNA to be described later) that is a high frequency measurement instrument.

A sensor 200 according to the present invention is used as a part of a sensor system having a reader side resonant circuit 10 and a sensor side resonant circuit 20. The sensor 200 includes the sensor side resonant circuit 20. Note that one reader 100 may read a plurality of sensors 200, and one sensor 200 may be read by a plurality of readers 100.

(Reader Side Resonant Circuit)

The reader side resonant circuit 10 is a resonant circuit (that is, an LCR parallel resonant circuit) in which a coil portion 11, a capacitor portion 12, and a resistance portion 13 are connected in parallel.

(Gain Circuit)

The reader side resonant circuit 10 is configured to be a gain circuit. The gain circuit is as described above.

"The LCR parallel resonant circuit is configured to be a gain circuit" specifically refers to a circuit configuration in which energy is supplied at a specific resonance frequency by inserting a negative resistance (–R) into an LC resonant circuit.

(Sensor Side Resonant Circuit)

The sensor side resonant circuit 20 is also a resonant circuit (that is, an LCR parallel resonant circuit) in which a coil portion 21, a capacitor portion 22, and a sensor element (a variable resistance sensor element whose resistance value changes according to an object to be sensed) 23 as a resistance portion are connected in parallel.

The variable resistance sensor element 23 is configured such that its resistance value changes according to a chemical reaction with a substance that is an object to be sensed (for example, glucose in tears) and physical quantities (heat, light, current, voltage, electric field, magnetic field, speed, vibration, force (including pressure), shape change (including strain), and the like) received from the object to be sensed.

The variable resistance sensor element 23 is mechanically, electrically, and (bio) chemically affected by the object to be sensed to change its resistance value.

Therefore, the state of the object to be sensed (concentration value or change, presence or absence, physical quantity value or change, or the like) can be determined from the change in the resistance value of the variable resistance sensor element 23, or the corresponding change in the current value or the voltage value).

For example, the variable resistance sensor element 23 can also be configured such that its resistance value changes according to physical quantities represented by an electroencephalogram, an electrocardiogram, an electromyogram, an electrooculogram, an electroretinogram, an electrodermagram, or the like, and thereby the physical quantities can be detected.

As another example, the variable resistance sensor element 23 can also be configured such that its resistance value changes according to biological-related physical quantities such as blood pressure, heart rate, pulse rate, intraocular pressure, blood oxygen concentration, and sweat, and thereby the biophysical quantities can be detected. Furthermore, the resistance value of the variable resistance sensor element 23 can also be configured to change according to chemical changes and temperature changes due to spoilage of food, maturity and freshness of food, and freezing (refrigerating) temperature of food, and thereby the physical quantities listed above can also be detected.

(Loss Circuit)

The sensor side resonant circuit 20 is configured to be a loss circuit. The loss circuit is as described above.

"The LCR parallel resonant circuit is configured to be a loss circuit" specifically refers to a circuit configuration in which energy is lost at a particular resonance frequency.

(Gain-Loss Coupling Circuit)

The reader side resonant circuit (gain circuit) 10 and the sensor side resonant circuit (loss circuit) 20 are wirelessly connected to each other through magnetic field resonant coupling to constitute a gain-loss coupling circuit. k1 is a coupling coefficient.

Magnetic field resonant coupling (also referred to as magnetic resonant coupling) refers to a state in which the reader side resonant circuit 10 and the sensor side resonant circuit 20 are electrically connected to each other through electromagnetic induction between the coil portion 11 of the reader side resonant circuit 10 and the coil portion 21 of the sensor side resonant circuit 20, and refers to a state in which two resonant circuits whose resonance frequencies are matched in advance are energetically connected using a high-frequency magnetic field as a medium. As for the magnetic field resonant coupling technology itself, conventionally known technology can be referred to.

(Parity-Time Symmetry)

In the present invention, the gain-loss coupling circuit formed by the reader side resonant circuit 10 and the sensor side resonant circuit 20 is configured to have parity-time symmetry (hereinafter also referred to as PT symmetry).

In the present invention, "the gain-loss coupling circuit has PT symmetry" means a state in which the energy dissipated by the resonant load on the loss side is compensated for by the gain side circuit, as a result, a conservative system (Hamiltonian system) is constructed near the resonance frequency, whereby a system configured as a gain-loss coupling circuit behaves like an ideal lossless LC circuit.

In order for the gain-loss coupling circuit to have PT symmetry, the resistance component (R) of the resonant circuit on the loss side (sensor side) and the negative resistance component (−R) of the resonant circuit on the gain side (reader side) need to be designed to have the same absolute value, respectively, and the inductance component (L) and capacitance component (C) need to show equivalent values in terms of circuit.

In the present invention, the values of the coil portion 11, the capacitor portion 12, and the resistance portion 13 of the reader side resonant circuit 10 are selected and the values of the coil portion 21, the capacitor portion 22, and the variable resistance sensor element 23 of the sensor side resonant circuit 20 are selected such that the above conditions are satisfied, thereby imparting PT symmetry to the gain-loss coupling circuit.

That is, the reader side resonant circuit 10 and the sensor side resonant circuit 20 are formed such that the gain-loss coupling circuit has parity-time symmetry.

In the present invention, since a resistance value R23 of the sensor side resonant circuit 20 is the resistance value of the variable resistance sensor element 23, it changes by sensing the object to be sensed. However, since there is a range in the conditions under which the PT symmetry is established, the PT symmetry is maintained as long as the change in the resistance value of the variable resistance sensor element 23 is within a predetermined range.

Therefore, in the present invention, it is possible to detect the existence of the object to be sensed by the variable resistance sensor element 23 under the condition that the PT symmetry is established. In other words, in the present invention, it is preferable to use the variable resistance sensor element 23 whose resistance value changes within a range in which PT symmetry is maintained.

Figure 9:
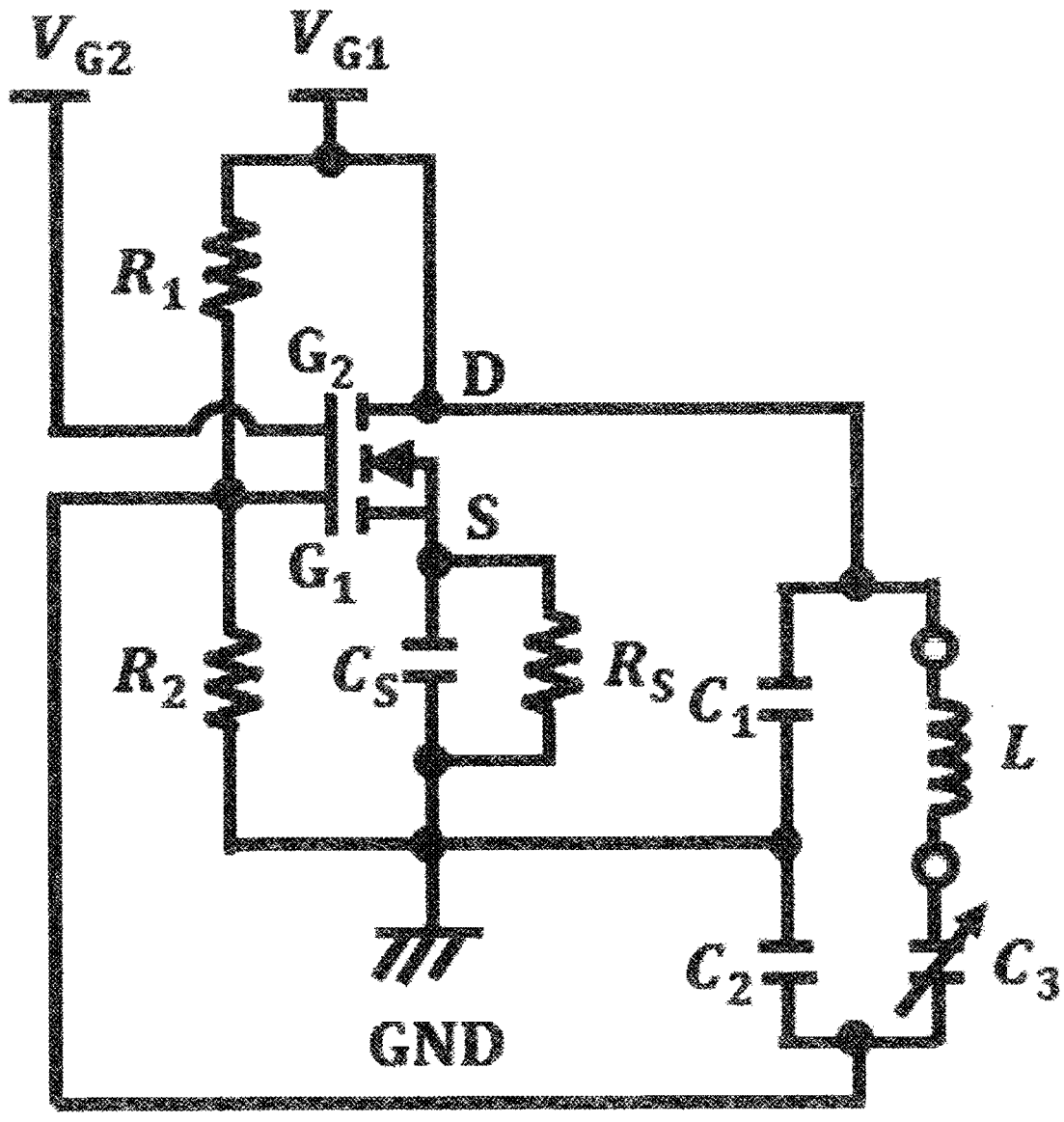
FIG. 9 is a diagram showing a preferred example of a Clapp oscillation circuit manufactured as a reader side resonant circuit (gain circuit).

At least one of the resistance value of the resistance portion 13, the inductance of the coil portion 11, and the capacitance of the capacitor portion 12 in the reader side resonant circuit 10, and the inductance of the coil portion 21 and the capacitance of the capacitor portion 22 in the sensor side resonant circuit 20 is variable, and at least one of the resistance value, the inductance, and the capacitance in the reader side resonant circuit 10 and the inductance and the capacitance in the sensor side resonant circuit 20 is adjusted such that the gain-loss coupling circuit has parity-time symmetry. An example of this adjustment method will be described later with reference to FIG. 9.

In an embodiment, the impedance real part component of the reader side resonant circuit 10 is adjusted by adjusting the resistance value of the resistance portion 13. In the embodiment, by adjusting at least one of the inductance of the coil portion 11 and the capacitance of the capacitor portion 12, the impedance imaginary part component of the reader side resonant circuit 10 is adjusted.

As long as the reader side resonant circuit 10 and the sensor side resonant circuit 20 are formed such that the gain-loss coupling circuit has parity-time symmetry, at least one of the resistance value of the resistance portion 13, the inductance of the coil portion 11, and the capacitance of the capacitor portion 12 in the reader side resonant circuit 10, and the inductance of the coil portion 21 and the capacitance of the capacitor portion 22 in the sensor side resonant circuit 20 may not be variable. In other words, at least one of these may be a fixed value.

Although the actual value of each portion (coil portion, capacitor portion, resistance portion) of the reader side resonant circuit 10 and the sensor side resonant circuit 20 is not particularly limited, it is preferable to select from a set of numerical ranges as exemplified below because the circuit can be configured using general-purpose elements.

(Reader Side Resonant Circuit 10)

Inductance L11 of Coil Portion 11:

Since L11 is required to obtain an inductance equivalent to that of L21, it is about 30 to 35 (nH) (nH is a unit symbol indicating nanohenry).

Capacitance C12 of Capacitor Portion 12:

C12 is determined, for example, by three capacitors constituting a Clapp oscillation circuit. At this time, each of capacitors $C_1$, $C_2$, and $C_3$ is preferably in the range of about 100 to 300 (pF) in order to stably operate the Clapp oscillation circuit. At this time, $C_{12}$, which is the combined capacitance, is about 30 to 100 (pF).

Resistance Value R13 of Resistance Portion 13:

The resistance value R13 is about −700 to −2000 (Ω). Here, the minus sign given to the resistance value (that is, the resistance value is negative) apparently indicates that the element characteristically exhibits a decrease in current with respect to an increase in the voltage applied between the terminals.

As described above, at least one of the resistance value R13 of the resistance portion 13, the inductance L11 of the coil portion 11, and the capacitance C12 of the capacitor portion 12 is variable.

Note that the resistance value R13 of the resistance portion 13, the inductance L11 of the coil portion 11, and the capacitance C12 of the capacitor portion 12 may not be variable and may be fixed.

(Sensor Side Resonant Circuit 20)

Inductance L21 of Coil Portion 21:

In an example where the sensor side resonant circuit is formed on a contact lens, the coil portion is formed as a circular circuit pattern around the outer peripheral edge of the contact lens (the outer peripheral region excluding the central region corresponding to the pupil). This circular circuit pattern is not a completely closed circular ring, but a circular ring with a predetermined small section missing, and the coil is connectable to the resonant circuit through two coil ends, which are both ends of the missing small section.

In an example of the present invention, the coil portion has one turn. Since tears exhibit a capacitance component between electrodes, when a coil (antenna) with two or more turns is mounted on a contact lens or inside a soft contact lens with a high water content, the capacitance component due to the tear becomes a large disturbance, and the resonance frequency designed in advance changes significantly to the extent that it cannot be ignored. Therefore, in the example of the present invention, the number of turns is defined as one.

The disposition configuration itself of the coil portion, the resistance portion, and the capacitor portion formed on the contact lens (or under the surface layer thereof) can refer to conventionally known technology (so-called circuit configuration in smart contact lenses and its formation method), and by replacing these resistance portions with variable resistance sensor elements adapted to the present invention, the sensor side resonant circuit of the sensor system of the present invention can be constructed.

Figure 26:
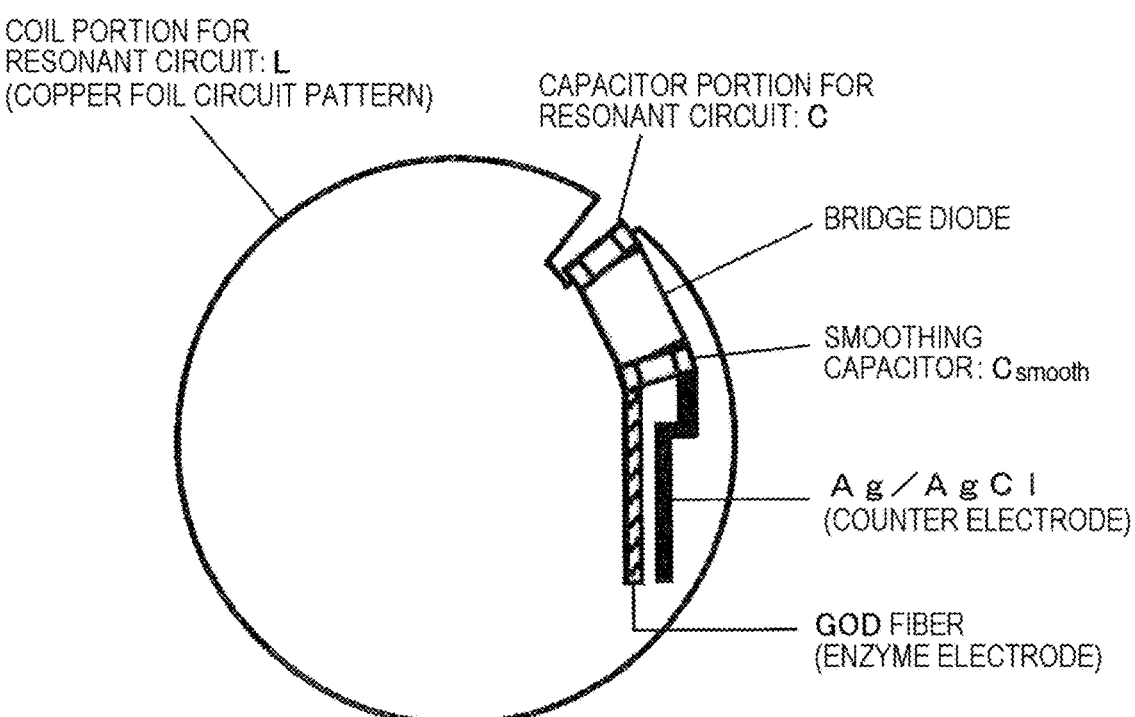
FIG. 26 is a schematic diagram showing a configuration of the resonant circuit-equipped bipolar electrochemical measurement device.

FIG. 26 is a diagram showing an example of configuration of a sensor side resonant circuit suitable for formation on a contact lens. As shown in FIG. 26, a circular copper foil circuit pattern (coil portion: L), a capacitor (C) for a resonant circuit, a variable resistance sensor element (bipolar glucose sensor element of a bipolar type having a GOD fiber as an enzyme-modified electrode (working electrode) and an Ag/AgCl counter electrode) are disposed as parallel resonant circuits. A bridge diode and a smoothing capacitor can be appropriately provided for the purpose of rectification such as full-wave rectification or half-wave rectification.

In the example of circuit formation on (or under the surface layer of) a contact lens as described above, L21 is determined by a one-turn coil that fits within the diameter of the contact lens. Therefore, under the condition of a one-turn coil mounted on a contact lens, L21 is about 30 to 35 (nH). Capacitance C22 of Capacitor Portion 22:

Since C22 is required to have a capacitance equivalent to that of C12, it is about 30 to 100 (pF).
Resistance Value R23 of Variable Resistance Sensor Element (Resistance Portion) 23:

When using the enzyme-modified electrode (carbon nanotube film (bipolar glucose sensor element) described in International Publication WO2012-002290) used in the examples of the present invention, the resistance value R23 of the loss resonator incorporating the bipolar glucose sensor element shows about +700 to +2000 ($\Omega$). With this resistance value as the initial value, the resistance value R23 of the variable resistance sensor element 23 shows a change of about 5 ($\Omega$)/0.1 (mM).
(Configuration of Variable Resistance Sensor Element)

As described above, the variable resistance sensor element may be configured to be able to sense various objects to be sensed (substances and physical quantities). For example, when the object to be sensed is a substance contained in a fluid (such as a substance dissolved in a liquid such as water), the variable resistance sensor element can be configured to change its resistance in response to a fluid (solution or suspension) containing the substance to be sensed.

Examples of the fluid include one or more fluids selected from the group consisting of tears, saliva, sweat, urine, feces, exhaled breath, blood, lymph, interstitial fluid, cell fluid, tissue fluid, organ fluid, and other body fluids.

Objects to be sensed are not particularly limited, and include, for example:

glucose in tears, blood, saliva, and interstitial fluid;
lactate in sweat, saliva, interstitial fluid, and blood;
alcohol in exhaled breath and sweat;
cortisol in sweat, saliva, and tears;
proteins in tears, sweat, saliva, and interstitial fluid;
antibodies in tears;
bacteria in saliva;
adrenaline and stress substances in sweat,
and the like.

Furthermore, examples of objects to be sensed include metabolites (glucose, lactate, urea, or the like), ions (sodium, potassium, calcium, magnesium, chlorine, or the like), alcohol, stress markers (cortisol, catechol, or the like), and cancer markers (exosomes, or the like), inflammatory markers (matrix metalloproteinase, procalcitonin, ferritin, or the like), and the like.

Among the objects to be sensed, glucose in tears is one object to be sensed for which the usefulness of the sensor system according to the present invention is particularly remarkable because the amount of glucose in tears is extremely small and the amount of change is also very small, and it is difficult to configure (a circuit in which a sensor is disposed on the surface of the eyeball and the sensor and an external measurement device are connected by wire).

Specific examples of the variable resistance sensor element capable of sensing the object to be sensed in the fluid described above include enzyme electrodes and other chemical resistors (using metal oxides, graphene, and conductive polymers), and include a cell-type sensor (bipolar type or tripolar type) using an enzyme electrode with selective reactivity to glucose as a working electrode, an FET-type sensor using a graphene surface modified with a glucose-reacting enzyme as a channel, and the like. The enzyme electrode is preferably of a bipolar type from the viewpoint of circuit simplification, and for example, the carbon nanotube film described in International Publication WO2012-002290 can be a preferred bipolar enzyme electrode for sensing glucose.

The main configuration of the carbon nanotube film described in International Publication WO2012-002290 (or U.S. Pat. No. 5,652,724 of its corresponding Japanese application or U.S. Pat. No. 8,921,084 of its corresponding US application) is a carbon nanotube film (more preferably, a free-standing carbon nanotube film) including a carbon nanotube aggregate formed by assembling a plurality of carbon nanotubes and a plurality of enzymes contained in the plurality of carbon nanotube aggregates.

This carbon nanotube film can be preferably disposed on the surface of a contact lens or under the surface layer of a soft contact lens through which tears can permeate because the entire device can be a thin and flexible film-like bipolar enzyme electrode. Accordingly, this carbon nanotube film can be preferably used as a sensor element of a sensor side resonant circuit when the sensor system according to the present invention is applied to a smart contact lens.

Examples of variable resistance sensor elements whose resistance value changes according to various physical quantities (heat, light, current, voltage, electric field, magnetic field, speed, vibration, force (including pressure), and shape change (including strain)) include a strain gauge whose resistance value changes according to shape change, a resistance temperature detector whose resistance value changes according to temperature changes, a photoconductive element (CdS cell) whose resistance value changes according to light intensity, a piezoresistive element whose resistance value changes according to pressure, and the like.

The location where the object to be sensed is not particularly limited, and examples thereof include not only living organisms (animals (humans, livestock, pet animals, or the like) and plants), but also minerals, rivers, oceans, man-made objects (devices, buildings, or the like), the atmosphere, the surfaces and interiors of planets, outer space, and the like.

A mode of the sensor device in which the sensor side resonant circuit 20 is implemented can be appropriately determined according to the object to be sensed and the location where it exists. A sensor device may be used as a wearable device such as a smartwatch.

As one example of the embodiment, the sensor side resonant circuit 20 is located on a surface of or inside an object. Objects include living organisms (including animals and human bodies), clothing, bedding, diapers, buildings, crops, implants, glass, food containers, and other polymeric substances.

The sensor side resonant circuit 20 is formed on the surface of or inside an object through which an electromagnetic field can pass. The material of the object is a material that has a small influence on the magnetic field resonant coupling. For example, the sensor side resonant circuit 20 is located on a contact lens. The sensor side resonant circuit 20 is, for example, provided on the surface of the contact lens or embedded inside the contact lens.

When the object to be sensed is glucose in tears, the sensor device preferably has a sensor side resonant circuit 20 formed on a contact lens.

As another example, the sensor side resonant circuit 20 is located on the surface of the human body or inside the body. The sensor side resonant circuit 20 is, for example, provided on the surface of a living body (skin, organ, blood vessel, brain, tooth, or the like) or implanted in the body. When the object to be sensed is a biochemical substance contained in human sweat, the sensor device is exemplified by a mode such as a patch-type sensor device that is attached to the skin.

When the object to be sensed is a biochemical substance contained in the blood of an animal, the sensor device is exemplified by a mode such as a so-called implantable device (a device implanted in a target organ or blood vessel in vivo).

As still another example, the sensor side resonant circuit 20 is provided on the surface of polymer or glass, or embedded inside polymer or glass, for example.

In addition, a plurality of sensor side resonant circuits 20 may be provided. For example, when measuring sleep-related data, a plurality of sensor side resonant circuits 20 may be provided to measure brain waves, heart rate, blood pressure, pulse, movement, and other sleep-related parameters.

When measuring data related to sleep, a plurality of sensor side resonant circuits 20 (sensors) provided with sensor side resonant circuits 20 may be embedded in sleepwear, worn directly on the body, or embedded in bedclothes (pillows, mats, or the like).

Also, as another application of the sensor side resonant circuit 20, it may be used in a food-related business. The sensor side resonant circuits 20 (sensors) may be attached to or embedded in food packages (including food containers). In this case, the sensors can measure various parameters such as maturity and freshness of the food. For example, the sensors can detect chemical changes in food. The sensors can also detect that food has spoiled. As another example, the sensors can detect temperature changes in frozen or refrigerated goods. By using sensors in this manner, deterioration of food can be detected in advance and food loss can be reduced.

Examples of uses of the sensor system of the present application that can detect minute resistance changes are not limited to the above, but it can be used in various fields such as water quality surveys of pools and aquariums, mental health care by detecting stress hormones, detection of aging of buildings, disaster countermeasures such as earthquake prediction, and smart agriculture.

As illustrated in FIG. 1, the sensor system of the present invention is connected with a measurement device 30 that measures the resistance value of the sensor element 23 in the sensor side resonant circuit 20 through the reader side resonant circuit 10. Further, a power supply device that wirelessly supplies power of a predetermined frequency to the sensor side resonant circuit 20 is also provided. These measurement devices and power supply devices may be appropriately selected from commercially available devices and used, or may be constructed for the present invention.

In the example shown in FIG. 1, a vector network analyzer (VNA) is used as such a measurement device and power supply device. The VNA has a function of applying a frequency sweep type signal to a connected device under test and measuring an amplitude and a phase of reflected waves and traveling waves to evaluate the frequency characteristics of the device. The VNA is also responsible for supplying AC power to the device with frequency sweeps. In examples below, a VNA manufactured by Anritsu Corporation (product number MS46122B) is used and has a power output of 3.2 (mW).

EXAMPLES

Hereinafter, experimental results are shown that establishment of PT symmetry is proven and that sharpening of the resonance frequency (sensitivity amplification) is confirmed when a sensor side resonant circuit (LCR parallel resonant circuit configured as a loss circuit) and a reader side resonant circuit (LCR parallel resonant circuit configured as a gain circuit) including variable resistance sensor element as resistance portions are coupled as a loss-gain coupling circuit through magnetic field resonant coupling.

In quantum mechanics, since all operators corresponding to observable physical quantities (observables) are real numbers, there is a principle that their energy operators (Hamiltonian operators) are Hermitian.

$$H = H^\dagger$$

Here, $$H$$

is a physical quantity (observable) that represents the energy of the system, and thus the eigenenergy that the system can take can be specified by solving its eigenvalue.

On the other hand, in recent years, it has been found that the eigenvalues of non-Hermitian operators can be real numbers. The principle to achieve this is PT symmetry proposed by Bender and Boettcher in 1998 (Non-Patent Document 10).

Here, parity (P) refers to space inversion (x→−x) and time (T) refers to time inversion (t→−t).

If a target physical system does not change with these two PT transformations, its Hamiltonian operator will have real eigenvalues in spite of being non-Hermitian. That is, under the condition that the PT symmetry is satisfied, the eigenvalues of the complex numbers that the non-Hermitian Hamiltonian generally has are real eigenvalues (the imaginary part component is 0).

A point at which a complex eigenvalue changes to a real eigenvalue in this way is called an exceptional point (EP). Fusion of complex eigenvalues and non-Hermitian degeneracy are observable in the EP. That is, in one system, two or more different eigenvalues have the same energy level. PT symmetry in such non-Hermitian systems has been applied to various physical systems (for example, coupling waveguides (Non-Patent Documents 11 and 12), microresonators (Non-Patent Documents 13, 14, 15, and 16), plasmonics (Non-Patent Document 17), microwave resonators (Non-Patent Documents 18 and 19), lasers (Non-Patent Documents 20, 21, and 22), atom spectrum (Non-Patent Document 23), mechanical system (Non-Patent Document 24), acoustic system (Non-Patent Documents 25 and 26), and the like). Among them, application to resonant coupling systems including electrical elements (coils, capacitors, resistors) was demonstrated for the first time by Schindler et al. in 2011 (Non-Patent Document 27), and an intraocular pressure sensor (Non-Patent Document 1), a micro position sensor (Non-Patent Document 2), and a glucose sensor (Non-Patent Document 28) using this principle have been reported.

In the case of many battery-free passive sensors that use a conventional resonant coupling circuit (loss-loss coupling circuit), in order to read changes on the sensor side with high sensitivity, the issue is how to prevent energy dissipation by the resonant coupling system and improve the Q value (sensitivity) of the system. By introducing PT symmetry (a state in which the energy balance between the gain of the gain resonant circuit and the loss of the loss resonant circuit is maintained) to such an issue, as a result, a nearly lossless (high Q value) coupling state can be created near the EP.

In the present example, by performing a mathematical simulation of PT symmetry in a magnetic resonant coupling model (a configuration in which two LCR parallel resonant circuits (one parallel resonant circuit includes a variable resistance sensor as a resistance portion) is connected in parallel) and actually constructing a corresponding electric circuit or electronic circuit, the existence of an EP whose eigenvalue is the real part was experimentally confirmed. In particular, it was clarified that the change of the coupling system against the weak perturbation from the outside world (this paper deals with changes in the impedance of a chemical resistor due to glucose and lactate concentrations) becomes remarkably large near the EP.

(Sharpening of Sensor Drive Frequency Through Parity-Time (PT) Symmetrical Covalent Coupling)

Figure 2:
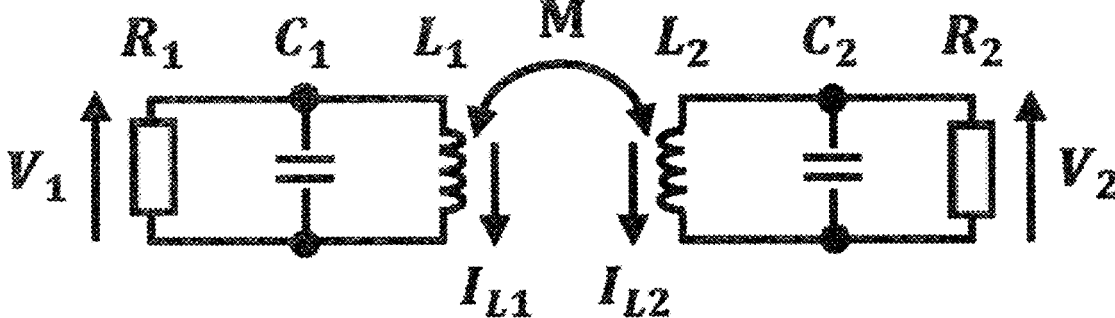
FIG. 2 is an equivalent circuit diagram of a magnetic resonant coupling system.

The coupling system used in the present example is configured with two LCR parallel resonant circuits, and the LCR parallel resonant circuit on the primary side was treated as a reader side resonant circuit, and the LCR parallel resonant circuit on the secondary side was treated as a sensor side resonant circuit (FIG. 2). From the equivalent circuit diagram shown in FIG. 2, an operator (Formula 12 below) relating to the amplitude value of the charge stored in each capacitor is derived. Formula 12 below and its detailed derivation process will be described later. Other formulas and their detailed derivation process will be described later.

This is synonymous with coupling mode analysis in which a complex sine wave element is added to a magnetic resonant coupling circuit, and the eigenvalue of the system can be calculated by solving the determinant for $\omega$ (Formula (46) below).

Here, by changing the degree of coupling of the LCR parallel resonant circuit using a simulation model, changes in the eigenvalues of each system in the loss-loss coupling circuit and the gain-loss coupling circuit are observed.

Each component used is as follows.

Inductances L1 and L2 of the copper loop coil (wire diameter: 0.238 (mm), loop diameter: 13 (mm)) are 32 (nH). Capacities C1 and C2 of the multilayer ceramic capacitors connected to the coils are 90 (pF).

A mutual inductance M between the two LCR parallel resonant circuits is defined as follows.

$$M = k(L1 \times L2)^{(1/2)}$$

In the above formula, k is a coupling coefficient.

In order to achieve PT symmetry, it is necessary to design each reactance element (inductor/capacitor coil and capacitor) to be equal and have opposite resistance components.

Figure 3:
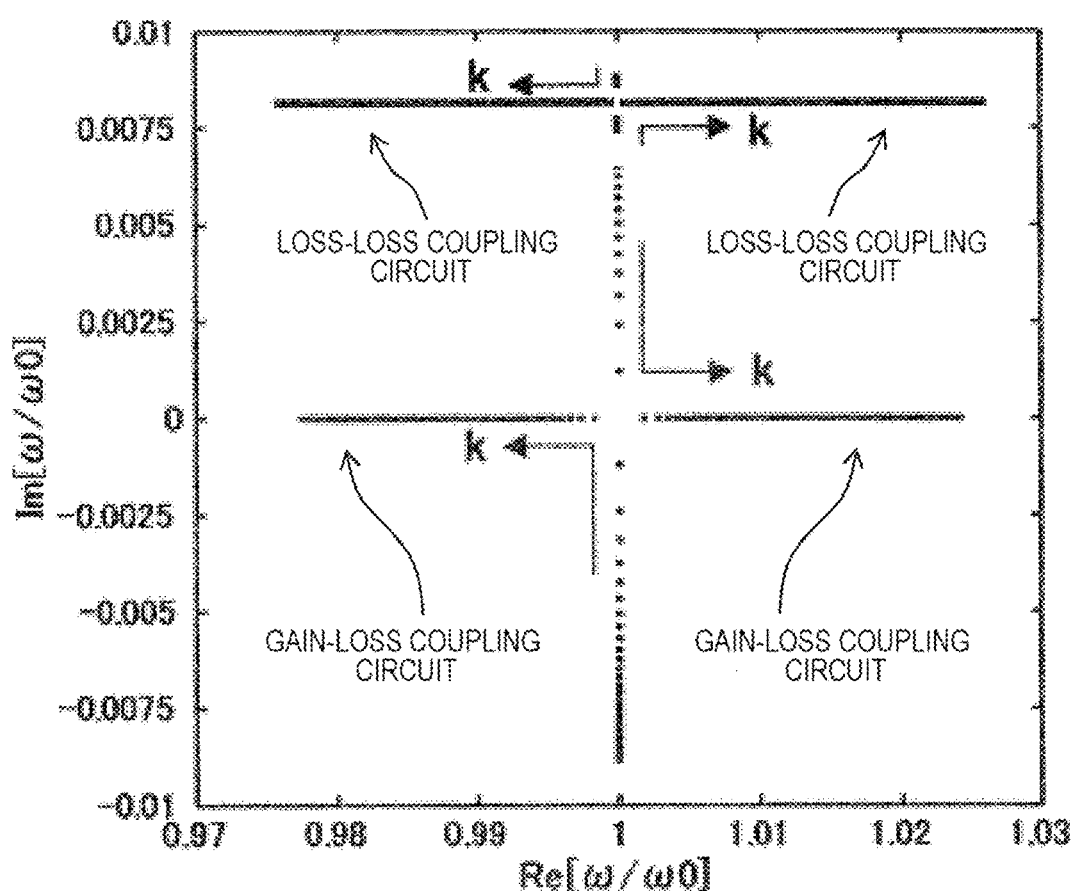
FIG. 3 is a graph showing Nyquist plots of a loss-loss coupling circuit and a gain-loss coupling circuit when a coupling coefficient k is changed from 0 to 0.05.
Figure 4:
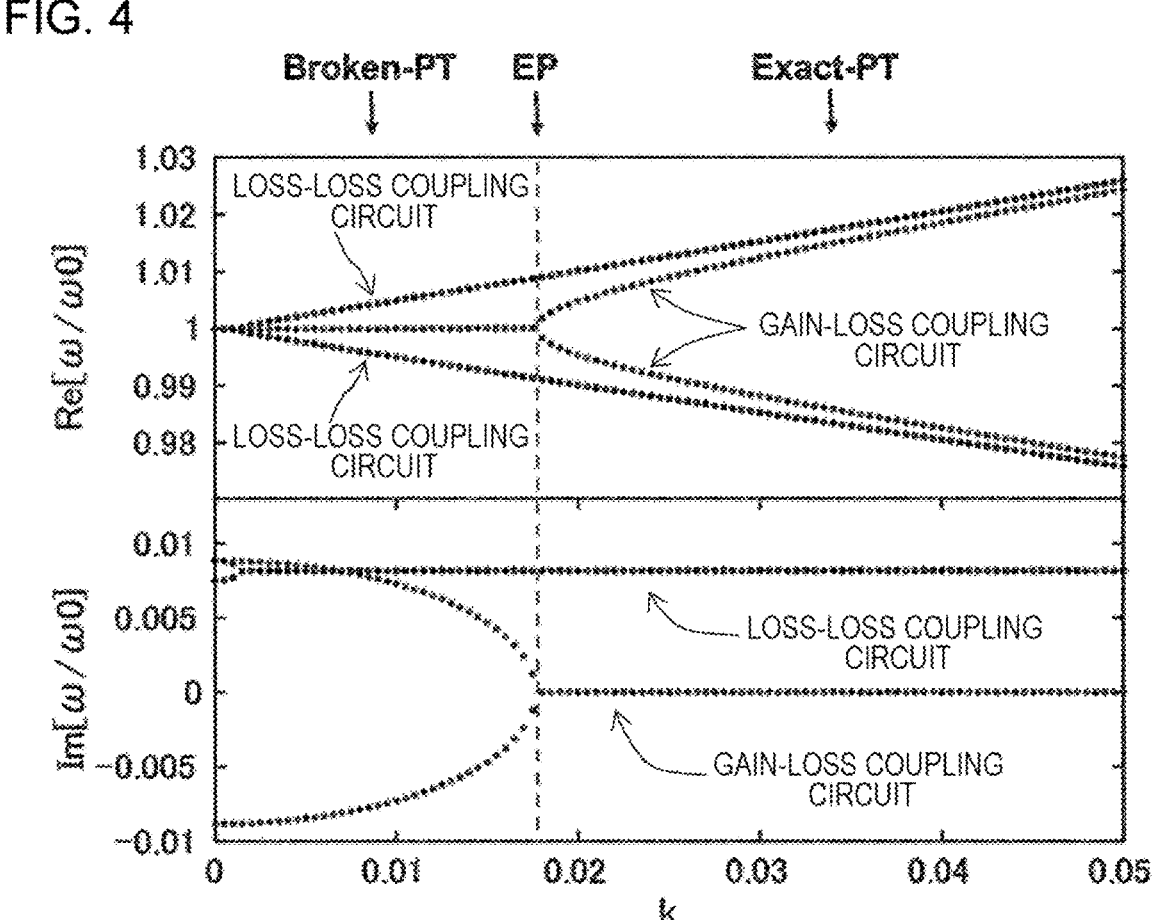
FIG. 4 is a graph showing impedance plots of the loss-loss coupling circuit and the gain-loss coupling circuit when the coupling coefficient k is changed from 0 to 0.05.

FIG. 3 shows the graph of the Nyquist plot and FIG. 4 shows the graph of the impedance plot when the coupling coefficient k is changed from 0 to 0.05 using the obtained calculation formula.

From the graphs in FIGS. 3 and 4, in gain-loss coupling, the imaginary part component of the eigenvalue becomes 0 after EP (k=0.017709), and as a result, the coupling system maintains the real eigenvalue. A region that can maintain this real eigenvalue (k>0.017709) is called "Exact-PT", and a region that has a complex eigenvalue (k<0.017709) is called "Broken-PT". On the other hand, in loss-loss coupling, it can be seen that there is no region where the imaginary part component becomes 0 due to changes in the coupling coefficient k.

In general, magnetic resonant coupling is mainly based on magnetic field coupling in the near field, and the coupling coefficient is a dimensionless number representing how much the magnetic field generated from a primary coil interlinks with a secondary coil. The coupling coefficient k can be defined by a vertical distance d between the coils, a horizontal displacement l (l is a lower case letter of L), a tilt angle $\theta$, a magnetic permeability $\mu_0$, and a coil radius r1, r2=13 (mm), number of turns N1, N2=1, and inductance L1, L2=32 (nH) of each resonant circuit (FIG. 5, Formula 47 below, and Non-Patent Document 30).

Figure 6:
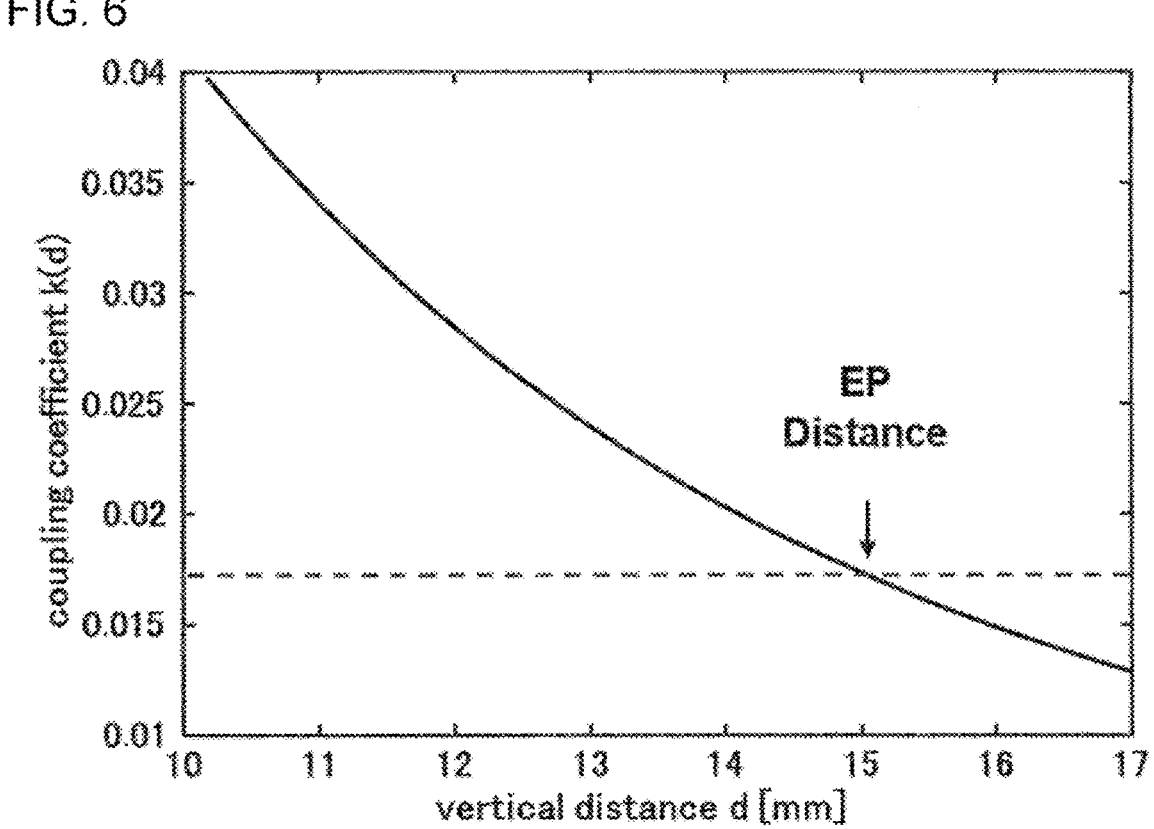
FIG. 6 is a graph showing a relationship between changes in vertical distance and changes in coupling coefficient.

In the present example, the coupling coefficient (simulation value) was calculated when the distance d between the resonant circuits disposed in parallel was changed while the parameters other than the vertical distance were fixed, and the EP distance was obtained (graph in FIG. 6).

Next, an electronic circuit corresponding to the simulation values is actually constructed, and an input impedance when the distance between the resonant circuits is changed is observed on a network analyzer.

Figure 7:
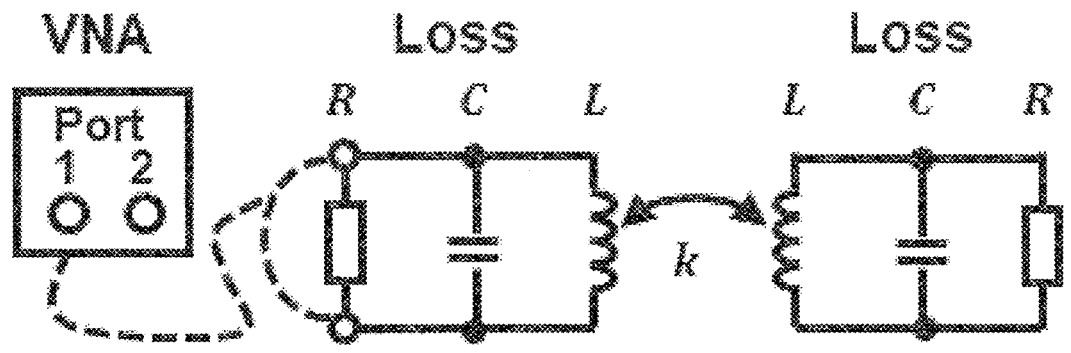
FIG. 7 is a block diagram showing a magnetic resonant coupling system for each of a loss-loss coupling circuit and a gain-loss coupling circuit.
Figure 7:
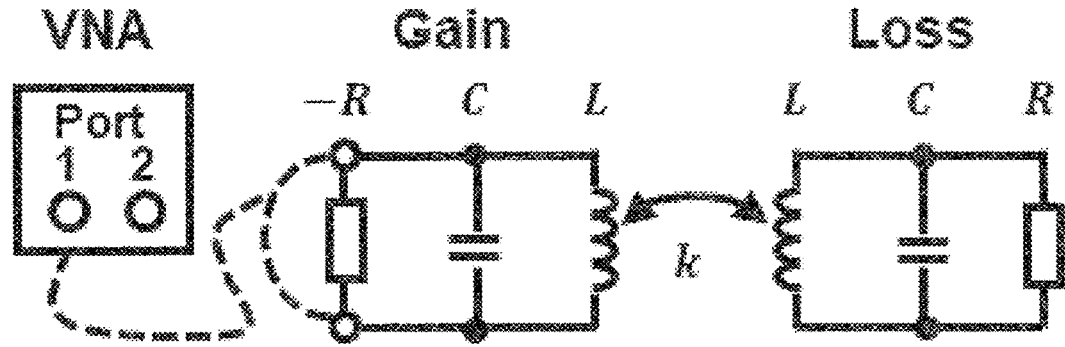
Figure 8:
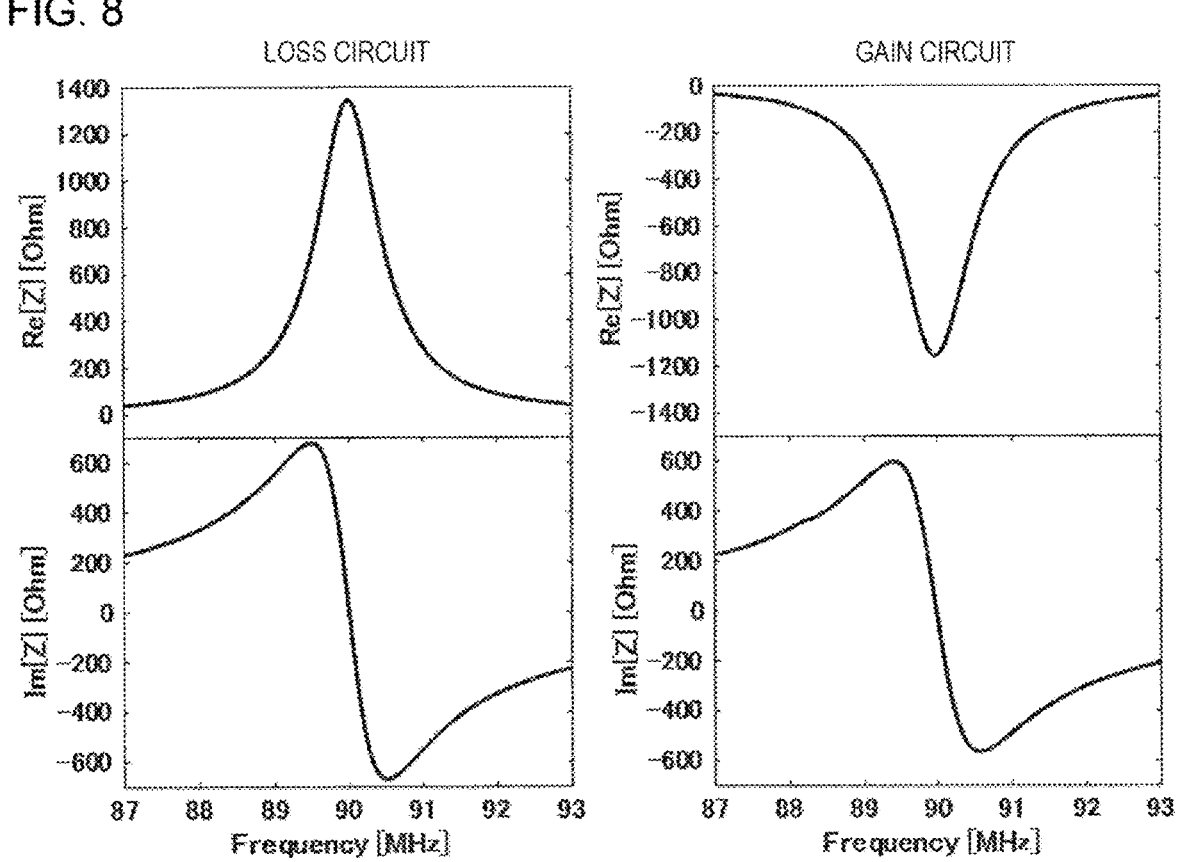
FIG. 8 is a graph showing respective reflection coefficient characteristics (impedance form) of a loss resonator and a gain resonator.

Here, the resonant circuit actually used can be divided into two types: a loss circuit and a gain circuit, and a conventional dissipative system is called a loss-loss coupling circuit, and a partially conservative system that achieves PT symmetry near the resonance point is called a gain-loss coupling circuit. At this time, an equivalent circuit of each resonant circuit can be expressed as shown in FIG. 7 using a coil (inductance) L, a capacitor (capacitance) C, and a resistance R which are electrical elements, and the real part of the impedance of each resonant circuit (loss circuit and gain circuit) at the resonance point exhibits a positive value or a negative value. FIG. 8 is a graph showing respective reflection coefficient characteristics (impedance form) of a loss resonator and a gain resonator. FIG. 8 shows the impedance characteristics of the resonant circuit (loss circuit and gain circuit) created in the present example.

An equivalent negative resistance that constitutes a resonant circuit, which is a gain circuit, has been implemented by a feedback oscillation circuit using an operational amplifier or a MOSFET, but in this embodiment, but in the present example, a Clapp oscillation circuit using a dual-gate MOSFET (manufactured by NXP Semiconductors, product number BF992) with a small gate-drain capacitance was created (FIG. 9), and a negative resistance with high frequency stability was achieved.

Each parameter used is as follows.

Bias resistance $R_1$=4.7 (k$\Omega$)

$R_2$=2.2 (k$\Omega$)

Source resistance $R_s$=120 ($\Omega$)

Source capacitor $C_s$=180 (pF)

Bypass capacitors $C_i$, $C_o$=100 (pF)

Oscillation capacitors $C_1$, $C_2$=300 (pF)

$C_3$=270$\pm$(10 to 50) (pF)

Inductance L=32 (nH)

In the present example, the capacitor $C_3$ (resistance portion) in the reader side resonant circuit 10 is variable, and the resonance frequency of the reader is adjusted such that the gain-loss coupling circuit has PT symmetry.

Figure 10:
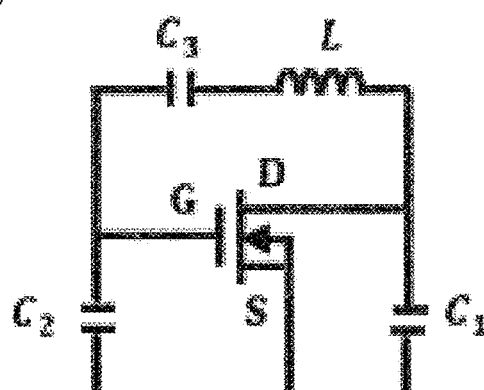
FIG. 10 is a diagram showing decomposition of a Clapp oscillation circuit and deformation of a series circuit of an FET and an oscillation capacitor.
Figure 10:
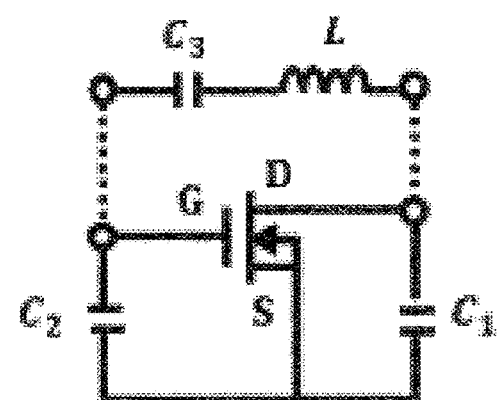
Figure 10:
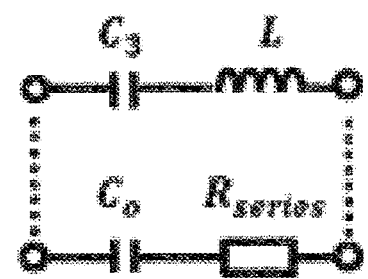

The implemented Clapp oscillation circuit can be treated as an LCR parallel connection circuit by circuit deformation. First, a simplified Clapp oscillation circuit is decomposed as shown in FIG. 10(*a*), FIG. 10(*b*), and FIG. 10(*c*) in order, and a circuit composed of an FET and oscillation capacitors $C_1$ and $C_2$ is represented as a series circuit of a capacitance component $C_o$ and a resistance component $R_{series}$ (FIG. 10(*c*)).

Here, using the equivalent circuit diagram (FIG. 11) for calculating the negative resistance, the impedance of series-connected $C_o$ and $R_{series}$ can be calculated (Formula 51 below).

Figure 12:
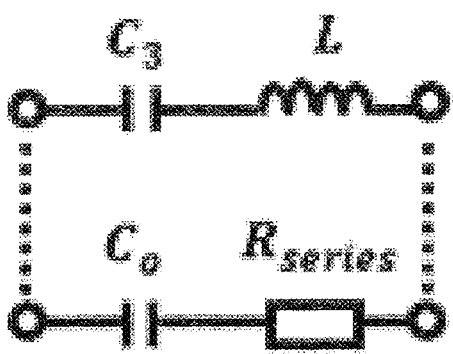
FIG. 12 is a diagram showing parallel circuit conversion of series input impedance.
Figure 12:
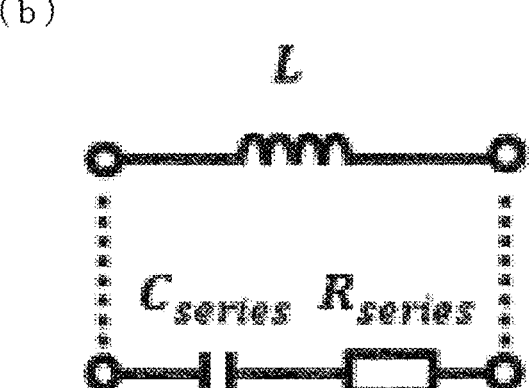
Figure 12:
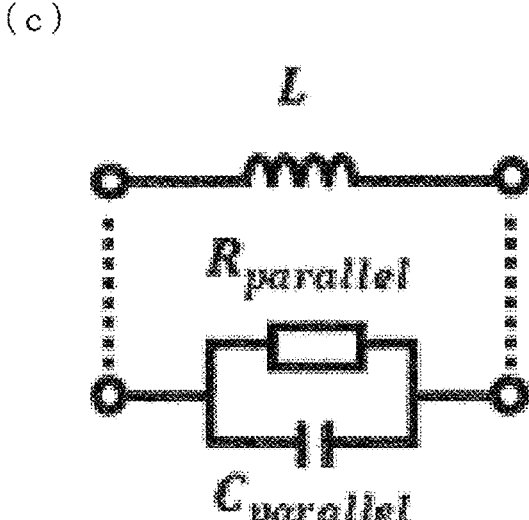

Using the definitional formula obtained here, the input impedance when viewed from the inductance side can be expressed as $C_{parallel}$ and $R_{parallel}$ connected in parallel as shown in a deformed manner in FIG. 12(*a*), FIG. 12(*b*), and FIG. 12(*c*) in order (Formulas 55 and 56 below).

From Formulas 55 and 56, it can be seen that the negative resistance $R_{parallel}$ of the gain resonant circuit is defined by a mutual conductance gm of the FET (ratio of the amount of change in the drain current to the amount of change in the gate voltage), a resonant angular frequency @, and oscillation capacitors $C_1$ and $C_2$, and exhibits a negative value. Further, the value of the negative resistance can be adjusted in the range of about −800 to −1200 ($\Omega$) by the voltage applied to the FET.

On the other hand, a capacitor $C_{series}$ of the gain resonant circuit is expressed as a composite capacitor of $C_1$, $C_2$, and $C_3$. Here, when the absolute value of the Q value shown in Formula 56 below is sufficiently larger than 1, the component of each parallel element can be approximated as follows.

$$R_{parallel} \approx R_{series} \times Q^2$$

$$C_{parallel} \approx C_{series}$$

From the above, it can be seen that the created gain resonant circuit corresponds to the LCR parallel connection circuit.

Figure 13:
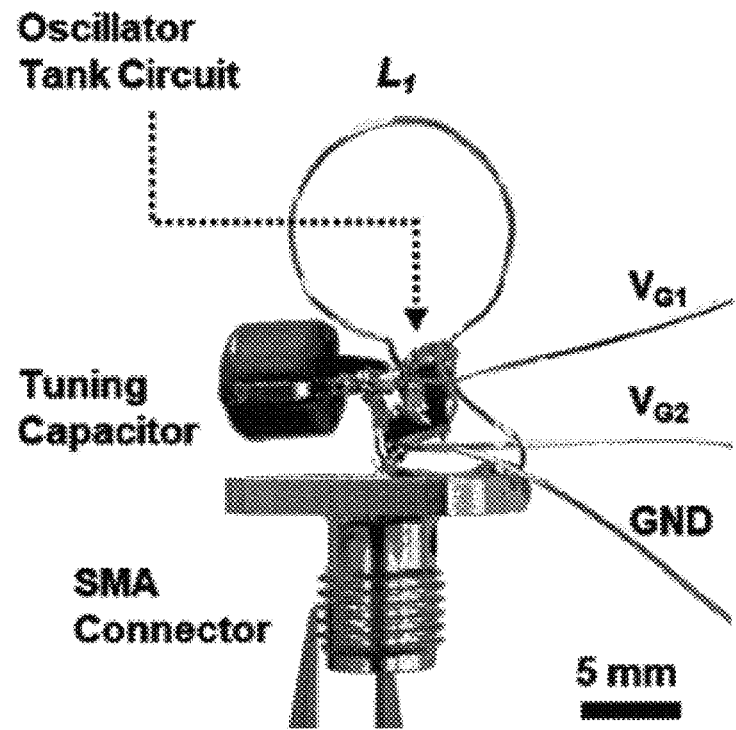
FIG. 13 is a diagram showing the appearance of an actually produced gain resonator (Clapp oscillation circuit).

FIG. 13 is a diagram showing the appearance of an actually produced gain resonator (Clapp oscillation circuit). The negative resistance ($R_1$) of this gain resonator can be adjusted by voltages ($V_{G1}$, $V_{G2}$) applied to the MOSFETs.

Figure 14:
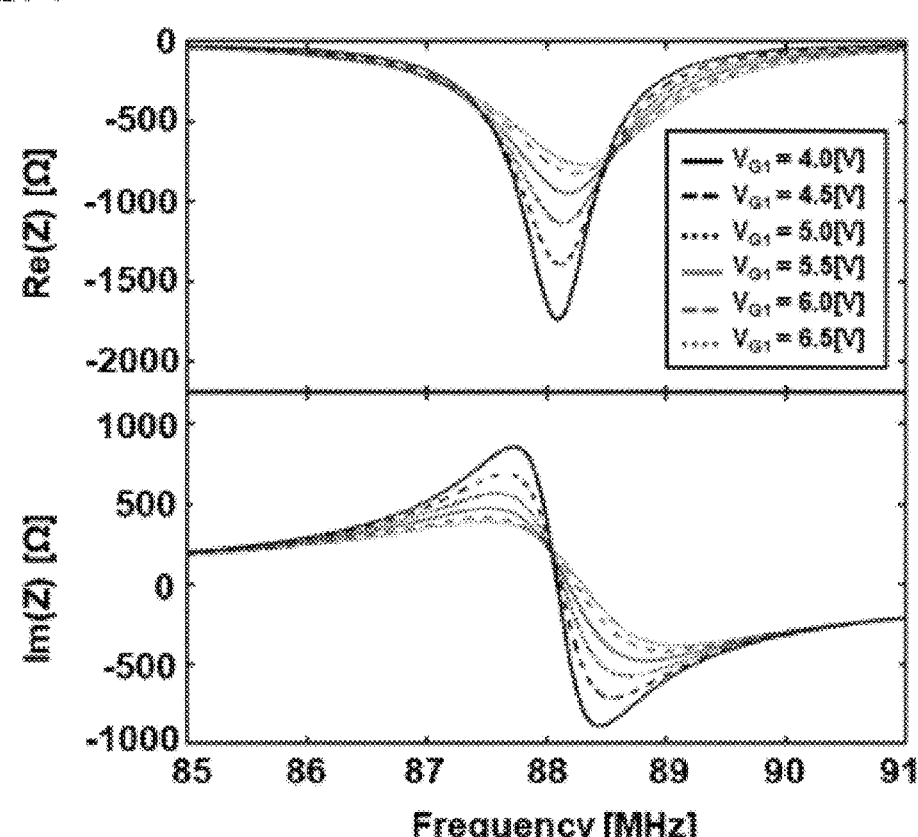
FIG. 14 is a graph showing changes in impedance when $V_{G1}$ is changed.

FIG. 14 is a graph showing changes in impedance when $V_{G1}$ is changed. In order to evaluate the adjustment function of the gain resonator, impedance changes were confirmed when $V_{G2}$ was fixed ($V_{G2}$=6.0 V) and $V_{G1}$ was changed ($V_{G1}$=4.0 to 6.5 V). At this time, the impedance real part component (Re($Z_{in}$)) changed from −17545 ($\Omega$) to −773 ($\Omega$), and the resonance frequency changed from 88.08 (MHz) to 88.29 (MHz).

From the above results, it was found that the gain resonator manufactured in this section can adjust the negative resistance value and the resonance frequency according to the applied voltage. In the following experiments, this gain resonator is used when constructing PT symmetry.

Finally, using these resonant circuits (loss circuit and gain circuit), a dissipative system (loss-loss coupling circuit) and a partially conservative system (gain-loss coupling circuit) were actually constructed, and changes in the coupling system were observed when the distance d (coupling coefficient k) between the resonant circuits was changed.

In the present example, the reflection coefficient was measured using a vector network analyzer (VNA) in order to evaluate the coupling system including a pair of resonant circuits.

A primary-side resonant circuit (reader side resonant circuit) was connected to port 1 of the VNA as shown in FIG. 7, and the input impedance was recorded.

Figures 15, 16:
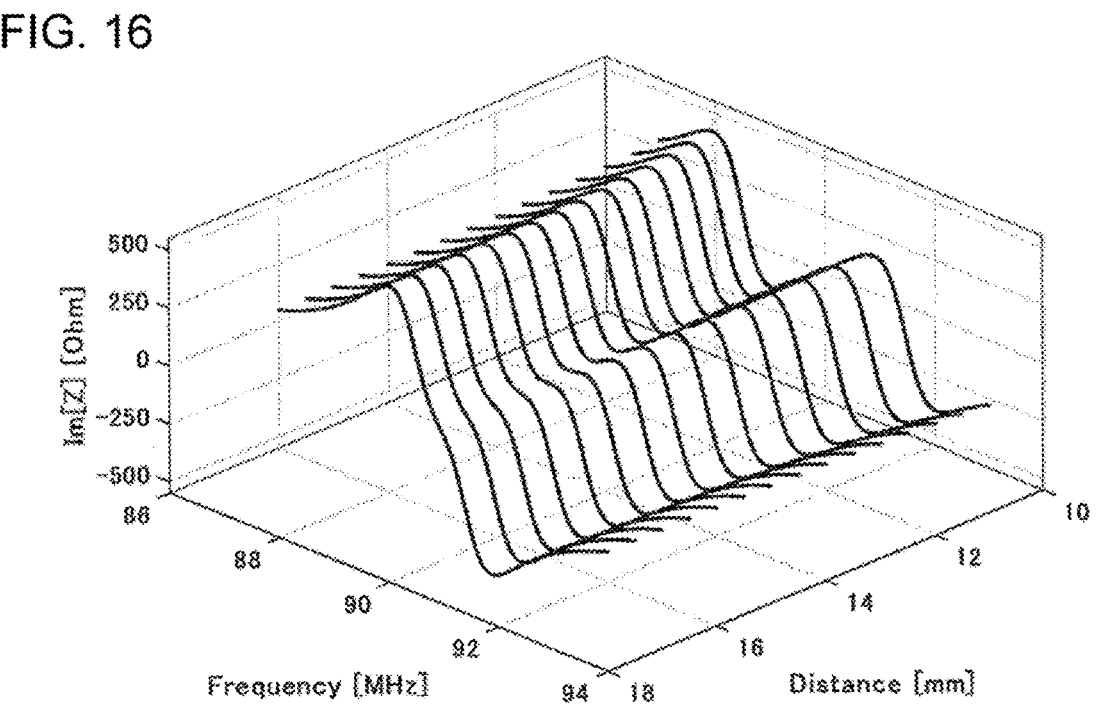
FIG. 15 is a graph showing changes in distance between resonators and changes in reflection coefficient (impedance real part) in a loss-loss coupling circuit.
FIG. 16 is a graph showing changes in distance between resonators and changes in reflection coefficient (impedance imaginary part) in a loss-loss coupling circuit.

In the conventional dissipative system (loss-loss coupling circuit), changes in reflection coefficient when the resonant circuit distance is changed are shown as changes in impedance (real part/imaginary part) (FIGS. 15 and 16).

Since the mutual inductance between the coils changes as the distance between the resonant circuits decreases, it can be seen that the resonance frequency of the coupling system splits into two. This is called a strong coupling region.

Figures 17, 18:
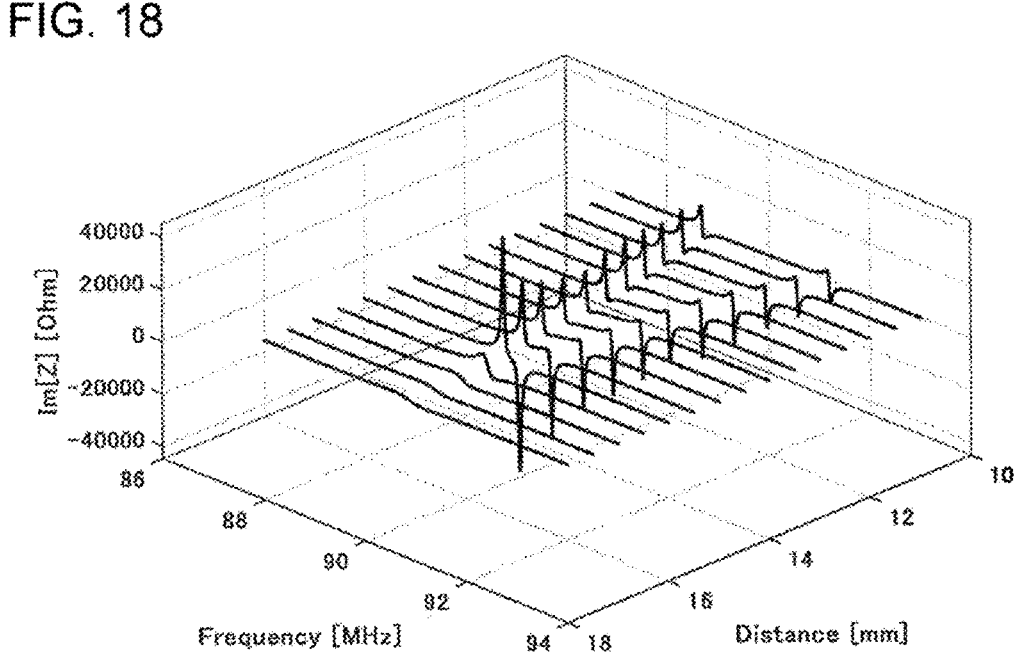
FIG. 17 is a graph showing changes in distance between resonators and changes in reflection coefficient (impedance real part) in a gain-loss coupling circuit.
FIG. 18 is a graph showing changes in distance between resonators and changes in reflection coefficient (impedance imaginary part) in a gain-loss coupling circuit.

On the other hand, even in the partially conservative system (gain-loss coupling circuit), the point where the resonance frequency splits into two can be seen near the distance d=15 (mm) (FIGS. 17 and 18).

Figure 19:
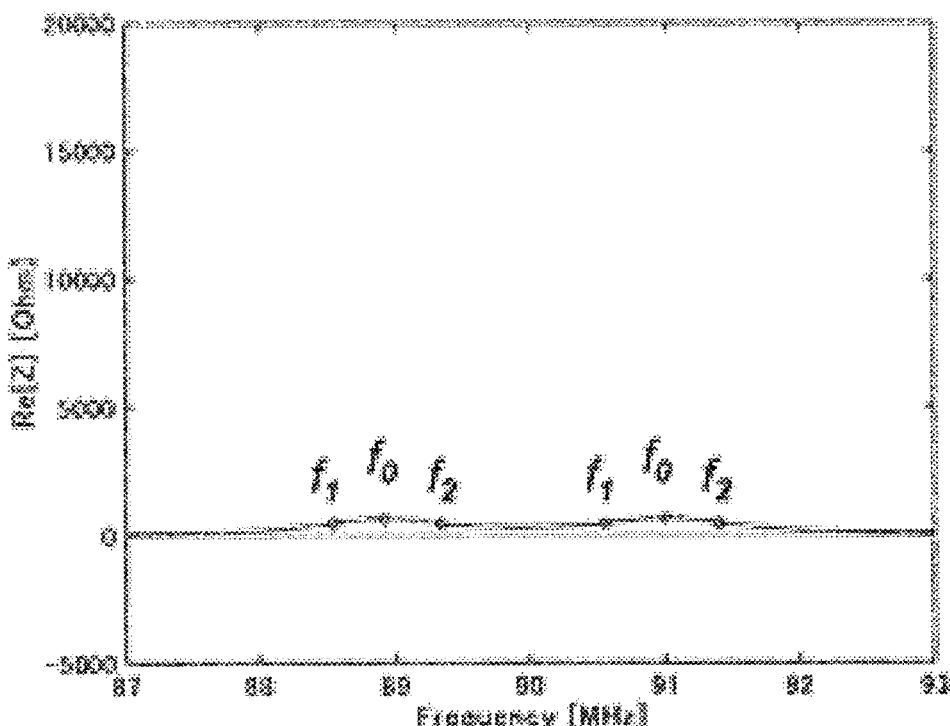
FIG. 19 is a graph showing impedance real part components of each coupling system.
Figure 19:
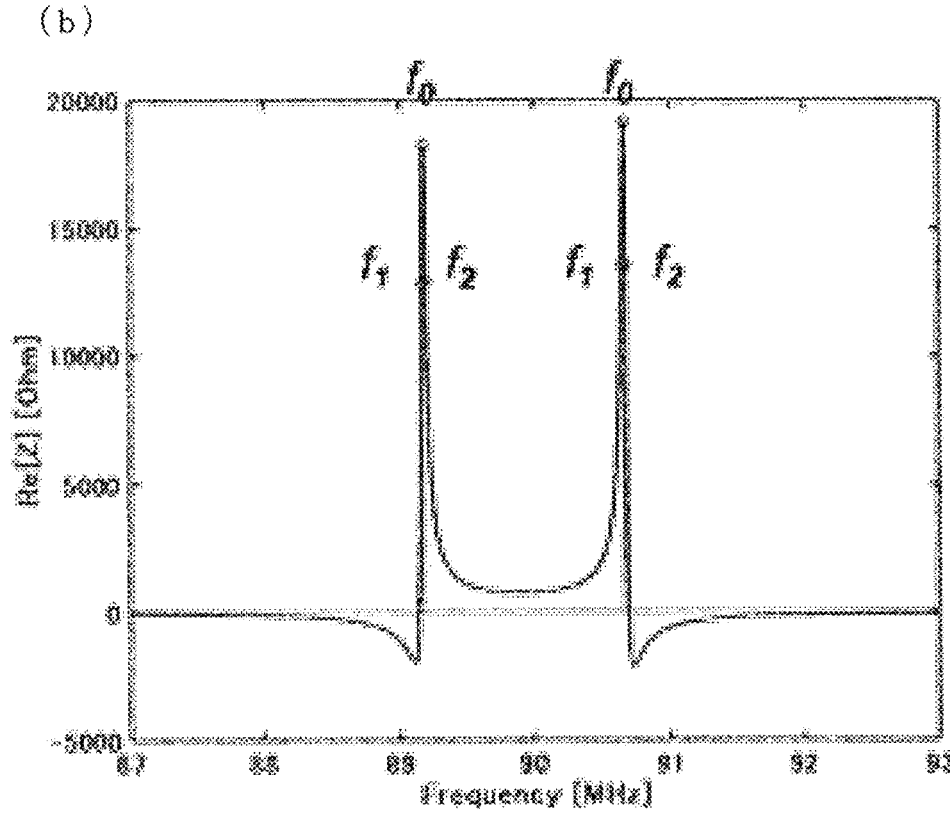

However, it can be seen that the scale of the impedance value near the resonance frequency is increased by about 30 times as compared with the loss-loss coupling circuit. Furthermore, narrowing of the frequency band (sharpening) was observed. This can be evaluated using the sharpness Q=$f_0$/($f_2$−$f_1$) (FIG. 19), and each sharpness is as follows.

Loss-loss coupling circuit: Q=109.35

Gain-loss coupling circuit: Q=3074.21

Further, it can be inferred that PT symmetry in which gain and loss are balanced in terms of energy is maintained near the resonance frequency near the distance d=15 (mm).

Therefore, the state of the eigenvalues in the Exact-PT region (where the imaginary part component of the complex eigenvalues is 0) in the coupling system shown in FIG. 4 is observable as the impedance values of the reflection coefficients that have increased sharply in the actual constructed circuit.

(Relationship Between Amount of Resistance Change (Δr) of Resistance of Sensor Side Resonant Circuit 20 and Impedance ($Z_{in}$))

Figure 20:
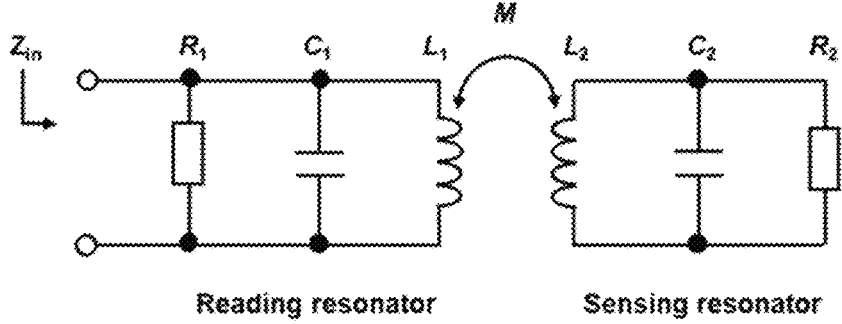
FIG. 20 is an image diagram of a magnetic resonant coupling system converted into an equivalent circuit.
Figure 20:
Figure 20:
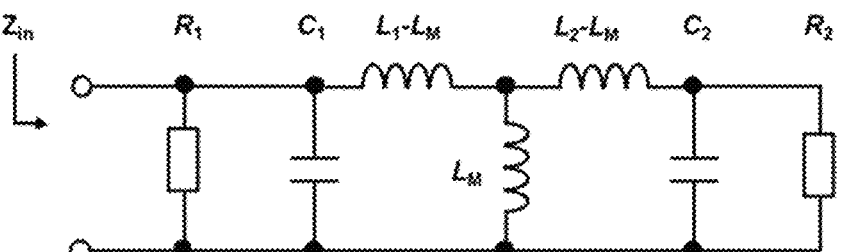

The superiority and versatility of the present invention will be shown by formulating the input impedance ($Z_{in}$) when viewed from the reader side and simulating how the amplitude changes in response to a weak resistance change (Δr) that occurs in the sensor side resistance in the magnetic resonant coupling system configured in the present invention. FIG. 20 is an image diagram of the magnetic resonant coupling system converted into an equivalent circuit. When the magnetic resonant coupling system is converted as shown in FIG. 20, $Z_{in}$ is represented by Formula (1A).

$$Z_{in} = \cfrac{1}{\cfrac{1}{\cfrac{1}{\cfrac{1}{\cfrac{1}{\cfrac{1}{R_2} + j\omega C_2} + j\omega(L_2 - L_M)} + \cfrac{1}{j\omega L_M}} + j\omega(L_1 - L_m)} + \cfrac{1}{R_1} + j\omega C_1}} \tag{1A}$$

Here, $L_n \cdot C_n \cdot R_n$ represents the inductance, capacitance, and resistance of each resonator. Also, $L_M$ ($=k\,(L_1 \times L_2)^{(1/2)}$) refers to mutual inductance, and k is a coupling coefficient.

At this time, a simulation is performed on the change in input impedance when the resistance component of each resonator is changed. The reader side resistance ($R_1$) was changed in the range from −2 (kΩ) to 2 (kΩ). This is for changing the characteristics of the reader side resonator in the range from gain to loss ($R_1 = -2$ (kΩ) to 0 (Ω): gain, $R_1 = 0$ (Ω) to 2 (kΩ): loss).

Next, the sensor side resistance ($R_2$) was changed in the range from 1 (kΩ) to 990 (Ω). This is a parameter that reproduces a weak resistance change (Δr) that occurs in the sensor element. As for the coupling coefficient, by using the value ($k_{EP} = 0.017709$) derived from the eigenvalue simulation results described with reference to FIGS. 3 and 4, the most specific amplitude changes in PT symmetry reproduce the observable EP.

Figure 21:
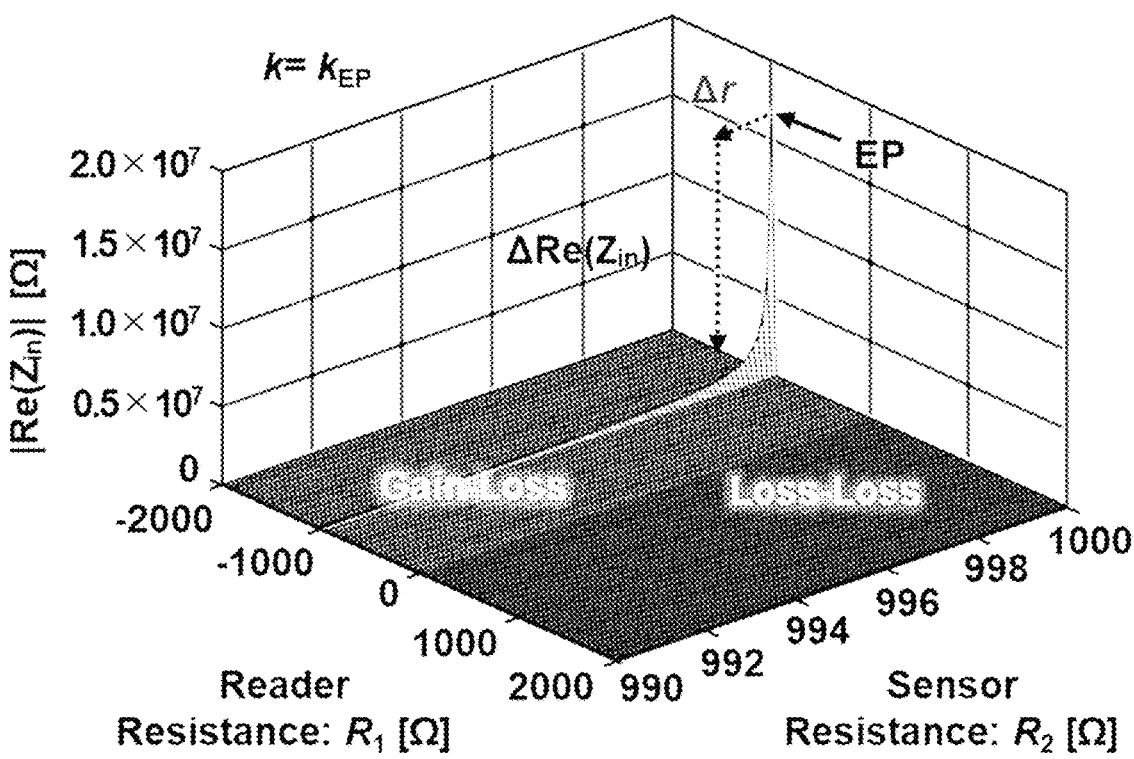
FIG. 21 is a diagram showing a result of calculating an absolute value of an input impedance real part using the above parameters.

FIG. 21 is a diagram showing the result of calculating the absolute value of an input impedance real part ($\text{Re}(Z_{in})$|) using the above parameters. FIG. 21 is divided into regions in the range of $-2000$ (Ω)$\leq R_1 < 0$ and $0 < R_1 \leq 2000$ (Ω), which means gain-loss coupling/loss-loss coupling, respectively. Here, it can be seen that $|\text{Re}(Z_{in})|$ reaches a sharp peak when the reader side resistance is $R_1 = -1$ (kΩ) and the sensor side resistance is $R_2 = 1$ (kΩ).

This means that the balance between gain and loss is maintained on the reader side and the sensor side, and as a result, the system reaches EP under the condition of $k_{EP} = 0.017709$.

Next, it is confirmed how the input impedance ($Z_{in}$) changes with respect to the chemical resistance change (Δr) that occurs on the sensor side. First, the change in $|\text{Re}(Z_{in})|$ with respect to Δr is defined as $\Delta\text{Re}(Z_{in})$ as follows.

$$\Delta\text{Re}(Z_{in}) = |\text{Re}(Z_{in(i)}) - \text{Re}(Z_{in(0)})|$$

Here, it can be seen that $\Delta\text{Re}(Z_{in})$ when the EP in the drawing is changed by Δr shows a very large value. This shows how the balance between gain and loss has collapsed from the state where the balance between gain and loss is maintained (EP), and it can be seen that the rate of change of $\Delta\text{Re}(Z_{in})$ exponentially attenuates as the balance collapses.

From the above, it was found that when the resistance value ($R_2$) on the sensor side changes slightly near the EP, the input impedance real part ($\text{Re}(Z_{in})$) changes abruptly. This means that a very specific amplitude modulation is possible for a weak resistance change that occurs on the sensor side.

Figure 22:
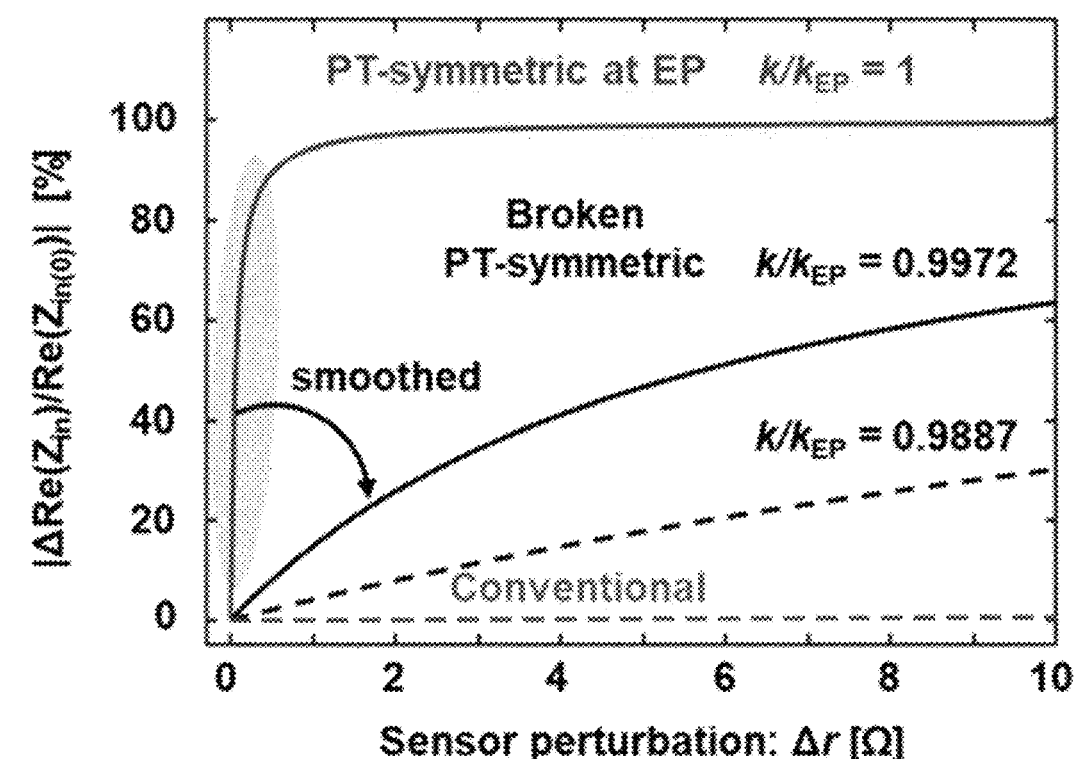
FIG. 22 is a diagram showing a relative rate of change with respect to an initial value of the input impedance real part.

Next, a more detailed numerical analysis is performed on changes in $|\text{Re}(Z_{in})|$, with respect to Δr. FIG. 22 is a diagram showing a relative rate of change $|\Delta\text{Re}(Z_{in})/\text{Re}(Z_{in(0)})|$ with respect to the initial value ($\text{Re}(Z_{in(0)})$) of the input impedance real part, which is a result of simulating an amplitude modulation index with respect to the amount of resistance change (Δr) on the sensor side.

Here, the resistance change occurring on the sensor side is defined as $\Delta r = R_{2(i)} - R_{2(0)}|$. In addition, the initial resistance of the sensor was set to $R_{2(0)} = 1$ (kΩ). At this time, the system configuration and parameters used in each numerical analysis are as follows.

PT-symmetric at EP (gain-loss coupling, $k/k_{EP} = 1$), Broken PT-symmetric (gain-loss coupling, $k/k_{EP} = 0.9972$, $k/k_{EP} = 0.9887$), Conventional (loss-loss coupling, $k/k_{EP} = 1$) First, regarding the PT symmetric coupling system ($k/k_{EP} = 1$, gray solid line) that achieves EP, it can be seen that the relative rate of change of the input impedance real part increases abruptly in the range where Δr changes from 0 to 0.5 (Ω) (gray shaded portion).

However, after that, it can be seen that the increasing tendency of the rate of change is exponentially attenuated and converges to $|\Delta\text{Re}(Z_{in})/\text{Re}(Z_{in(0)})| = 100(\%)$.

From this result, it was found that a nearly infinite change in the input impedance real part (amplitude modulation index) can be obtained only when the amount of resistance change (Δr) on the sensor side is weak on the EP. As described above, this represents the transition from the state where the balance between gain and loss is maintained on the reader side and the sensor side (EP) to the collapse of the balance between gain and loss, and means that the rate of change is particularly remarkable near the EP.

Next, the PT symmetry in the Broken region is considered. As described in FIGS. 3 and 4, the magnetic resonant coupling system satisfying PT symmetry can be divided into the Broken-PT region and the Exact-PT region according to the value of the coupling coefficient (k). Therefore, two types of Broken-PT ($k/k_{EP} = 0.9972$ (black solid line), $k/k_{EP} = 0.9887$ (black dotted line)) were set as EP comparison targets, and a simulation was performed. As a result, it was found that the rate of change of the input impedance real part in the Broken-PT showed a moderate increase compared with that in the case of EP, and that the tendency was attenuated as the $k/k_{EP}$ decreased. In particular, when $k/k_{EP}$=0.9887, the rate of change of the system shows a nearly linear increasing tendency. On the other hand, when $\Delta r$ changes from 0 to 0.5 ($\Omega$), it can be seen that the rate of change of the input impedance real part is reduced because $| \Delta Re(Z_{in})/Re(Z_{in(0)})|$=2.1(%).

Here, even in the existing coupling system (conventional, gray dotted line), a linear rate of change with an increase in glucose concentration is obtained, but when $\Delta r$ changes from 0 to 0.5 ($\Omega$), it can be said that the input impedance real part hardly changes because $\Delta Re(Z_{in})/Re(Z_{in(0)})|$=0.02(%). This means that the amplitude modulation index is close to 0 with respect to the amount of resistance change ($\Delta r$) on the sensor side.

From the simulation results described above, it was found that by introducing PT symmetry into a magnetic coupling system using an LCR parallel resonant circuit, the degree of amplitude modulation index can be improved and adjusted according to the resistance change on the sensor side. In particular, in the Broken-PT system, linear amplitude modulation (AM) is possible with respect to the resistance change on the sensor side, and even if the resistance change on the sensor side is weak, the reader side can obtain an amplified index of modulation. By utilizing this characteristic, it is possible to improve the sensitivity of an LCR resonator type sensor that exerts a weak resistance change in response to bio-signals or environmental changes.

On the other hand, the present invention can be applied not only to an analog modulation scheme but also to a digital modulation scheme. For example, in a propagation method using binary information ("0: small amplitude" or "1: large amplitude") such as amplitude shift keying (ASK), by applying the specific amplitude change near the EP, it is possible to generate binary information indicating almost 100% amplitude modulation index for weak load resistance changes.

(Resonant Circuit-Equipped Bipolar Electrochemical Measurement Device and Glucose Measurement)

A device that converts chemical changes in target biological substances into electrical signals and quantifies them is called a bio-sensor. Among them, bio-sensors using enzymes are expected to be applied in the medical field because they can be composed of bio-derived materials and have substrate specificity to selectively catalyze only specific chemical reactions.

In the present example, a resonant circuit-equipped bipolar electrochemical measurement device was constructed by combining a variable resistance sensor element having a fiber modifying an enzyme (enzyme-modified fiber) and a wireless power supply element. For the detailed configuration of this enzyme-modified fiber, reference can be made to the carbon nanotube film described in International Publication WO2012-002290.

By applying the electrochemical characteristic change due to the enzymatic reaction (glucose oxidase: GOD), it is possible to create a variable chemical resistor that depends on the glucose concentration. In the present example, a bio-sensor that achieves wireless sensing of tear glucose was actually produced by combining this chemical resistor and an LC resonant circuit.

The correlation between the blood glucose level and the sugar content in tears in clinical trials has been proven in publicly known studies (Non-Patent Documents 3, 9, and 29), and the average value of glucose concentration in tears is reported to be 0.16±0.03 (mM) in healthy subjects and 0.35±0.04 (mM) in patients with diabetes.

In addition, the variation range in the glucose tolerance test is 0.10 to 0.30 (mM) in healthy subjects and 0.15 to 0.60 (mM) in patients with diabetes.

This minute variation in the concentration of glucose in tears is determined to be read.

In the present example, a battery was constructed using a GOD enzyme-modified fiber and a silver-silver chloride electrode (Ag/AgCl), and the value indicated by the sensor is defined as the resistance value resulting from the current value obtained on the enzyme-modified fiber when a potential is applied to both electrodes.

Here, the mechanism is that, when the glucose concentration in the solution is changed while a constant potential is applied, the electron-accepting performance of the enzyme-modified fiber changes depending on the reaction specificity, resulting in a change in the resistance value of the sensor.

Figure 23:
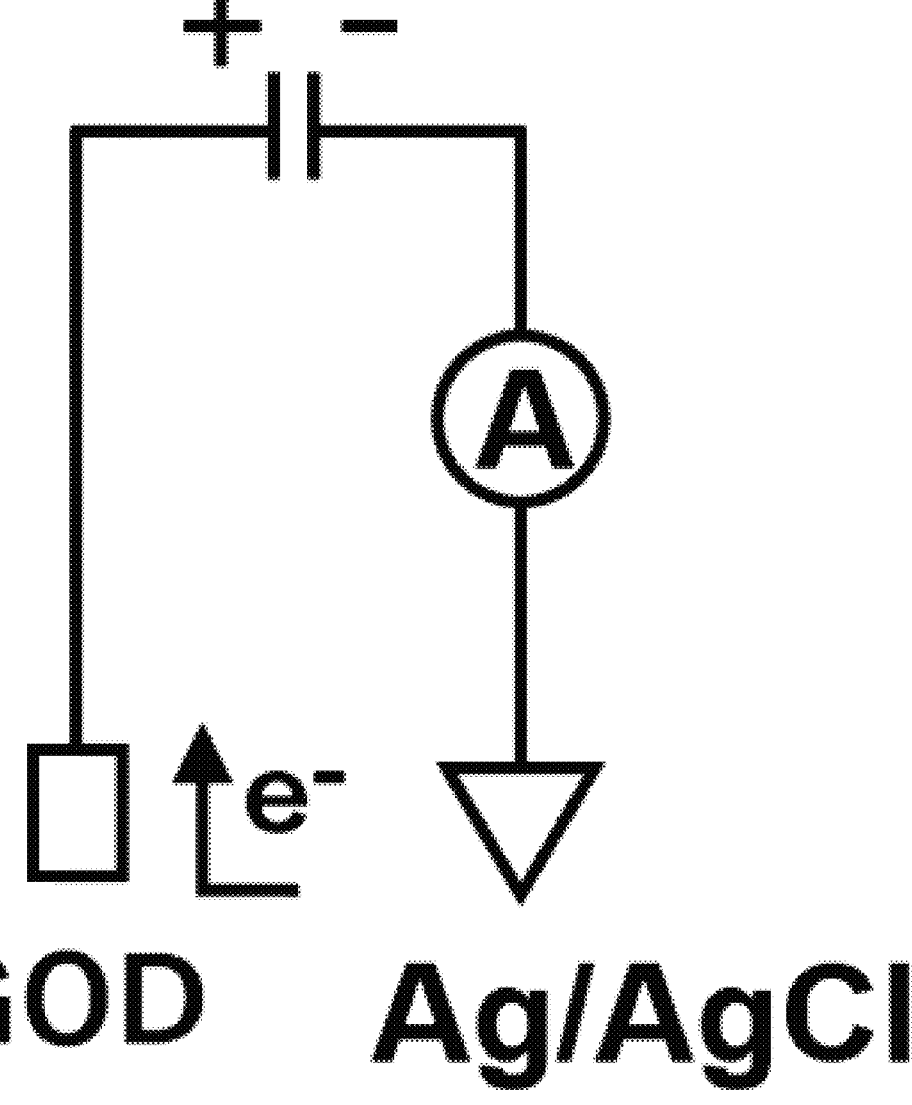
FIG. 23 is a block diagram showing an overview of reaction specificity evaluation by amperometry.
Figure 24:
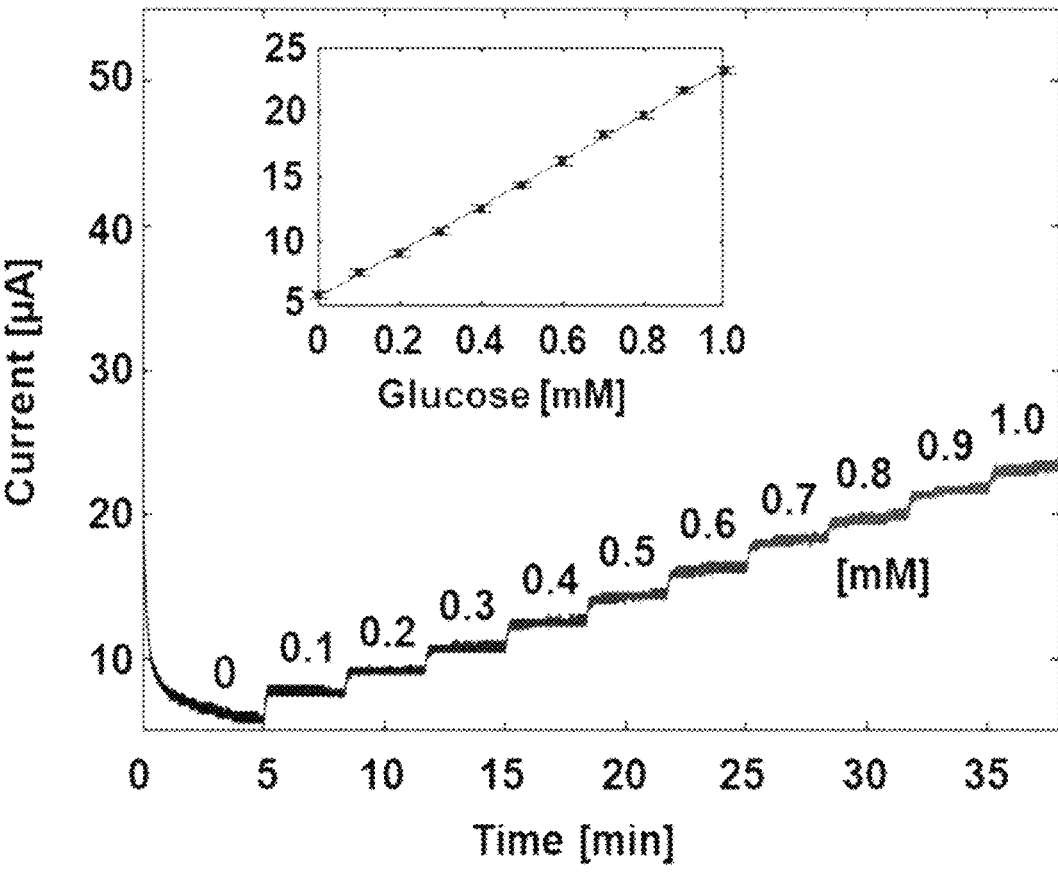
FIG. 24 is an inset showing results of calculating an average value and standard deviation (100 seconds) of currents at each concentration.

In fact, when the glucose concentration of artificial tears was changed from 0.0 to 1.0 (mM), how the power generation performance changes between the GOD enzyme-modified fiber and Ag/AgCl was measured by amperometry (FIG. 23). FIG. 24 is an inset showing results of calculating an average value and standard deviation (100 seconds) of currents at each concentration. Based on these results, the average values of current at each concentration were as follows.

5.89 ($\mu$A): 0 (mM), 7.64 ($\mu$A): 0.1 (mM), 9.12 ($\mu$A): 0.2 (mM), 10.75 ($\mu$A): 0.3 (mM), 12.50 ($\mu$A): 0.4 (mM), 14.33 ($\mu$A): 0.5 (mM), 16.24 ($\mu$A): 0.6 (mM), 18.22 ($\mu$A): 0.7 (mM), 19.76 ($\mu$A): 0.8 (mM), 21.68 ($\mu$A): 0.9 (mM), 23.21 ($\mu$A): 1.0 (mM)

Figure 25:
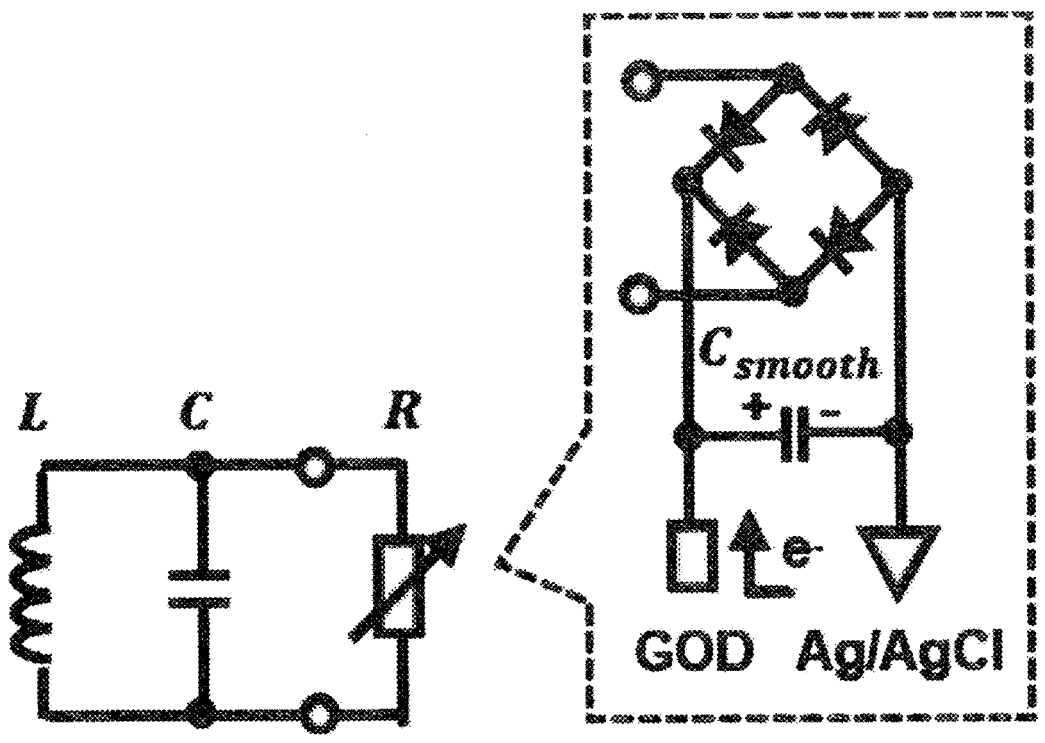
FIG. 25 is an equivalent circuit diagram of a resonant circuit-equipped bipolar electrochemical measurement device.

From the above, it was found that the GOD electrode has a sensor sensitivity of 1.57 ($\mu$A)/0.1 (mM) with respect to changes in glucose concentration, showing a linear increase in the range of 0 to 1.0 (mM). This change in oxidation current can be regarded as a change in resistance value, and can be treated as a variable resistor R connected in parallel with the LC resonant circuit (FIG. 25).

At this time, the change in R affects the value of the impedance real part component when the LCR parallel resonant circuit resonates. Therefore, amplitude modulation (AM) caused by the glucose concentration becomes possible. FIG. 26 shows a schematic diagram of an actually created resonant circuit-equipped bipolar electrochemical measurement device.

A full-wave rectifier circuit is configured with a bridge diode (BAS4002A-RPP), a diode capacitance $C_{diode}$=2 to 5 (pF), and a smoothing capacitor $C_{smooth}$=22 ($\mu$F). The DC voltage applied between the GOD enzyme-modified fiber and Ag/AgCl is obtained by rectifying the AC voltage taken from a resonant capacitor C.

Figure 27:
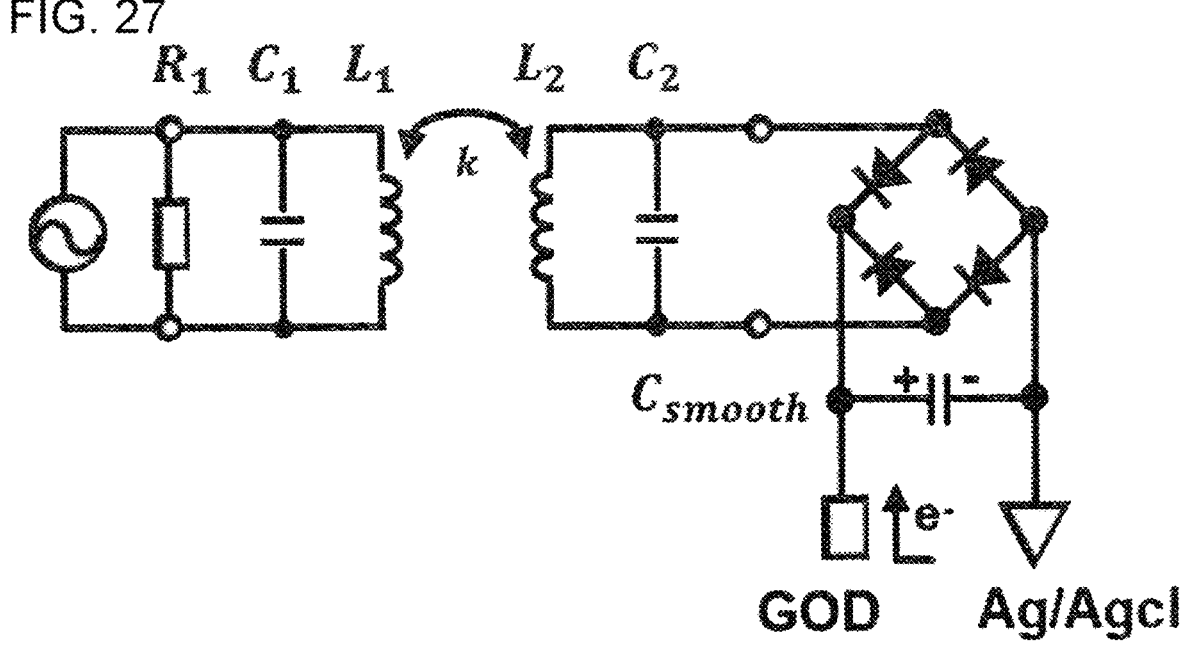
FIG. 27 is a schematic diagram of a wireless power transmission system using frequency sweep.

A specific rectification method is implemented by full-wave rectification by a bridge diode connected in parallel with a resonant capacitor and smoothing by a capacitor $C_{smooth}$. That is, the AC voltage is full-wave rectified by a bridge diode connected in parallel, and can be treated as a DC voltage source by a smoothing capacitor $C_{smooth}$. The high-frequency magnetic field generated from the primary resonant circuit is defined by the frequency sweep of the network analyzer, and exhibits the highest power transmission efficiency when the excitation frequency and the natural frequency of the resonant circuit match (FIG. 27).

Figure 28:
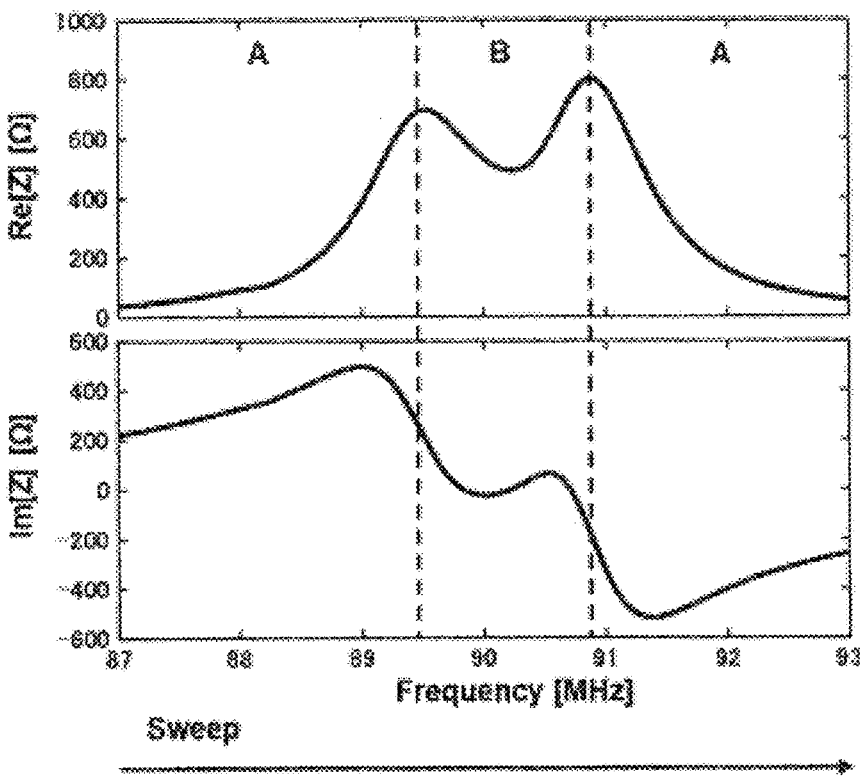
FIG. 28 is a graph showing changes in DC voltage on a smoothing capacitor due to frequency sweep.
Figure 28:
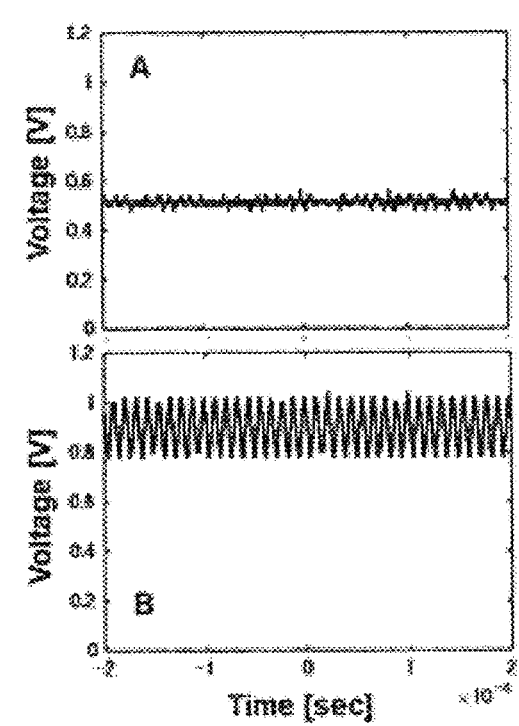

For example, in a region (A) away from the resonance frequency, the voltage obtained at both ends of the smoothing capacitor remains at about 0.5 (V), whereas in a region (B) near the resonance frequency, the desired DC voltage is obtained (FIG. 28).

As described above, the bio-sensor according to the present invention has a mechanism in which the resistance value changes by applying a DC voltage between the GOD enzyme-modified fiber and Ag/AgCl near the resonance frequency to promote an electrochemical reaction.

Figure 29:
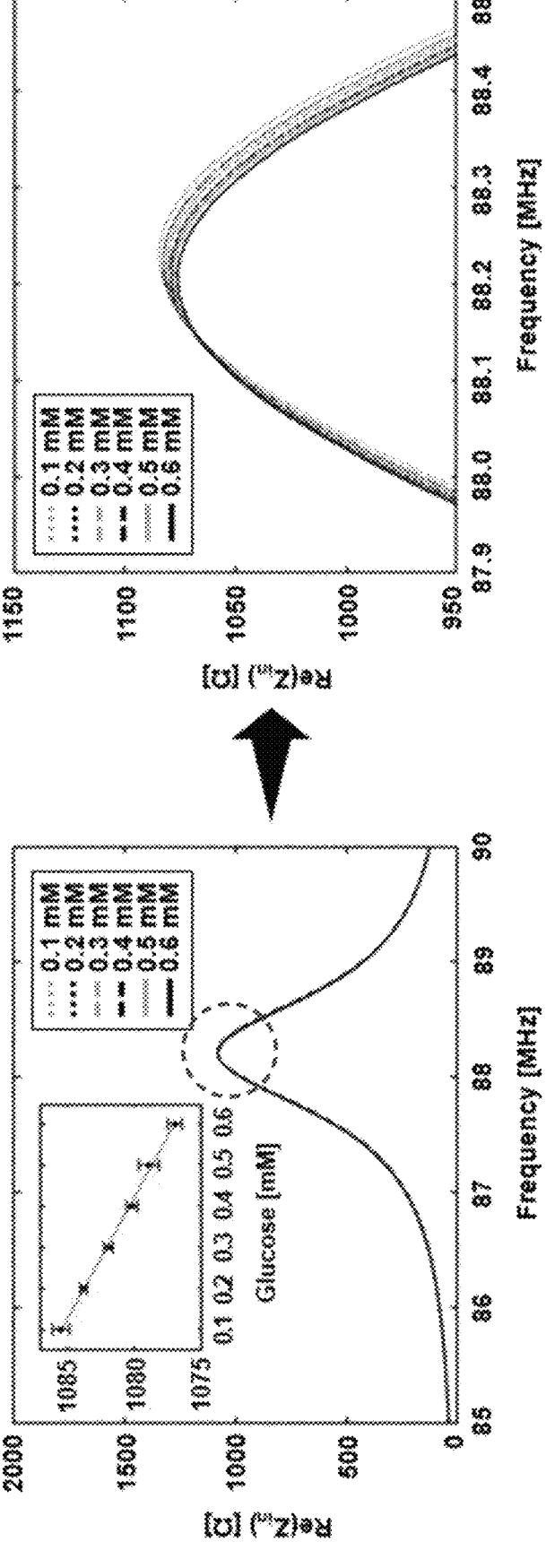
FIG. 29 is a diagram showing an input impedance real part component of a glucose sensor and showing measurement results (average values for five frequency sweeps) when the glucose concentration was changed from 0.1 to 0.6 (mM).

FIG. 29 is a diagram showing an input impedance real part component ($Re(Z_{in})$) of a glucose sensor and showing measurement results (average values for five frequency sweeps) when the glucose concentration was changed from 0.1 to 0.6 (mM). The upper (right) diagram of FIG. 29 is an enlarged view of the vicinity of the peak (dotted circle frame portion) of the impedance real part component ($Re(Z_{in})$) in the lower (left) diagram of FIG. 29.

Further, the results of plotting $Re(Z_{in})$ at resonance at each concentration are shown in an inset (average value and standard deviation for five frequency sweeps). Here, the average value of $Re(Z_{in})$ with each concentration change was as follows.

1085 ($\Omega$): 0.1 (mM), 1084 ($\Omega$): 0.2 (mM), 1082 ($\Omega$): 0.3 (mM), 1080 ($\Omega$): 0.4 (mM), 1079 ($\Omega$): 0.5 (mM), 1077 ($\Omega$): 0.6 (mM)

This means an increase in oxidation current, that is, a decrease in chemical resistance value, with an increase in glucose concentration, and the sensor sensitivity is 1.6 ($\Omega$)/0.1 (mM).

(Wireless Glucose Sensing in PT Symmetry-Conserved Region)

Figure 30:
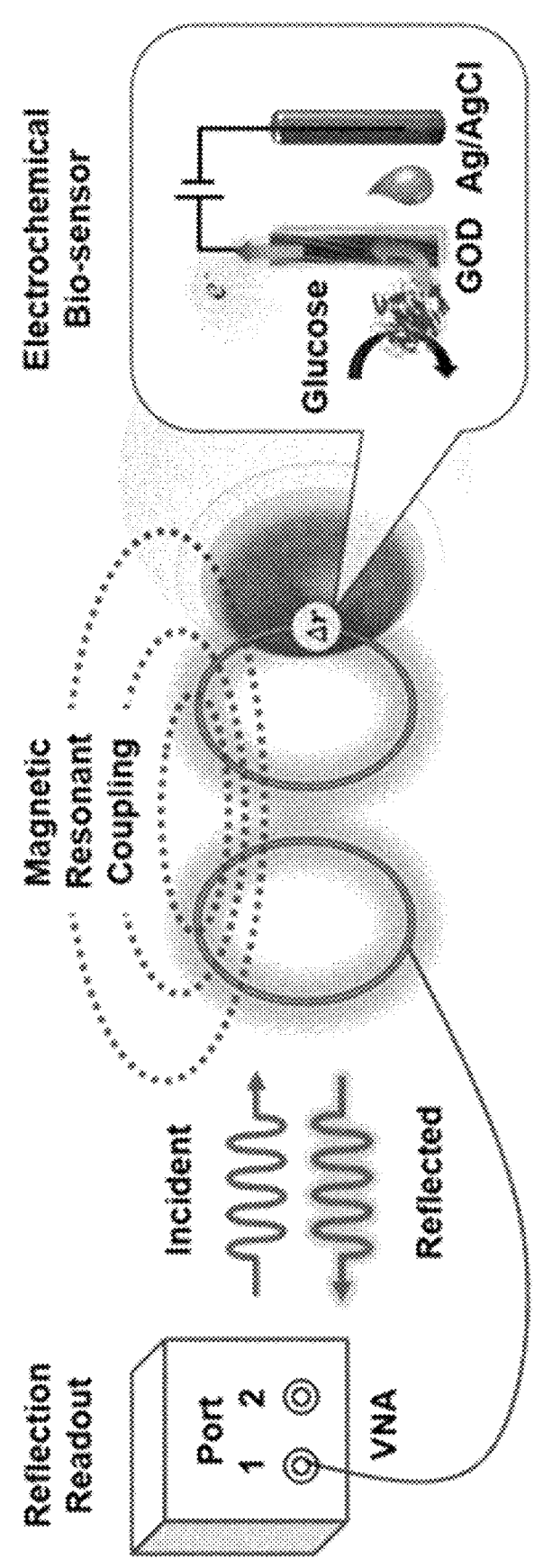
FIG. 30 is a conceptual diagram of highly sensitive bio-sensing using a PT symmetry-conserved region in a magnetic resonant coupling system.

A conceptual diagram of highly sensitive bio-sensing using a PT symmetry-conserved region in a magnetic resonant coupling system is shown (FIG. 30).

First, a contact lens-type bio-sensor is produced by including the bio-sensor described above in a PDMS contact lens.

The tear glucose obtained on the surface of the eyeball is then utilized to induce load modulation of the loss resonant circuit.

Finally, the idea is to read the resistance value change with high sensitivity on the gain resonant circuit side through magnetic resonant coupling in which PT symmetry is conserved. Here, the results of wirelessly measuring changes in glucose concentration in artificial tears using the experimental environment of FIG. 30 are shown.

The magnetic resonant coupling system shown in FIG. 30 was constructed experimentally, and the input impedance ($Z_{in}$) in loss-loss coupling was measured. The transmission distance between the reader and the sensor was set to 14.9 (mm), a loss resonator was used as the reader, and a resonant circuit-equipped bipolar electrochemical measurement device equipped with a GOD electrode was used as the sensor.

Figure 31:
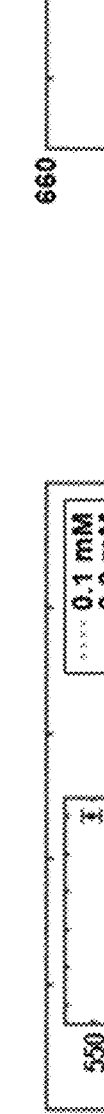
FIG. 31 is a diagram showing results (average values for five frequency sweeps) when the glucose concentration was changed from 0.1 to 0.6 (mM).
Figure 31:
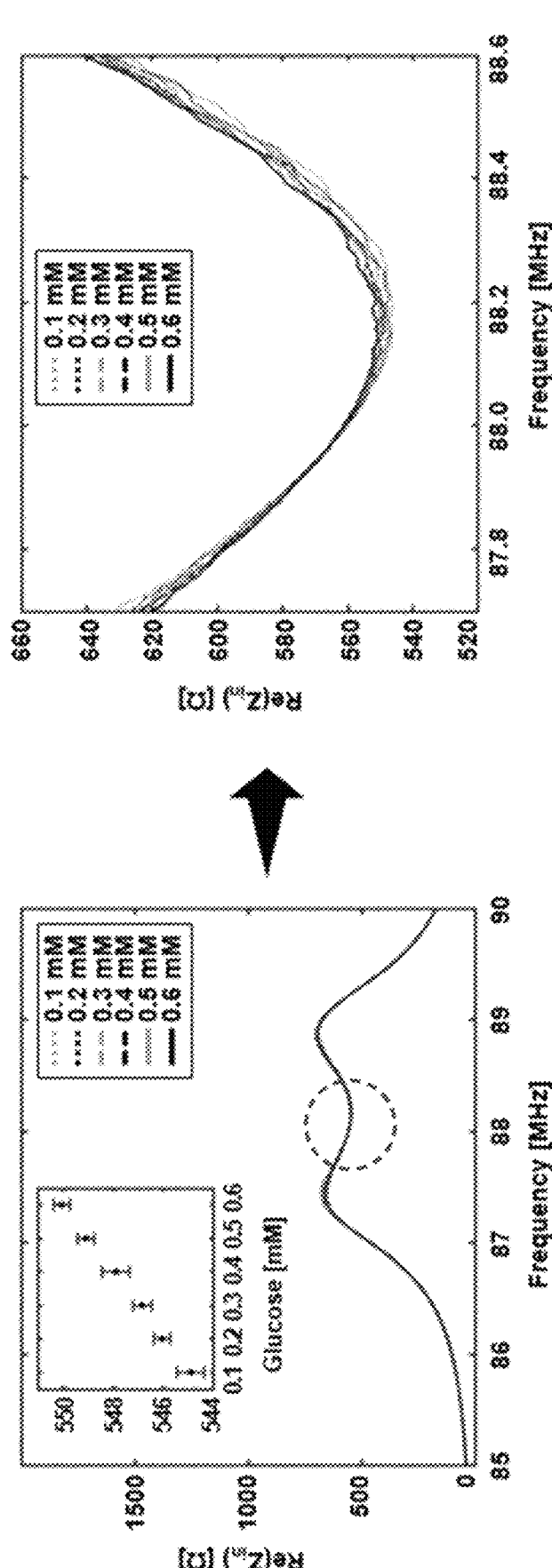

FIG. 31 is a diagram showing results of measuring the input impedance real part component ($Re(Z_{in})$) with the above settings. The upper (right) diagram of FIG. 31 is an enlarged view of the vicinity of 88 (MHz) (dotted circle frame portion) of the impedance real part component (Re ($Z_{in}$)) in the lower (left) diagram of FIG. 31. FIG. 31 shows results (average values for five frequency sweeps) when the glucose concentration was changed from 0.1 (mM) to 0.6 (mM).

FIG. 31 also shows the results of plotting $Re(Z_{in})$ at resonance at each concentration as an inset (average value and standard deviation for five frequency sweeps). Here, the average value of $Re(Z_{in})$ with each concentration change was as follows.

545 ($\Omega$): 0.1 (mM), 546 ($\Omega$): 0.2 (mM), 547 ($\Omega$): 0.3 (mM), 548 ($\Omega$): 0.4 (mM), 549 ($\Omega$): 0.5 (mM), 550 ($\Omega$): 0.6 (mM).

The results demonstrate that changes in the chemical resistor generated on the sensor side can be read on the reader side through magnetic resonant coupling. In addition, the sensor sensitivity was 1.0 ($\Omega$)/0.1 (mM).

Figure 32:
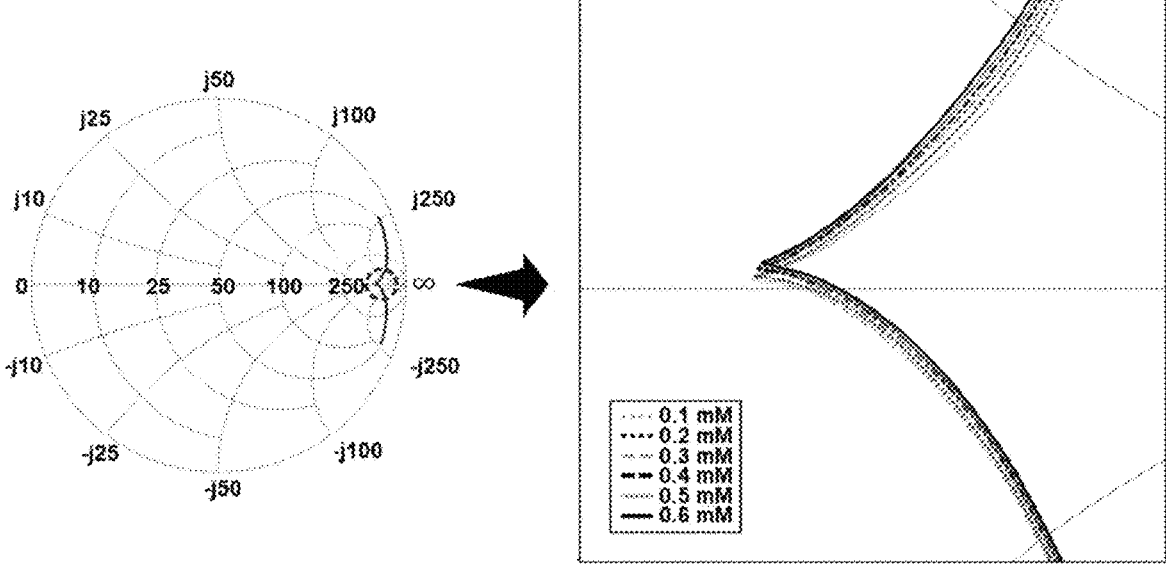
FIG. 32 plots this frequency characteristic on a Smith chart.

FIG. 32 plots this frequency characteristic on a Smith chart, and the right diagram of FIG. 32 shows an enlarged view of the vicinity of the resonance point (dotted circle frame portion). From this result, it can be said that through magnetic resonant coupling between the reader and the glucose sensor, the glucose concentration detected by the sensor can be wirelessly measured as amplitude modulation.

Next, the input impedance ($Z_{in}$) in the gain-loss coupling was measured. The transmission distance between the reader and the sensor was set to 14.9 (mm), a gain resonator was used as the reader, and a resonant circuit-equipped bipolar electrochemical measurement device equipped with a GOD electrode was used as the sensor.

Figure 33:
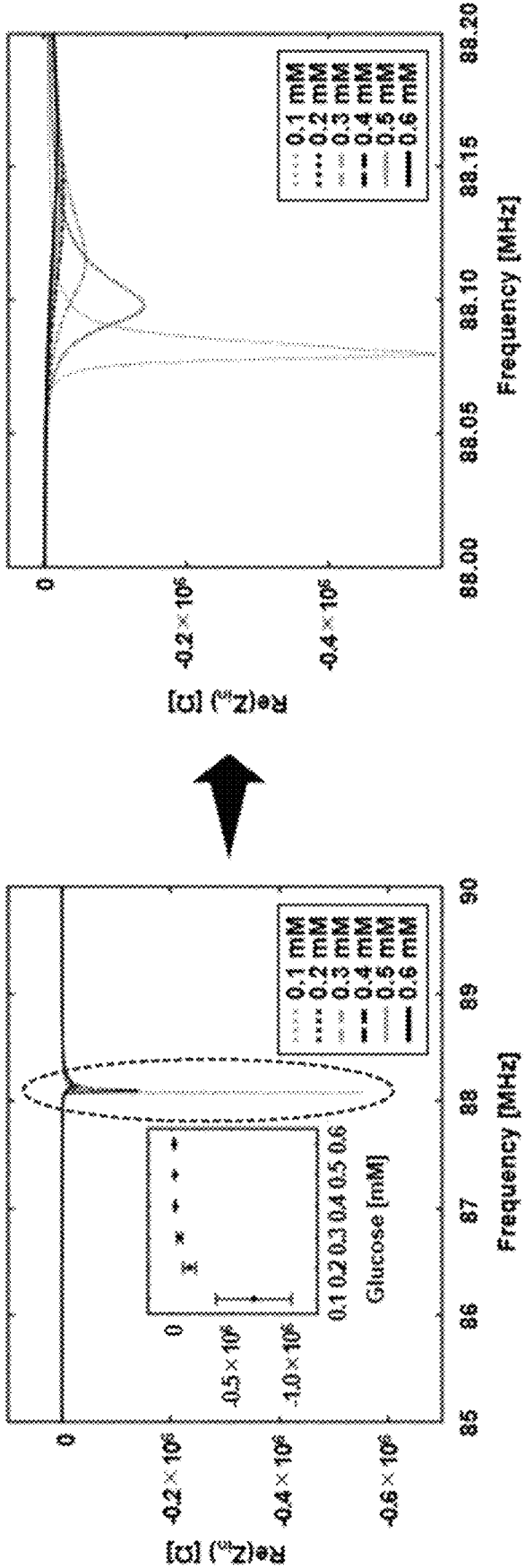
FIG. 33 shows (average values for five frequency sweeps) when the glucose concentration was changed from 0.1 to 0.6 (mM).

A strict EP was achieved by adjusting the distance between the resonators while checking the impedance characteristics on a network analyzer. FIG. 33 shows experimental results when a gain resonator is used as a reader and PT symmetry (EP) is satisfied.

FIG. 33 shows $Re(Z_{in})$ (average values for five frequency sweeps) when the glucose concentration was changed from 0.1 to 0.6 (mM). The upper (right) diagram of FIG. 33 is an enlarged view of the vicinity of 88 (MHz) (dotted circle frame portion) of the impedance real part component (Re ($Z_{in}$)) in the lower (left) diagram of FIG. 33. Further, in FIG. 33, the results of plotting $Re(Z_{in})$ at resonance at each concentration are shown in an inset (average value and standard deviation for five frequency sweeps). Here, the average value of $Re(Z_{in})$ with each concentration change was as follows.

−77.5 (k$\Omega$): 0.1 (mM), −145.8 (k$\Omega$): 0.2 (mM), −61.2 (k$\Omega$): 0.3 (mM), −28.3 (k$\Omega$): 0.4 (mM), −24.8 (k$\Omega$): 0.5 (mM), −19.4 (k$\Omega$): 0.6 (mM)

As compared with FIG. 31, it can be seen that the frequency characteristics of the input impedance real part are narrowed, which shows a very sharp peak value. In particular, the value of $Re(Z_{in})$ at 0.1 (mM) is as large as −677.5 (k$\Omega$), which is considered to have reached the EP.

Therefore, it can be said that the coupling system exhibits almost no loss ($Z_{in} \approx \infty$) and a high Q value at this initial value.

Figure 34:
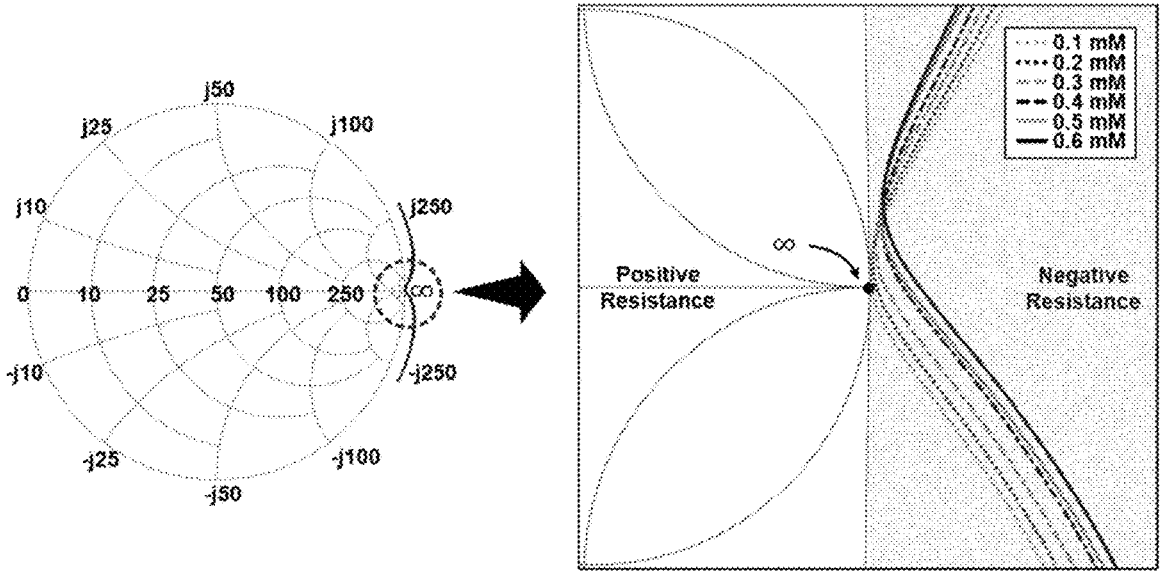
FIG. 34 plots this frequency characteristic on a Smith chart.

FIG. 34 plots this frequency characteristic on a Smith chart, and the right diagram of FIG. 34 shows an enlarged view of the vicinity of OPEN ($Re(Z_{in})=\infty$) (dotted circle frame portion of the left diagram of FIG. 34). It can be seen that the trajectory of the reflection coefficient is located OPEN at the resonance point when the glucose concentration is the initial value (0.1 mM).

Further, it can be seen that, as the glucose concentration increases, this trajectory shifts to the upper right, and the resonance point moves away from OPEN. In conventional dissipative systems including loss resonators, the reflection coefficient is never located OPEN, making it impossible to implement a lossless coupling system. However, using the concept of PT symmetry makes it possible to make the coupling system lossless at the resonance frequency.

In addition, from the inset in FIG. 33, it can be seen that the rate of change of $Re(Z_{in})$ specifically increases when the glucose concentration changes from 0.1 to 0.2 (mM). On the other hand, in the range of 0.2 (mM) to 0.6 (mM), it can be confirmed that the rate of change gradually becomes slow. This means a remarkable rate of change of $Re(Z_{in})$ near the EP.

On the other hand, it can be seen that when the glucose concentration is 0.1 (mM), the error bar of $Re(Z_{in})$ is relatively large. This indicates that the numerical variation (unintended error) in the Clapp oscillation circuit and the chemical resistor produced as examples of the present invention was amplified at the EP, and in other words, it can be said that the system sensitivity is very large near the EP. Assuming that this numerical variation is periodic noise emitted from the measuring instrument, it is possible to extract the true value using multiple measurement results (frequency sweeps).

On the other hand, a gain resonator was used as the reader, and a wireless measurement experiment was conducted when PT symmetry (on the Broken-PT region) was satisfied. Here, the distance between the resonators (reader/sensor) was set to about 15.0 (mm). This is because the coupling coefficient is set to be $k_{EP}$ or less ($k/k_{EP}<1$). A strict Broken-PT was achieved by adjusting the distance between the resonators while checking the impedance characteristics on a network analyzer.

Figure 35:
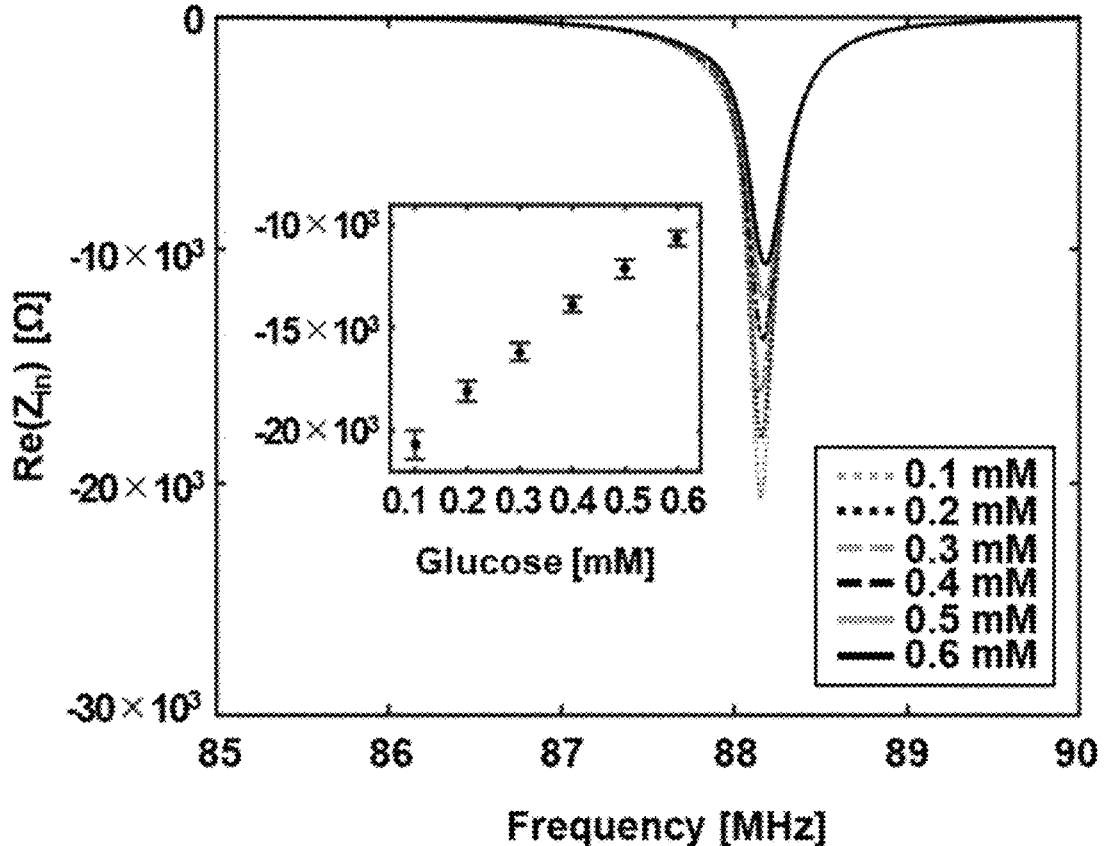
FIG. 35 shows (average values for five frequency sweeps) when the glucose concentration was changed from 0.1 to 0.6 (mM).

FIG. 35 shows $Re(Z_{in})$ (average value for five frequency sweeps) when the glucose concentration is changed from 0.1 to 0.6 (mM), in FIG. 35, $Re(Z_{in})$ at resonance at each concentration is shown as an inset (average value and standard deviation for five frequency sweeps). Here, the average value of $Re(Z_{in})$ with each concentration change was as follows.

−20.7 (kΩ): 0.1 (mM), −18.1 (kΩ): 0.2 (mM), −16.1 (kΩ): 0.3 (mM), −13.9 (kΩ): 0.4 (mM), −12.1 (kΩ): 0.5 (mM), −10.6 (kΩ): 0.6 (mM)

Thus, it can be seen that the value of $Re(Z_{in})$ at 0.1 (mM) decreased from −677.5 (kΩ) to −20.7 (kΩ) compared with the case of PT symmetry (EP). That is, it can be said that the reflection coefficient at resonance is moving away from OPEN ($Re(Z_{in})=\infty$). On the other hand, it shows a linear amplitude change with respect to an increase in glucose concentration, and it can be confirmed that the sensor sensitivity is about 2000 times higher than that of the existing coupling system (sensor sensitivity: 2 (kΩ)/0.1 (mM).

Figure 36:
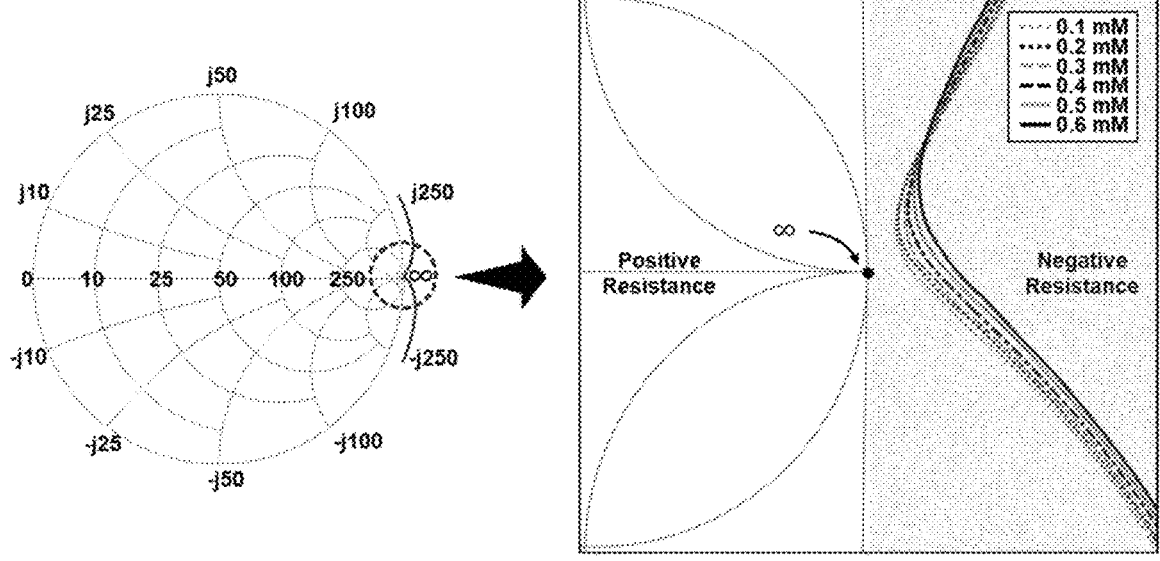
FIG. 36 plots this frequency characteristic on a Smith chart.

FIG. 36 plots this frequency characteristic on a Smith chart, and the right diagram of FIG. 36 shows an enlarged view of the vicinity of OPEN ($Re(Z_{in})=\infty$) (dotted circle frame portion of the left diagram of FIG. 36). From this result, it was found that improved sensor sensitivity and linear response can be achieved in wireless measurement using Broken-PT.

Figure 37:
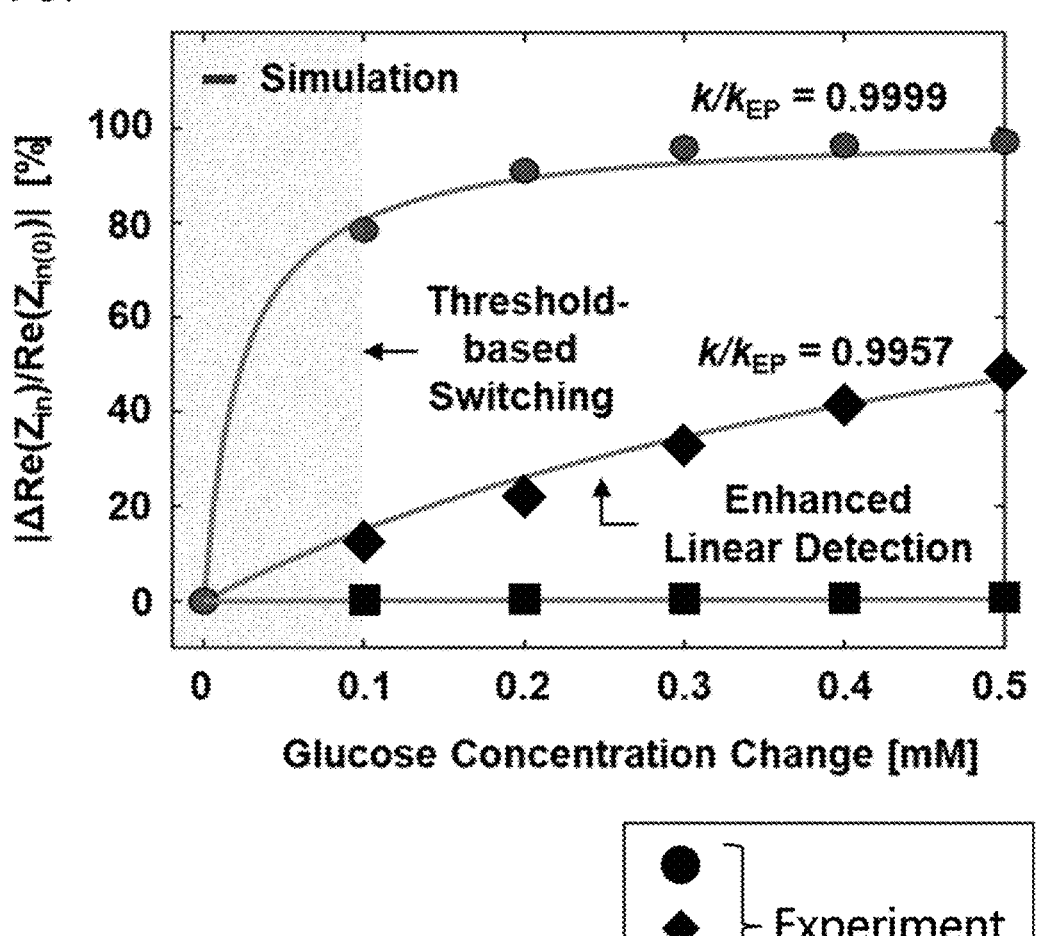
FIG. 37 is a graph comparing these experimental results from the viewpoint of an amplitude modulation index.

FIG. 37 is a graph comparing these experimental results from the viewpoint of an amplitude modulation index. FIG. 37 is a diagram showing a relative rate of change ($|\Delta Re(Z_{in})/Re(Z_{in(0)})|$) with respect to the initial value ($Re(Z_{in(0)})$) of the input impedance real part, showing an amplitude modulation index corresponding to changes in glucose concentration. Circle marks, diamond marks, and square marks represent measured values (average values of $Re(Z_{in})$ for five frequency sweeps), and gray solid lines represent curve fitting (applying the simulation results of FIG. 22). At this time, the coupling system that satisfies the EP is plotted as circle marks, the coupling system in Broken-PT is plotted as diamond marks, and the existing loss-loss coupling system is plotted as square marks.

From this drawing, it can be seen that the relative rate of change (amplitude modulation index) of the input impedance real part is dramatically improved in the coupling system that satisfies the PT symmetry as compared with the existing loss-loss coupling system. In particular, in the coupling system that satisfies the EP, a specific change in the input impedance real part can be confirmed in response to a weak change in glucose concentration ($\Delta r=0.1$ mM), and the increasing tendency is infinite ($|\Delta Re(Z_{in})/Re(Z_{in(0)})|=78.47$ (%).

This is a significant rate of change compared with the existing loss-loss system ($|\Delta Re(Z_{in})/Re(Z_{in(0)})|=0.19(\%)$). After that, it can be seen that the relative rate of change (amplitude modulation index) of the input impedance real part converges at $\Delta r=0.2$ to 0.5 mM.

On the other hand, in the coupling system that satisfies the Broken-PT, it can be seen that the input impedance real part shows a linear increasing tendency with respect to changes in glucose concentration. From the above results, it was possible to improve the rate of change (amplitude modulation index) of the input impedance real part by using a magnetic resonant coupling system that satisfies PT symmetry.

Specifically, in contrast to the conventional loss-loss resonant coupling system, which was difficult to read due to the low amplitude modulation index, it is possible to construct a threshold response (EP) with an increase in glucose concentration and a linear response (Broken-PT) with an increase in glucose concentration, and a wireless measurement system with a high degree of amplitude modulation index can be achieved.

(Measurement of Blood Lactate)

Figure 38:
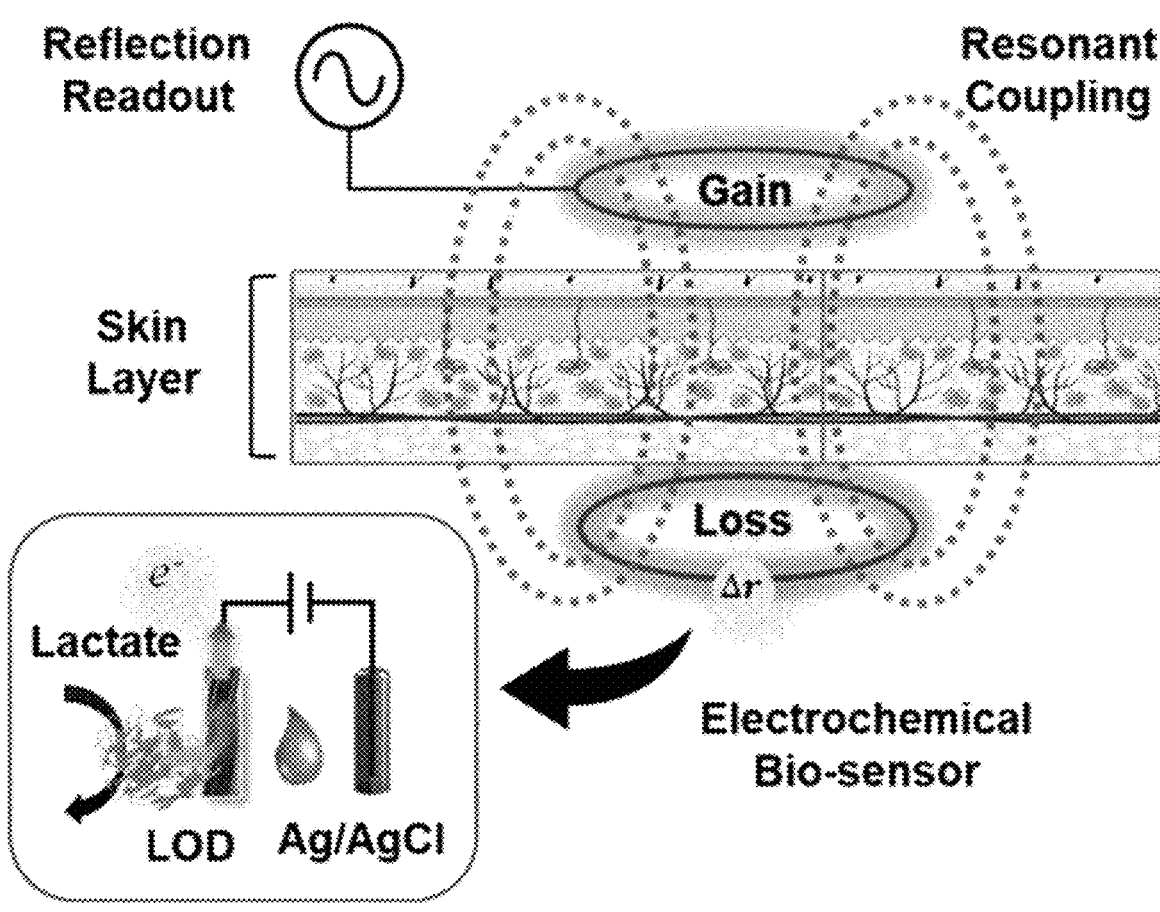
FIG. 38 is a schematic diagram of an experiment for blood lactate concentration measurement.

Aiming to apply a highly sensitive wireless measurement system using PT symmetry to an implantable device, an effective method for measuring blood lactate concentration will be demonstrated. FIG. 38 is a schematic diagram of an experiment for blood lactate concentration measurement, showing a magnetic resonant coupling system via skin tissue.

Here, a gain resonator was used on the reader side, and the above-described resonant circuit-equipped bipolar electrochemical measurement device was used on the sensor side. By using lactate oxidase (LOD) in the enzyme electrode that constitutes this sensor, blood lactate can be wirelessly measured.

Blood lactate is used as a biomarker for sepsis, and there is a report that the fatality rate of patients increases linearly as its concentration exceeds 2.0 (mM) (Non-Patent Document 31). It can be said that for patients suspected of having sepsis, monitoring blood lactate and calling attention when it exceeds the threshold (2.0 (mM)) are important issues for prompt treatment.

Therefore, in the present example, the present invention is applied as a wireless subcutaneous implantable device to wirelessly measure blood lactate concentration (0 to 4.0 (mM)).

Figure 39:
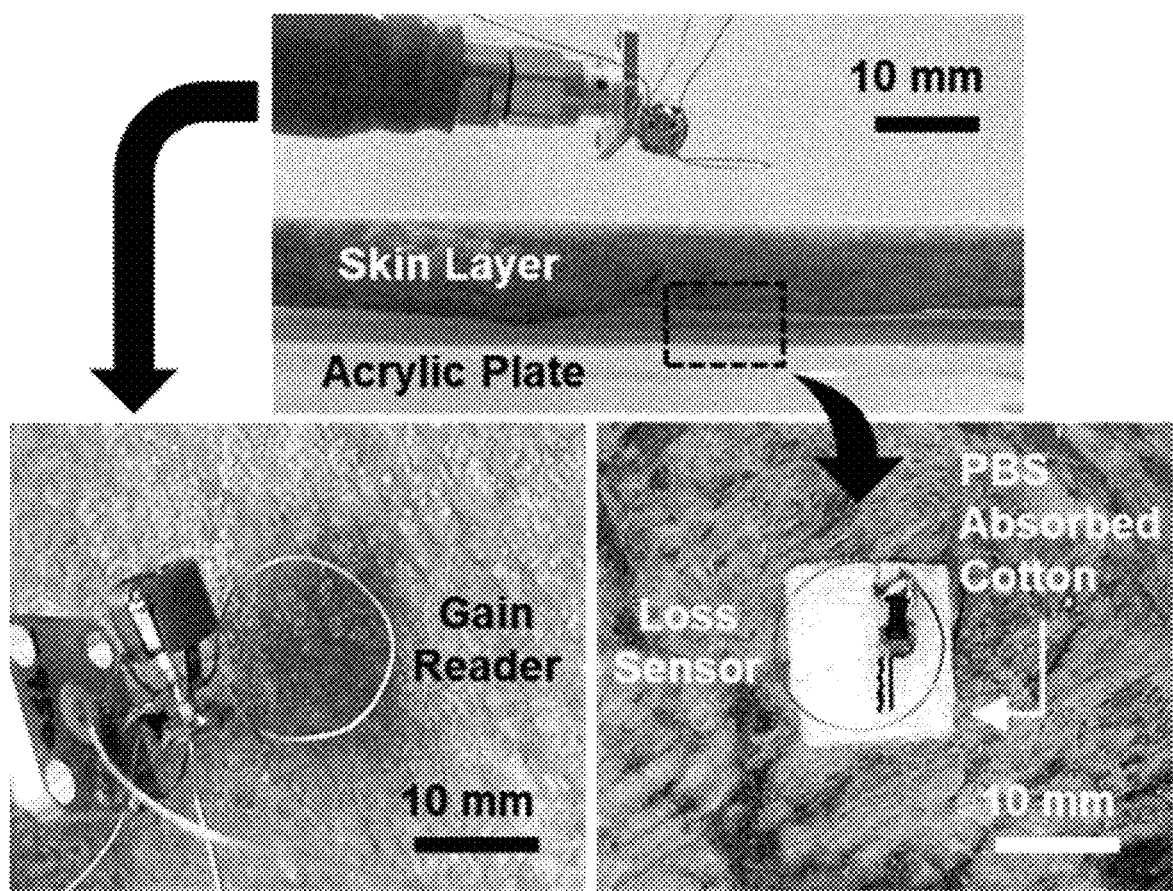
FIG. 39 is a diagram of an actual measurement system for blood lactate.

FIG. 39 is a diagram of an actual measurement system for blood lactate. The skin tissue (thickness 10.5 mm) shown in FIG. 39 was purchased from KAC Co., Ltd. and contains epidermis/dermis/subcutaneous fat. In the wireless measurement experiment, a passive lactate sensor with absorbent cotton was installed on an acrylic plate, and skin tissue was placed on it. At this time, the working electrode (LOD) and the counter electrode (Ag/AgCl) of the passive lactate sensor are connected via a PBS solution (pH=7.0) contained in the absorbent cotton.

In this experiment, it first confirmed how magnetic resonant coupling is affected by the presence or absence of skin tissue.

Figure 40:
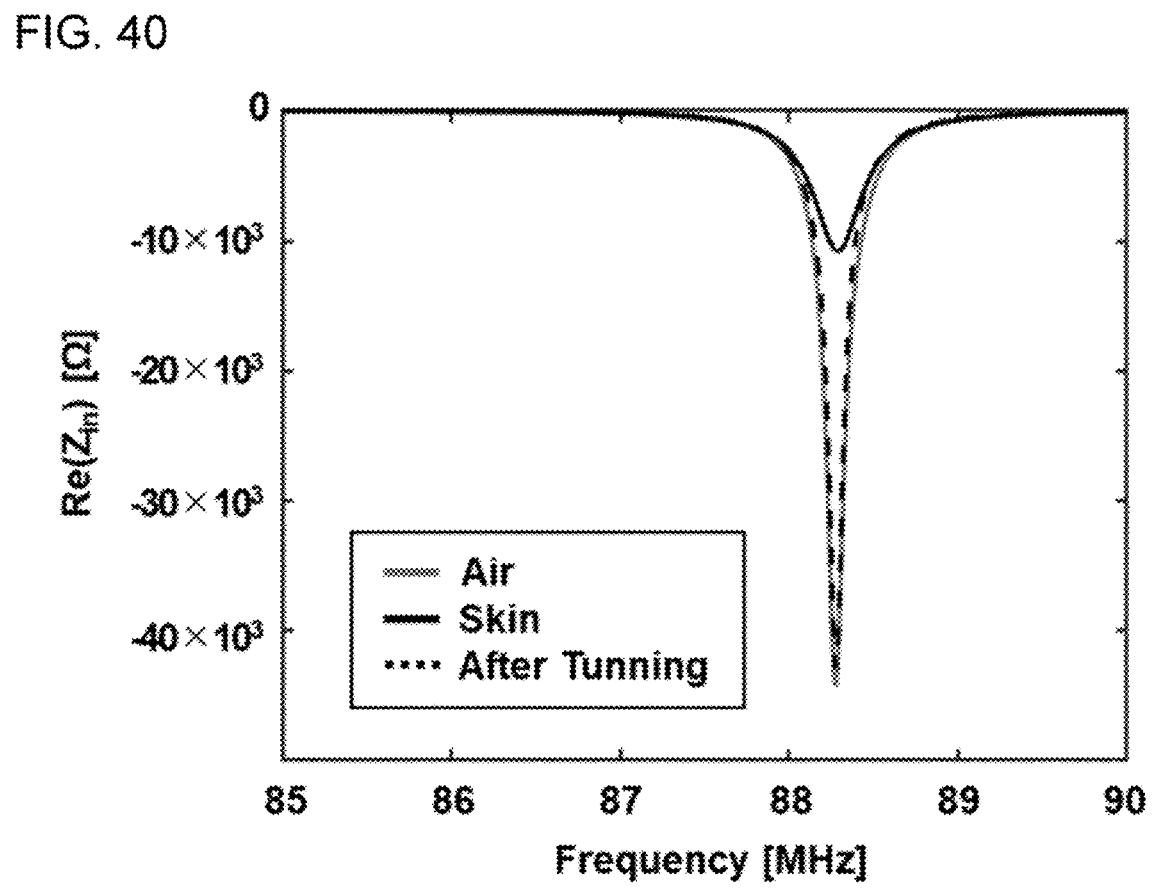

FIG. 40 shows the measured values of the input impedance real part $Re(Z_{in})$ of the magnetic resonant coupling system having PT symmetry, and is a diagram for the purpose of comparison between the case without skin tissue (gray solid line) and the case with skin tissue (black solid line). At this time, since the gain and loss are well balanced and the coupling coefficient is close to $k_{EP}$ in the absence of skin tissue, it can be seen that the coupling system reaches the vicinity of EP ($\text{Re}(Z_{in})$=−44 (kΩ) at resonance).

On the other hand, when skin tissue was inserted between these resonators, the amplitude of the input impedance real part was greatly attenuated ($\text{Re}(Z_{in})$=−11 (kΩ)) at resonance. This is because the skin tissue, which is a dielectric, changed the dielectric constant between the resonators.

It is considered that the magnetic resonant coupling system produced in this experiment performs energy transmission based mainly on the magnetic field, while a unique electromagnetic field is distributed in the vicinity of the resonator (Non-Patent Document 32). Accordingly, dielectric loss is considered to occur when a dielectric exists in the vicinity of the resonator.

However, in the gain resonator produced in this study, the value of the negative resistance can be adjusted appropriately by the applied voltage. By utilizing this function, the EP state can be created again in the magnetic resonant coupling system (black dotted line).

From the above results, in the magnetic resonant coupling system produced in this study, it can be said that PT symmetry (EP) can be constructed even if there is a dielectric (skin tissue) between the resonators, and readjustment of the amplitude modulation index is still possible. By utilizing this characteristic, it is possible to optionally improve the sensor sensitivity during wireless measurement according to the resistance component on the sensor side ($\text{Re}(Z_{in})$ at resonance).

Figure 41:
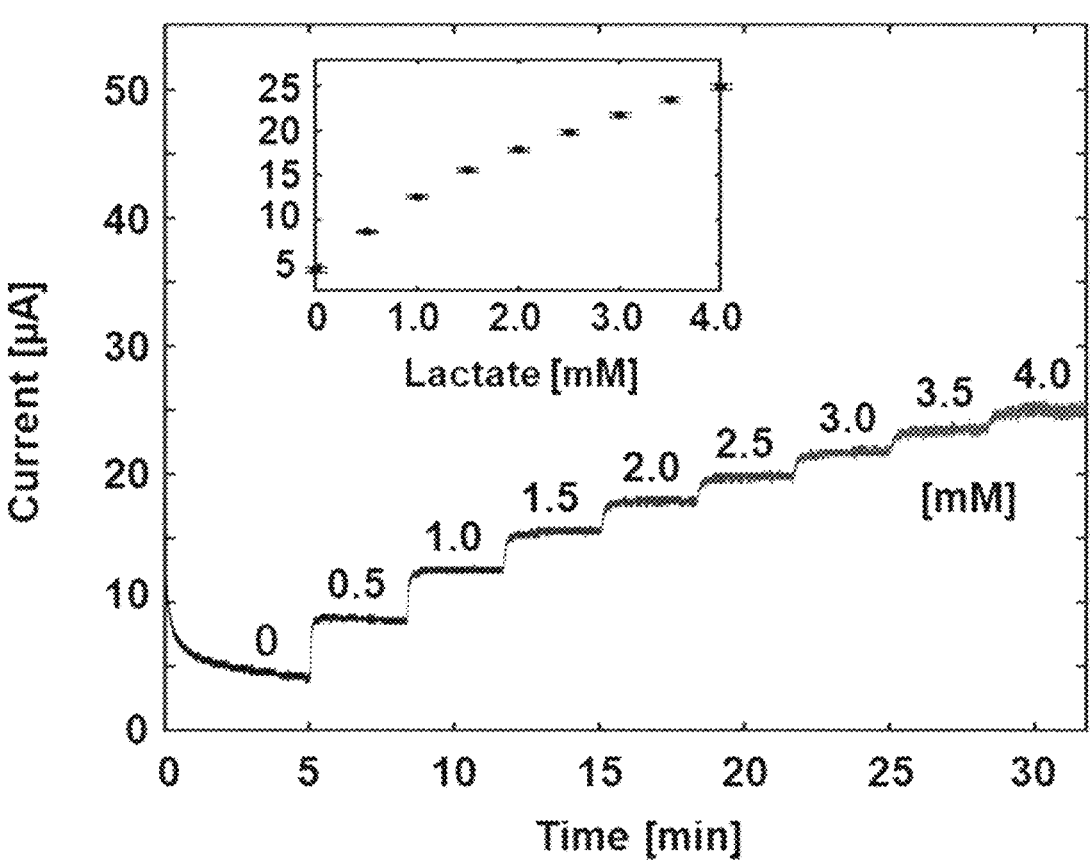
FIG. 41 is a graph showing results of amperometric measurement of how the power generation performance changes between a LOD enzyme-modified fiber and Ag/AgCl when the lactate concentration of PBS was changed from 0.0 to 4.0 (mM).

Finally, high-sensitivity wireless measurement of lactate concentration using a lactate sensor to which a resonant circuit-equipped bipolar electrochemical measurement device is applied will be performed. FIG. 41 is a graph showing results of amperometric measurement of how the power generation performance changes between a LOD enzyme-modified fiber and Ag/AgCl when the lactate concentration of PBS was changed from 0.0 to 4.0 (mM).

At this time, the results of calculating the average value and standard deviation (100 seconds) of the current at each concentration are shown in the inset. Here, the average values of current at each concentration were as follows.

4.36 (µA): 0 (mM); 8.67 (µA): 0.5 (mM), 12.56 (µA): 1.0 (mM), 15.59 (µA): 1.5 (mM), 17.89 (µA): 2.0 (mM), 19.81 (µA): 2.5 (mM), 21.77 (µA): 3.0 (mM), 23.48 (µA): 3.5 (mM), 24.96 (µA): 4.0 (mM)

Figure 42:
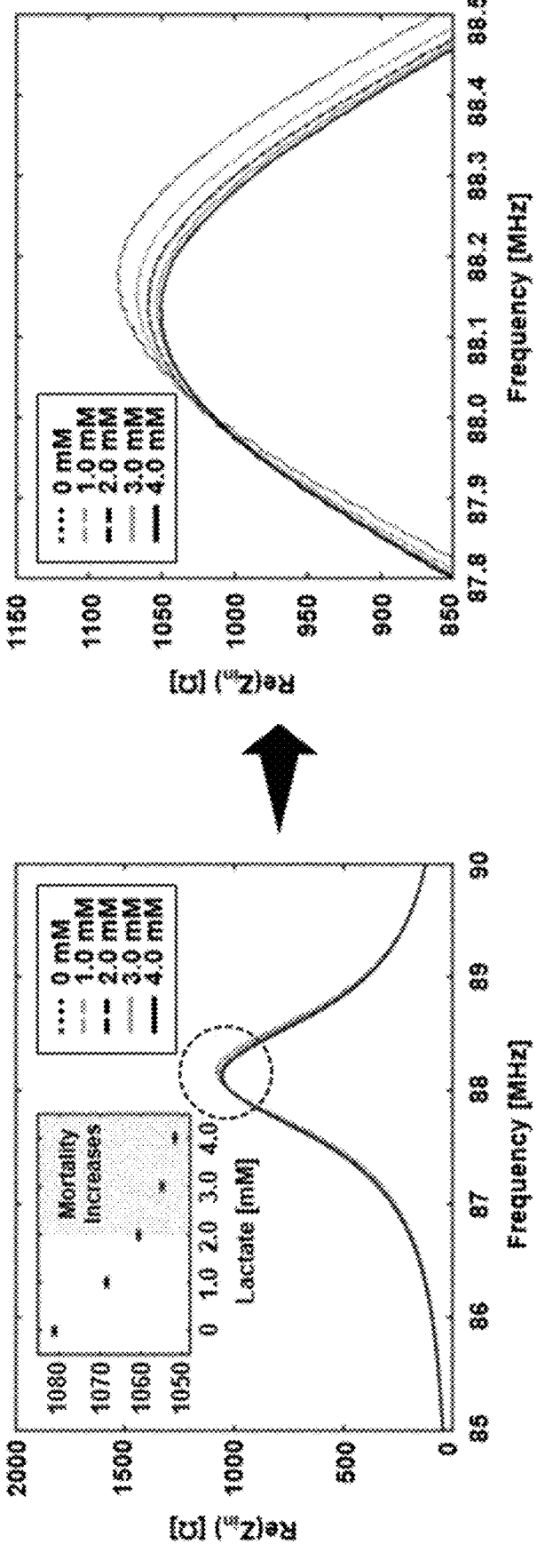
FIG. 42 shows measurement results (average values of five frequency sweeps) when the lactate concentration in PBS was changed from 0 to 4.0 (mM).

From the above results, it was found that the oxidation current tends to increase as the concentration of lactate changes. FIG. 42 is the input impedance real part component ($\text{Re}(Z_{in})$) of the lactate sensor. FIG. 42 shows measurement results (average values of five frequency sweeps) when the lactate concentration in PBS was changed from 0 to 4.0 (mM). The upper (right) diagram of FIG. 42 is an enlarged view of the vicinity of the peak (dotted circle frame portion) of the impedance real part component ($\text{Re}(Z_{in})$) in the lower (left) diagram of FIG. 42. FIG. 42 also shows the results of plotting $\text{Re}(Z_{in})$ at resonance at each concentration as an inset (average value and standard deviation for five frequency sweeps). Here, the average value of $\text{Re}(Z_{in})$ with each concentration change was as follows.

1081 (Ω): 0 (mM), 1068 (Ω): 1.0 (mM), 1061 (Ω): 2.0 (mM), 1055 (Ω): 3.0 (mM), 1052 (Ω): 4.0 (mM)

From this result, it can be said that the produced lactate sensor achieves amplitude modulation (AM) by changing the lactate concentration. Regarding sepsis using blood lactate as a biomarker, there is a report that the fatality rate of patients increases when the threshold (2.0 mM) is exceeded.

Figure 43:
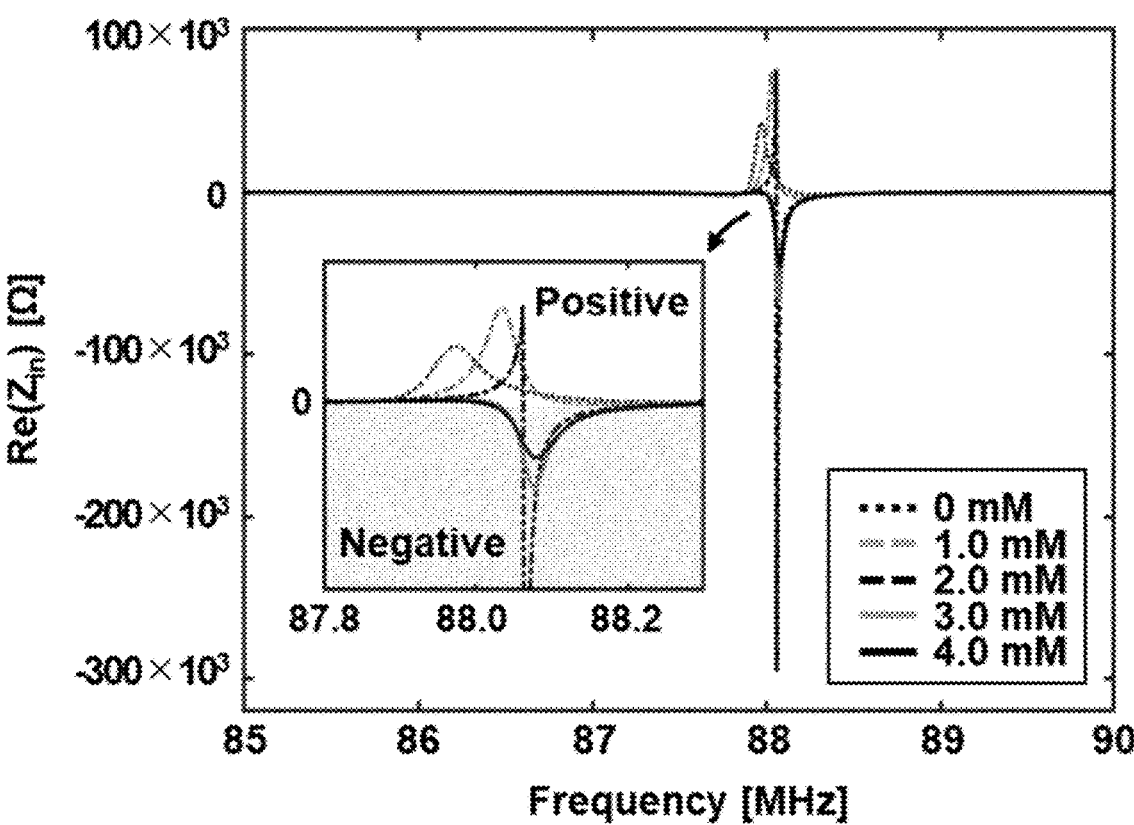
FIG. 43 is a diagram showing that the real part of the impedance is inverted with a threshold as a boundary.

Therefore, by applying a threshold discrimination system using PT symmetry, 2.0 (mM) blood lactate can be wirelessly measured. In order to observe a threshold-type response, a distance between the gain resonator and the lactate sensor was adjusted such that the reflection coefficient was OPEN ($\text{Re}(Z_{in})$=∞) when the lactate concentration was 2.0 (mM). By using the present system, the sign of the impedance real part ($\text{Re}(Z_{in})$) is inverted with the threshold (2.0 mM) as a boundary in the process of changing the lactate concentration from 0 to 4.0 (mM). FIG. 43 is a diagram showing that the sign of the real part of the impedance is inverted with a threshold as a boundary.

Figure 44:
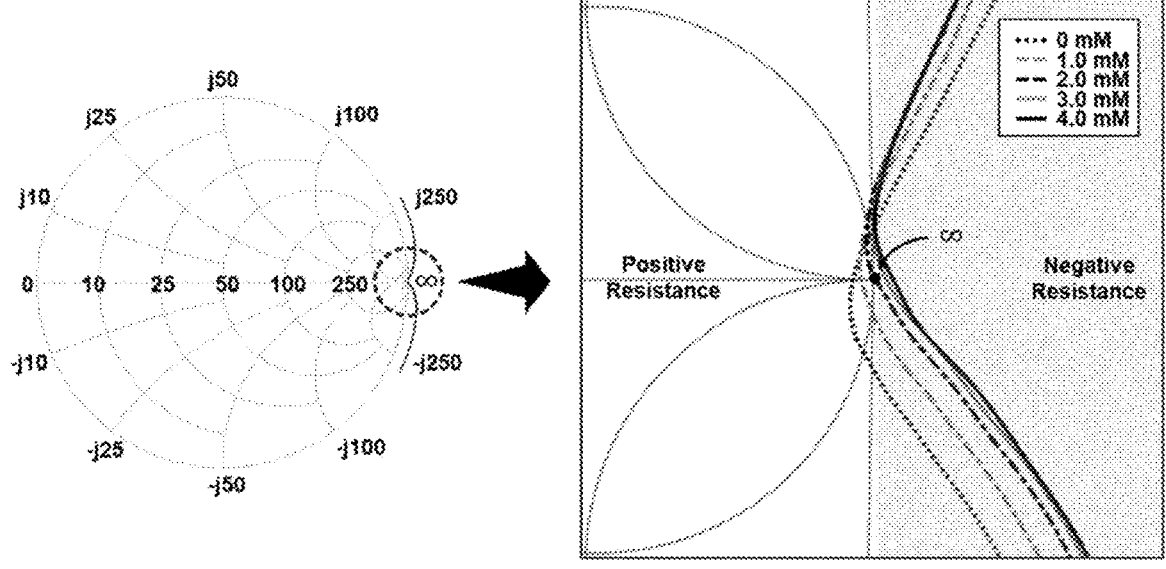
FIG. 44 is a diagram showing this phenomenon on a Smith chart.

FIG. 44 shows this phenomenon on a Smith chart, and the right diagram of FIG. 44 shows an enlarged view of the vicinity of OPEN ($\text{Re}(Z_{in})$=∞) (dotted circle frame portion of the left diagram of FIG. 44). From this drawing, it can be seen that the trajectory of the reflection coefficient shifts to the upper right as the lactate concentration increases. Here, when OPEN ($\text{Re}(Z_{in})$=∞) is used as a reference, positive $\text{Re}(Z_{in})$ is observed inside the left circle, and negative $\text{Re}(Z_{in})$ is observed outside the right circle. Therefore, it can be seen that the reflection coefficient of the present system exhibits a behavior of inverting the polarity sign while passing through the EP.

By utilizing this mechanism, a magnetic resonant coupling system can be constructed that exhibits positive $\text{Re}(Z_{in})$ when the lactate concentration is in the range of 0 to 2.0 (mM), and negative $\text{Re}(Z_{in})$ when the lactate concentration is in the range of 2.0 to 4.0 (mM). Since this exhibits the characteristic of switching the sign according to a weak resistance change on the sensor side, it can be applied to biodevices for sepsis detection in medical institutions.

(Formula and Derivation Process Thereof)

The formulas used in the above description and the derivation process thereof are shown below. Each formula is followed by a number indicating the formula, such as "(2)", in parentheses.

From FIG. 2, the relationship between voltage and current is derived.

$$\begin{pmatrix} V_1 \\ V_2 \end{pmatrix} = j\omega \begin{pmatrix} L_1 & M \\ M & L_2 \end{pmatrix}\begin{pmatrix} I_{L1} \\ I_{L2} \end{pmatrix} \tag{1B}$$

A matrix conversion is performed on the current.

$$\begin{pmatrix} I_{L1} \\ I_{L2} \end{pmatrix} = \frac{j\omega}{-\omega^2 L_1 L_2 + \omega^2 M^2}\begin{pmatrix} L_2 & -M \\ -M & L_1 \end{pmatrix}\begin{pmatrix} V_1 \\ V_2 \end{pmatrix} \tag{2}$$

Each resonant circuit is formulated by Kirchhoff's current law.

$$\begin{cases} I_{L1} + \dfrac{V_1}{R_1} + j\omega C_1 V_1 = 0 \\ I_{L2} + \dfrac{V_2}{R_2} + j\omega C_2 V_2 = 0 \end{cases} \tag{3}$$

The above Formula (2) is substituted into the above Formula (3).

$$\begin{cases} \dfrac{1}{j\omega L_1 L_2 - j\omega M^2}(L_2 V_1 - MV_2) + \dfrac{V_1}{R_1} + j\omega C_1 V_1 = 0 \\ \dfrac{1}{j\omega L_1 L_2 - j\omega M^2}(-MV_1 + L_1 V_2) + \dfrac{V_2}{R_2} + j\omega C_2 V_2 = 0 \end{cases} \quad (4)$$

$$\begin{pmatrix} j\omega C_1 + \dfrac{1}{R_1} - \dfrac{L_2}{j\omega(M^2 - L_1 L_2)} & \dfrac{M}{j\omega(M^2 - L_1 L_2)} \\ \dfrac{M}{j\omega(M^2 - L_1 L_2)} & j\omega C_2 + \dfrac{1}{R_2} - \dfrac{L_1}{j\omega(M^2 - L_1 L_2)} \end{pmatrix} \begin{pmatrix} V_1 \\ V_2 \end{pmatrix} = 0 \quad (5)$$

Here, the energy $|a_n|^2$ of the charge stored in the capacitor is used to express the voltage $V_n$.

At this time, $|a_n|^2$ means power, and an means amplitude value.

$$a_n = \sqrt{\dfrac{C_n}{2}} V_n \quad (6)$$

$$V_n = a_n \sqrt{\dfrac{2}{C_n}}$$

The resonance frequency of each resonant circuit is as follows.

$$\omega_n = \dfrac{1}{\sqrt{L_n C_n}} \quad (7)$$

The gain-loss rate of each resonant circuit is expressed by the following formula.

$$\gamma_n = \dfrac{1}{2 R_n C_n} \quad (8)$$

The coupling coefficient k between resonant circuits is as follows.

$$k = \dfrac{m}{\sqrt{L_1 L_2}} \quad (9)$$

$$k^2 L_1 L_2 = M^2$$

The above Formulas (6) to (9) are substituted into the above Formula (5).

$$\left( j\omega C_1 + \dfrac{1}{R_1} - \dfrac{L_2}{j\omega(M^2 - L_1 L_2)} \right) V_1 + \left( \dfrac{M}{j\omega(M^2 - L_1 L_2)} \right) V_2 = 0 \quad (10)$$

$$\left\{ j\omega \left( C_1 - \dfrac{L_2}{-\omega^2(M^2 - L_1 L_2)} \right) + \dfrac{1}{R_1} \right\} \sqrt{\dfrac{2}{C_1}} a_1 +$$

$$j \left( \dfrac{M}{-\omega(M^2 - L_1 L_2)} \right) \sqrt{\dfrac{2}{C_2}} a_2 = 0$$

$$\left\{ j\omega \left( C_1 - \dfrac{L_2}{-\omega^2(M^2 - L_1 L_2)} \right) + 2\gamma_1 C_1 \right\} a_1 +$$

-continued $$j \left( \dfrac{M}{-\omega(M^2 - L_1 L_2)} \right) \sqrt{\dfrac{C_1}{C_2}} a_2 = 0$$

$$\left\{ \dfrac{j\omega}{2} \left( 1 - \dfrac{L_2}{-\omega^2(M^2 - L_1 L_2)C_1} \right) + \gamma_1 \right\} a_1 +$$

$$j \left( \dfrac{M\sqrt{C_1}}{-\omega(M^2 - L_1 L_2)\sqrt{C_2}} \right) \dfrac{1}{2C_1} a_2 = 0$$

$$\left\{ \dfrac{j\omega}{2} \left( 1 - \dfrac{L_2}{-\omega^2 L_1 L_2(k^2 - 1)C_1} \right) + \gamma_1 \right\} a_1 +$$

$$j \left( \dfrac{k\sqrt{L_1 L_2}\sqrt{C_1}}{-\omega L_1 L_2(k^2 - 1)\sqrt{C_2}} \right) \dfrac{1}{2C_1} a_2 = 0$$

$$\left\{ \dfrac{j\omega}{2} \left( 1 - \dfrac{\omega_1^2}{-\omega^2(k^2 - 1)} \right) + \gamma_1 \right\} a_1 + j \left( \dfrac{k\omega_1\omega_2}{-2\omega(k^2 - 1)} \right) a_2 = 0$$

$$\left\{ \dfrac{j\omega}{2} \left( -1 + \dfrac{\omega_1^2}{-\omega^2(k^2 + 1)} \right) - \gamma_1 \right\} a_1 + j \left( \dfrac{k\omega_1\omega_2}{2\omega(-k^2 + 1)} \right) a_2 = 0$$

$$\left( \dfrac{M}{j\omega(M^2 - L_1 L_2)} \right) V_1 + \left( j\omega C_2 + \dfrac{1}{R_2} - \dfrac{L_1}{j\omega(M^2 - L_1 L_2)} \right) V_2 = 0 \quad (11)$$

$$i \left( \dfrac{M}{j\omega(M^2 - L_1 L_2)} \right) \sqrt{\dfrac{2}{C_1}} a_1 +$$

$$\left\{ j\omega \left( C_2 - \dfrac{L_1}{-\omega^2(M^2 - L_1 L_2)} \right) + \dfrac{1}{R_2} \right\} \sqrt{\dfrac{2}{C_2}} a_2 = 0$$

$$i \left( \dfrac{M}{-\omega(M^2 - L_1 L_2)} \right) \sqrt{\dfrac{C_2}{C_1}} a_1 +$$

$$\left\{ j\omega \left( C_2 - \dfrac{L_1}{-\omega^2(M^2 - L_1 L_2)} \right) + 2\gamma_2 C_2 \right\} a_2 = 0$$

$$i \left( \dfrac{M\sqrt{C_2}}{-\omega(M^2 - L_1 L_2)\sqrt{C_1}} \right) \dfrac{1}{2C_2} a_1 +$$

$$\left\{ \dfrac{j\omega}{2} \left( 1 - \dfrac{L_1}{-\omega^2(M^2 - L_1 L_2)C_2} \right) + \gamma_2 \right\} a_2 = 0$$

$$i \left( \dfrac{k\sqrt{L_1 L_2}\sqrt{C_2}}{-\omega L_1 L_2(k^2 - 1)\sqrt{C_1}} \right) \dfrac{1}{2C_2} a_1 +$$

$$\left\{ \dfrac{j\omega}{2} \left( 1 - \dfrac{L_1}{-\omega^2 L_1 L_2(k^2 - 1)C_2} \right) + \gamma_2 \right\} a_2 = 0$$

$$i \left( \dfrac{k\omega_1\omega_2}{-2\omega(k^2 - 1)} \right) a_1 + \left\{ \dfrac{j\omega}{2} \left( 1 - \dfrac{\omega_2^2}{-\omega^2(k^2 - 1)} \right) + \gamma_2 \right\} a_2 = 0$$

$$i \left( -\dfrac{k\omega_1\omega_2}{2\omega(-k^2 + 1)} \right) a_1 + \left\{ \dfrac{j\omega}{2} \left( -1 + \dfrac{\omega_2^2}{\omega^2(-k^2 + 1)} \right) - \gamma_2 \right\} a_2 = 0$$

From the above Formulas (10) and (11), the operator regarding the energy of the resonant coupling system is expressed by a matrix.

$$\begin{pmatrix} \dfrac{j\omega}{2} \left[ \dfrac{\omega_1^2}{\omega^2(1 - k^2)} - 1 \right] - \gamma_1 & -\dfrac{jk\omega_1\omega_2}{2\omega(1 - k^2)} \\ -\dfrac{jk\omega_1\omega_2}{2\omega(1 - k^2)} & \dfrac{j\omega}{2} \left[ \dfrac{\omega_2^2}{\omega^2(1 - k^2)} - 1 \right] - \gamma_2 \end{pmatrix} \begin{pmatrix} \alpha_1 \\ \alpha_2 \end{pmatrix} = 0$$

Here, the amplitude stored in each capacitor is represented by the following Formula (12).

$$H = \begin{pmatrix} \dfrac{j\omega}{2}\left[\dfrac{\omega_1^2}{\omega^2(1-k^2)} - 1\right] - \gamma_1 & -\dfrac{jk\omega_1\omega_2}{2\omega(1-k^2)} \\[4mm] -\dfrac{jk\omega_1\omega_2}{2\omega(1-k^2)} & \dfrac{j\omega}{2}\left[\dfrac{\omega_2^2}{\omega^2(1-k^2)} - 1\right] - \gamma_2 \end{pmatrix} \qquad (12)$$

The eigenvalues of the system are derived by solving the determinant of the above Formula (12).

$$\left\{\dfrac{j\omega}{2}\left[\dfrac{\omega_1^2}{\omega^2(1-k^2)} - 1\right] - \gamma_1\right\}\left\{\dfrac{j\omega}{2}\left[\dfrac{\omega_2^2}{\omega^2(1-k^2)} - 1\right] - \gamma_2\right\} - \qquad (13)$$

$$\left[\dfrac{jk\omega_1\omega_2}{2\omega(1-k^2)}\right]^2 = 0$$

$$\left(\dfrac{j\omega_1^2}{2\omega(1-k^2)} - \dfrac{j\omega}{2} - \gamma_1\right)\left(\dfrac{j\omega_2^2}{2\omega(1-k^2)} - \dfrac{j\omega}{2} - \gamma_2\right) + \dfrac{k^2\omega_1^2\omega_2^2}{4\omega^2(1-k^2)^2} = 0$$

$$-\dfrac{\omega_1^2\omega_2^2}{4\omega^2(1-k^2)^2} + \dfrac{\omega_1^2}{4(1-k^2)} - \dfrac{j\omega_1^2\gamma_2}{2\omega(1-k^2)} + \dfrac{\omega_2^2}{4(1-k^2)} -$$

$$\dfrac{\omega^2}{4} + \dfrac{j\omega\gamma_2}{2} - \dfrac{j\omega_2^2\gamma_1}{2\omega(1-k^2)} + \dfrac{j\omega\gamma_1}{2} + \gamma_1\gamma_2 + \dfrac{k^2\omega_1^2\omega_2^2}{4\omega^2(1-k^2)^2} = 0$$

$$\omega^4\{-(1-k^2)^2\} + \omega^3\{j2\gamma_1(1-k^2)^2 + j2\gamma_2(1-k^2)^2\} +$$

$$\omega^2\{(\omega_1^2+\omega_2^2)(1-k^2) + 4(1-k^2)^2\gamma_1\gamma_2\} +$$

$$\omega\{-j2\omega_1^2\gamma_1(1-k^2) - j2\omega_1^2\gamma_2(1-k^2)\} + (k^2\omega_1^2\omega_2^2 - \omega_1^2\omega_2^2) = 0$$

$$\omega^4\{-(1-k^2)^2\} + \omega^3\{j2(1-k^2)^2(\gamma_1+\gamma_2)\} +$$

$$\omega^2\{(\omega_1^2+\omega_2^2)(1-k^2) + 4(1-k^2)^2\gamma_1\gamma_2\} +$$

$$\omega\{-j2(\omega_2^2\gamma_1+\omega_1^2\gamma_2)(1-k^2)\} + \{\omega_1^2\omega_2^2(k^2-1)\} = 0$$

In the above Formula (13), a quartic equation is solved for the eigenvalue ω (Ferrari's solution).

The coefficient of each term is represented by a variable.

$$\begin{cases} a = -(1-k^2)^2 \\ b = j2(1-k^2)^2(r_1+\gamma_2) \\ c = (\omega_1^2+\omega_2^2)(1-k^2) + 4(1-k^2)^2\gamma_1\gamma_2 \\ d = -j2(\omega_2^2\gamma_1+\omega_1^2\gamma_2)(1-k^2) \\ e = \omega_1^2\omega_2^2(k^2-1) \end{cases} \qquad (14)$$

The above Formula (14) is substituted into the above Formula (13).

$$\omega^4 + \dfrac{b}{a}\omega^3 + \dfrac{c}{a}\omega^2 + \dfrac{d}{a}\omega + \dfrac{e}{a} = 0 \qquad (15)$$

$$\omega^4 + A\omega^3 + B\omega^2 + C\omega + D = 0$$

The coefficient of each term in the above Formula (15) is represented by a variable.

$$\begin{cases} A = \dfrac{b}{a} \\ B = \dfrac{c}{a} \\ C = \dfrac{d}{a} \\ D = \dfrac{e}{a} \end{cases} \qquad (16)$$

$$y = \omega + \dfrac{1}{4}A$$

$$\omega = y - \dfrac{1}{4}A$$

The above Formula (16) is substituted into the above Formula (15), and the cubic term is deleted.

$$\left(y-\dfrac{A}{4}\right)^4 + A\left(y-\dfrac{A}{4}\right)^3 + B\left(y-\dfrac{A}{4}\right)^2 + C\left(y-\dfrac{A}{4}\right) + D = 0 \qquad (17)$$

$$y^4 = \left(\dfrac{3}{B}A^2 - \dfrac{3}{4}A^2 + B\right)y^2 + \left(-\dfrac{1}{16}A^3 + \dfrac{3}{16}A^3 - \dfrac{1}{2}AB + C\right)y +$$

$$\left(\dfrac{1}{256}A^4 - \dfrac{1}{64}A^4 + \dfrac{1}{16}A^2B - \dfrac{1}{4}AC + D\right) = 0$$

$$y^4\left(-\dfrac{3}{8}A^2 + B\right)y^2 + \left(\dfrac{1}{8}A^3 - \dfrac{1}{2}AB + C\right)y +$$

$$\left(-\dfrac{3}{256}A^4 + \dfrac{1}{16}A^2B - \dfrac{1}{4}AC + D\right) = 0$$

The coefficient of each term of the above Formula (17) is represented by a variable.

$$\begin{cases} p = -\dfrac{3}{8}A^2 + B \\ q = \dfrac{1}{8}A^3 - \dfrac{1}{2}AB + C \\ r = -\dfrac{3}{256}A^4 + \dfrac{1}{16}A^2B - \dfrac{1}{4}AC + D \end{cases} \qquad (18)$$

The above Formula (18) is substituted into the above Formula (17).

$$y^4 + py^2 + qy + r = 0 \qquad (19)$$

$$y^4 = -py^2 - qy - r$$

By adding $ty^2 + (t^2/4)$ to both sides of the above Formula (19), a perfect square expression is created as shown in the following Formula (20).

$$y^4 + ty^2 + \dfrac{t^2}{4} = -py^2 - qy - r + ty^2 + \dfrac{t^2}{4} \qquad (20)$$

$$\left(y^2 + \dfrac{t}{2}\right)^2 = (t-p)y^2 - qy + \left(\dfrac{t^2}{4} - r\right)$$

In order to convert the quadratic equation of the above Formula (20) into a perfect square, the discriminant needs to be zero.

$$(-q)^2 - 4(t-p)\left(\frac{t^2}{4} - r\right) = 0 \tag{21}$$

$$q^2 - 4\left(\frac{t^3}{4} - rt - \frac{pt^2}{4} + pr\right) = 0$$

$$-t^3 + pt^2 + 4rt + q^2 - 4pr = 0$$

$$t^3 - pt^2 - 4rt + \left(4pr - q^2\right) = 0$$

The Cardano formula is applied to the above Formula (21).

$$\begin{cases} \alpha = -p \\ \beta = -4r \\ \gamma = 4pr - q^2 \end{cases} \tag{22}$$

The above Formula (22) is substituted into the above Formula (21).

$$t^3 + \alpha t^2 + \beta t + \gamma = 0 \tag{23}$$

$$t = s - \frac{1}{3}\alpha \tag{24}$$

The above Formula (24) is substituted into the above Formula (23), and the quadratic term is deleted.

$$\left(s - \frac{\alpha}{3}\right)^3 + \alpha\left(s - \frac{\alpha}{3}\right)^2 + \beta\left(s - \frac{\alpha}{3}\right) + \gamma = 0 \tag{25}$$

$$s^3 - 3s^2\frac{\alpha}{3} + 3s\left(\frac{\alpha}{3}\right)^2 - \left(\frac{\alpha}{3}\right)^3 + \alpha\left\{s^2 - 2s\frac{\alpha}{3} + \left(\frac{\alpha}{3}\right)^2\right\} + \beta y - \frac{\alpha\beta}{3} + \gamma = 0$$

$$s^3 + \left(\beta - \frac{\alpha^2}{3}\right)s + \left(\frac{2\alpha^3}{27} - \frac{\alpha\beta}{3} + \gamma\right) = 0$$

The coefficient of each term in the above Formula (25) is represented by a variable.

$$\begin{cases} P = \beta - \frac{\alpha^2}{3} \\ Q = \frac{2\alpha^3}{27} - \frac{\alpha\beta}{3} + \gamma \end{cases} \tag{26}$$

The above coefficients P and Q are substituted into the above Formula (25).

$$s^3 + Ps + Q = 0 \tag{26}$$

Here, s is expressed by the following formula.

$$s = u + v \tag{27}$$

The above Formula (27) is substituted into the above Formula (26).

$$s^3 + Ps + Q = 0(u+v)^3 + P(u+v) + Q = 0 \tag{28}$$

$$u^3 + v^3 + Q + (3uv + P) + (u + v) = 0$$

From the above Formula (28), $$\begin{cases} u^3 + v^3 + Q = 0 \\ 3uv + P = 0 \end{cases} \tag{29} \tag{30}$$

the above Formula (30) is transformed.

$$v = -\frac{P}{3u} \tag{31}$$

The above Formula (31) is substituted into the above Formula (29).

$$u^3 + \left(-\frac{P}{3u}\right)^3 + Q = 0 \tag{32}$$

$$u^3 - \frac{1}{u^3}\left(\frac{P}{3}\right)^3 + Q = 0$$

$$\frac{u^6 - \left(\frac{P}{3}\right)^2}{u^3} + Q = 0$$

$$u^6 + QU^3 - \left(\frac{P}{3}\right)^3 = 0$$

$$\left(u^3\right)^2 + Qu^3 - \left(\frac{P}{3}\right)^2 = 0$$

The quadratic solution formula is applied to the above Formula (32).

$$u^3 = \frac{-Q \pm \sqrt{Q^2 + 4\left(\frac{P}{3}\right)^3}}{2} \tag{33}$$

$$= -\frac{Q}{2} \pm \sqrt{\left(\frac{Q}{2}\right)^2 + \left(\frac{P}{3}\right)^3}$$

From the above formula (33), the cube root is derived and plus is added.

$$u = \sqrt[3]{u^3} = \sqrt[3]{-\frac{Q}{2} + \sqrt{\left(\frac{Q}{2}\right)^2 + \left(\frac{P}{3}\right)^3}} \tag{34}$$

Similarly, the above Formula (30) is transformed.

$$u = -\frac{P}{3v} \tag{35}$$

The above Formula (35) is substituted into the above Formula (29).

$$v^3 + \left(-\frac{P}{3v}\right)^3 + Q = 0 \qquad (36)$$

$$v - \frac{1}{v^3}\left(\frac{P}{3}\right)^3 + Q = 0$$

$$\frac{v^6 - \left(\frac{P}{3}\right)^3}{v^3} + Q = 0$$

$$v^6 + Qv^3 - \left(\frac{P}{3}\right)^3 = 0$$

$$\left(v^3\right)^2 + Qv^3 - \left(\frac{P}{3}\right)^3 = 0$$

The quadratic solution formula is applied to the above Formula (36).

$$v^3 = \frac{-Q \pm \sqrt{Q^2 + 4\left(\frac{P}{3}\right)^2}}{2} \qquad (37)$$

$$= -\frac{Q}{2} \pm \sqrt{\left(\frac{Q}{2}\right)^2 + \left(\frac{P}{3}\right)^3}$$

From the above Formula (37), the cube root is derived and minus is added.

$$v = \sqrt[3]{v^3} = \sqrt[3]{-\frac{Q}{2} - \sqrt{\left(\frac{Q}{2}\right)^2 + \left(\frac{P}{3}\right)^3}} \qquad (38)$$

The above Formulas (34) and (38) are substituted into the above Formula (27).

$$s = u + v$$

$$= \sqrt[3]{-\frac{Q}{2} + \sqrt{\left(\frac{Q}{2}\right)^2 + \left(\frac{P}{3}\right)^3}} + \sqrt[3]{-\frac{Q}{2} - \sqrt{\left(\frac{Q}{2}\right)^2 + \left(\frac{P}{3}\right)^3}}$$

The above Formulas are substituted into the above Formula (24).

$$t = s - \frac{1}{3}\alpha \qquad (39)$$

$$= \sqrt[3]{-\frac{Q}{2} + \sqrt{\left(\frac{Q}{2}\right)^2 + \left(\frac{P}{3}\right)^3}} + \sqrt[3]{-\frac{Q}{2} - \sqrt{\left(\frac{Q}{2}\right)^2 + \left(\frac{P}{3}\right)^3}}$$

The above Formula (20) is transformed.

$$\left(y^2 + \frac{t}{2}\right)^2 = (t-p)y^2 - qy + \left(\frac{t^2}{4} - r\right) \qquad (40)$$

$$= (t-p)\left(y^3 - \frac{qy}{t-p} + \frac{\frac{t^2}{4} - r}{t-p}\right)$$

$$= (t-p)\left[\left(y - \frac{q}{2(t-p)}\right)^2 - \left(\frac{q}{2(t-p)}\right)^2 + \frac{\frac{t^2}{4} - r}{t-p}\right]$$

$$= (t-p)\left(y - \frac{q}{2(t-p)}\right)^2 - \frac{q^2}{4(t-p)} + \frac{t^2}{4} - r$$

-continued $$= (t-p)\left(y - \frac{q}{2(t-p)}\right)^2 -$$

$$\frac{1}{4(t-p)}\left[q^2 - t^2(t-p) + 4r(t-p)\right]$$

$$= (t-p)\left(y - \frac{q}{2(t-p)}\right)^2 - \frac{1}{4(t-p)}$$

$$\frac{1}{4(t-p)}\left[q^2 - 4(t-p)\left(\frac{t^2}{4} - r\right)\right]$$

The following formula is obtained from the above Formula (21).

$$(-q)^2 - 4(t-p)\left(\frac{t^2}{4} - r\right) = 0 \qquad (41)$$

The above Formula (21) is substituted into the above Formula (40).

$$\left(y^2 + \frac{t}{2}\right)^2 = (t-p)\left(y - \frac{q}{2(t-p)}\right)^2 \qquad (42)$$

$$= (\sqrt{t-p})^2\left(y - \frac{q}{2(t-p)}\right)^2$$

$$= (\sqrt{t-p})^2\left(y - \frac{q}{2(t-p)}\right)^2$$

$$= \left[\sqrt{t-p}\left(y - \frac{q}{2(t-p)}\right)\right]^2$$

$$= \left(\sqrt{t-p} \cdot y - \frac{q}{2\sqrt{t-p}}\right)^2$$

$$\begin{cases} m = \sqrt{t-p} \\ n = -\frac{q}{2\sqrt{t-p}} \end{cases} \qquad (43)$$

The above Formula (43) is substituted into the above Formula (42).

$$\left(y^2 + \frac{t}{2}\right)^2 = (my + n)^2 \qquad (44)$$

$$\left(y^2 + \frac{t}{2}\right)^2 - (my + n)^2 = 0$$

$$\left(y^2 + my + \frac{t}{2} + n\right)\left(y^2 - my + \frac{t}{2} - n\right) = 0$$

The quadratic solution formula is applied to the above Formula (44).

$$\begin{cases} y_{1,2} = \dfrac{-m \pm \sqrt{m^2 - 4\left(\frac{t}{2} + n\right)}}{2} \\ \\ y_{3,4} = \dfrac{m \pm \sqrt{m^2 - 4\left(\frac{t}{2} - n\right)}}{2} \end{cases} \qquad (45)$$

The above Formula (45) is substituted into the above Formula (16).

$$\begin{cases} \omega_{1,2} = \dfrac{-m \pm \sqrt{m^2 - 4\left(\dfrac{t}{2} + n\right)}}{2} - \dfrac{A}{4} \\[4mm] \omega_{3,4} = \dfrac{m \pm \sqrt{m^2 - 4\left(\dfrac{t}{2} - n\right)}}{2} - \dfrac{A}{4} \end{cases} \tag{46}$$

Figure 5:
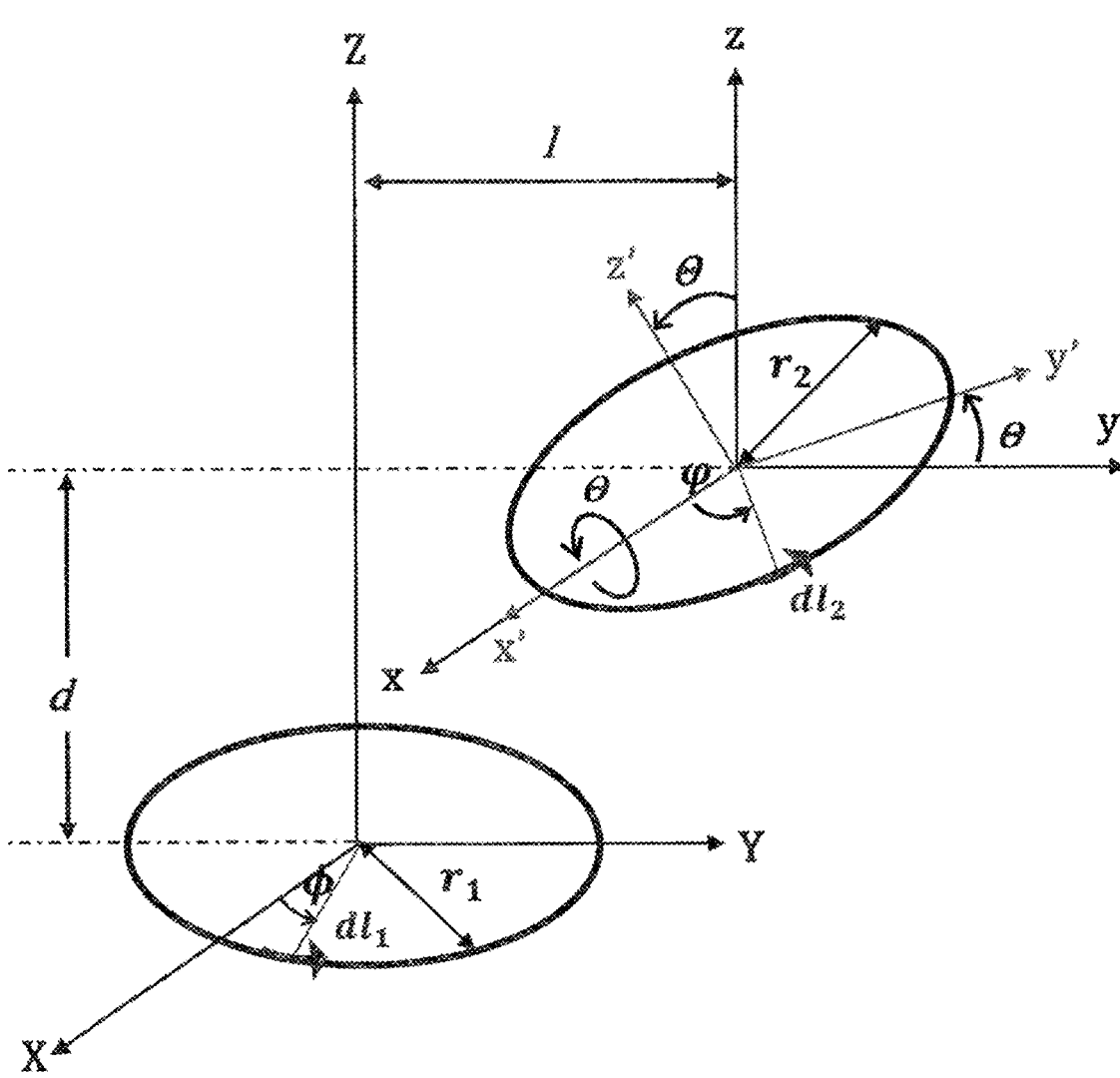
FIG. 5 is a diagram showing a resonant circuit model located on three-dimensional coordinates.

From FIG. 5, the coupling coefficient generated between two resonant circuits located on the three-dimensional coordinates is represented by the following formula.

$$k = a_1 \cdot \oint_{l_1} \oint_{l_2} \frac{a_2 + a_3 \cos\theta}{\sqrt{a_4 + a_5 \cos\theta + a_6 \sin\theta}} d\phi d\varphi \tag{47}$$

$$\begin{cases} a_1 = \dfrac{N_1 N_2 \mu_0}{4\pi\sqrt{L_1 L_2}} \\[2mm] a_2 = r_1 r_2 \sin\phi \sin\varphi \\ a_3 = r_1 r_2 \cos\phi \cos\varphi \\ a_4 = r_1^2 + r_2^2 + d^2 + l^2 - 2r_1 l \sin\phi - 2r_1 r_2 \cos\phi \cos\varphi \\ a_5 = 2r_2 l \sin\varphi - 2r_1 r_2 \sin\phi \sin\varphi \\ a_6 = 2r_2 d \sin\varphi \end{cases} \tag{48}$$

Figure 11:
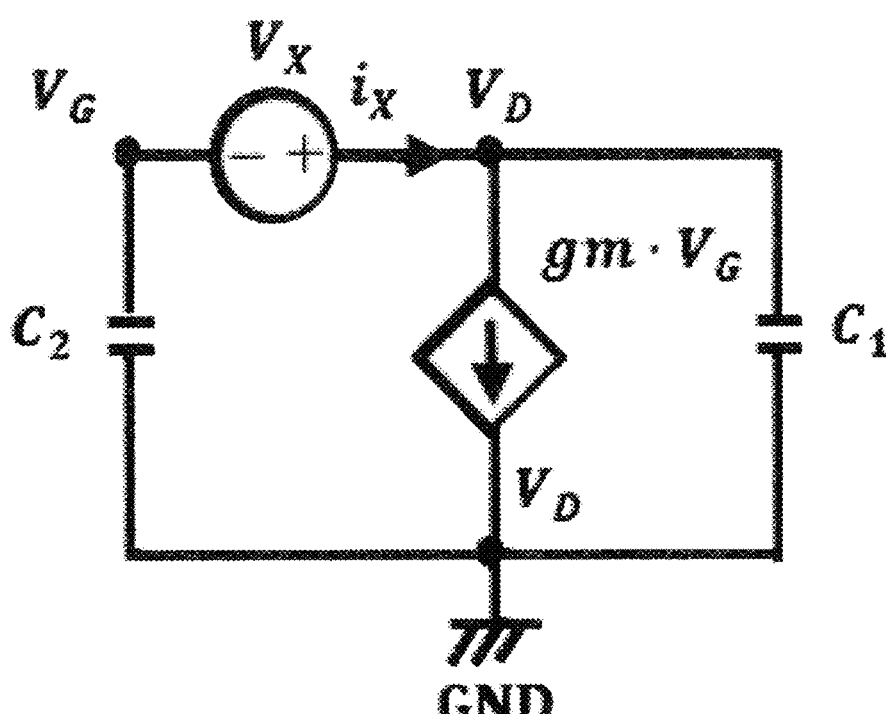
FIG. 11 is an equivalent circuit diagram of an FET and an oscillation capacitor.

From FIG. 11, the following formula is derived from the relationship between voltage and current.

$$\begin{cases} i_X = gm \cdot V_C + \dfrac{V_D}{\left(\dfrac{1}{j\omega C_1}\right)} \\[4mm] V_G = -i_x \cdot \dfrac{1}{1\omega C_2} \\[2mm] V_D = V_G + V_X \end{cases} \tag{49}$$

The following Formula (50) is derived from the above Formula (49).

$$i_X = -gm \cdot i_X \cdot \frac{1}{j\omega C_2} + \frac{-i_X \cdot \dfrac{1}{j\omega C_2} + V_X}{\left(\dfrac{1}{j\omega C_1}\right)} \tag{50}$$

$$i_X \left\{ 1 + gm \cdot \frac{1}{j\omega C_2} + \frac{\left(\dfrac{1}{j\omega C_2}\right)}{\left(\dfrac{1}{j\omega C_1}\right)} \right\} = \frac{V_X}{\left(\dfrac{1}{j\omega C_1}\right)}$$

$$\frac{1}{j\omega C_1} + \frac{1}{j\omega C_2} + gm \cdot \frac{1}{j\omega C_2} \cdot \frac{1}{j\omega C_2} = \frac{V_X}{\left(\dfrac{1}{j\omega C_1}\right)}$$

$$\left(\frac{1}{j\omega C_1} + \frac{1}{j\omega C_2}\right) - \frac{gm}{\omega^2 C_1 C_2} = Z_{in}$$

From the above Formula (50), the real part and imaginary part of the impedance are defined as follows.

$$\begin{cases} R_{series} = \dfrac{gm}{\omega^2 C_1 C_2} \\[4mm] C_o = \dfrac{1}{\left(\dfrac{1}{C_1} + \dfrac{1}{C_2}\right)} \end{cases} \tag{51}$$

From FIG. 12, the composite capacitor for the Clapp oscillation circuit is defined as follows.

$$C_{series} = \frac{1}{\left(\dfrac{1}{C_1} + \dfrac{1}{C_2} + \dfrac{1}{C_3}\right)} \tag{52}$$

From the above Formulas (51) and (52), the series connection impedance viewed from the inductance can be expressed as follows.

$$Z = \frac{1}{j\omega C_{series}} + R_{series} \tag{53}$$

The above Formula (53) is converted into admittance form and decomposed into a real part and an imaginary part.

$$\begin{aligned} Y &= \frac{1}{\dfrac{1}{j\omega C_{Series}} + R_{Series}} \tag{54} \\[4mm] &= \frac{R_{Series}}{(R_{Series})^2 + \left(\dfrac{1}{\omega C_{Series}}\right)^2} + \frac{j\dfrac{1}{\omega C_{Series}}}{(R_{Series})^2 + \left(\dfrac{1}{\omega C_{Series}}\right)^2} \\[4mm] &= \frac{1}{R_{Series}\left\{1 + \left(\dfrac{1}{\omega R_{Series} C_{Series}}\right)^2\right\}} + \\[4mm] & \quad \frac{1}{j\omega C_{Series}\left\{1 + (\omega R_{Series} C_{Series})^2\right\}} \end{aligned}$$

If Formula (54) is expressed by parallel-connected resistors R_parallel and capacitors C_parallel, it can be expressed as in Formulas (55), (56), and (57). Here, from Formula (51), it can be seen that this parallel resonant circuit exhibits a negative resistance because R_Series takes a negative value.

$$Y = \frac{1}{R_{parallel}} + j\omega C_{parallel} \tag{55}$$

$$\begin{cases} R_{parallel} = R_{Series}\left\{1 + \left(\dfrac{1}{\omega R_{Series} C_{Series}}\right)^2\right\} \\[4mm] C_{parallel} = \dfrac{C_{Series}}{\left\{1 + (\omega R_{Series} C_{Series})^2\right\}} \end{cases} \tag{56}$$

$$Q = \frac{\dfrac{1}{\omega C_{series}}}{R_{series}} \tag{57}$$

INDUSTRIAL APPLICABILITY

According to the present invention, for example, it is possible to wirelessly and highly sensitively measure weak signal changes from a living body (resonant circuit characteristic changes are small; in the above example, the glucose concentration in tears was demonstrated as a model).

Since the biochemical components contained in tears contain many contaminants, an enzyme electrode having reaction selectivity is generally used. However, since the concentration of sugar content in tears is extremely low (0 to 1.0 (mM)), the current value obtained is only 5 to 25 (μA), and the resistance value is approximately 160 to 32 (kΩ).

Measurement of glucose in tears using contact lenses (publicly known technology) is classified into enzyme sensors (Non-Patent Documents 3, 4, and 5), FET-type sensors (Non-Patent Documents 6 and 7), chemical resistors (Non-Patent Document 8), and the like.

In the present invention, by producing an enzyme sensor using the present inventor's invention relating to an enzyme electrode (carbon nanotube film described in International Publication WO2012-002290), and incorporating the enzyme sensor into the resonant circuit of the present invention, highly sensitive wireless bio-sensing was successfully achieved. As a result, since it becomes possible to distinguish the sugar content in 0.05 (mM) units, it can be used for health management of patients with diabetes (the number of patients in Japan is more than 10 million). Here, the sugar content in tears of healthy subjects is reported to be 0.05 to 0.2 (mM) (0.1 to 0.3 (mM) in fasting), and the sugar content in tears of patients with diabetes is reported to be 0.15 to 0.4 (mM) (0.15 to 0.6 (mM) in fasting) (Non-Patent Document 9).

By applying the present invention, for example, it is expected that the risk of inducing complications such as diabetic retinopathy (which is the second leading cause of blindness in Japan) can be shown as numerical data.

This application claims priority on the basis of Japanese Patent Application No. 2021-047975 filed on Mar. 22, 2021, the entire disclosure of which is incorporated herein by reference. Although the embodiments and examples of the present invention have been described above, these are examples of the present invention, and various configurations other than those described above can also be employed.

REFERENCE SIGNS LIST

10 Reader side resonant circuit
11 Coil portion
12 Capacitor portion
13 Resistance portion
20 Sensor side resonant circuit
21 Coil portion
22 Capacitor portion
23 Resistance portion (sensor element whose resistance value changes according to object to be sensed)
30 Device that measures frequency characteristics of connected devices

The invention claimed is:

1. A sensor system comprising a reader side resonant circuit and a sensor side resonant circuit, wherein
the reader side resonant circuit is an LCR parallel resonant circuit and a gain circuit,
the sensor side resonant circuit is an LCR parallel resonant circuit and a loss circuit having, as a first resistance portion, a sensor element having a first resistance that changes according to a target object to be sensed,
the reader side resonant circuit and the sensor side resonant circuit are wirelessly connected to each other through magnetic field resonant coupling to constitute a gain-loss coupling circuit, and
the reader side resonant circuit and the sensor side resonant circuit are formed so that the gain-loss coupling circuit has parity-time symmetry.

2. The sensor system according to claim 1, wherein
the sensor side resonant circuit includes a first inductance portion having a first inductance, a first capacitance portion having a first capacitance, and the first resistance portion,
at least one of a second resistance of a second resistance portion in the reader side resonant circuit, a second inductance of a second coil portion in the reader side resonant circuit, and a second capacitance of a second capacitor portion in the reader side resonant circuit is variable, and
at least one of the second resistance, the second inductance, and the second capacitance in the reader side resonant circuit is adjusted based on the first resistance that changes according to the target object to be sensed to maintain the parity-time symmetry.

3. The sensor system according to claim 1, wherein the first resistance changes according to a chemical reaction with the target object to be sensed or a physical quantity received from the target object to be sensed.

4. The sensor system according to claim 1, wherein the target object to be sensed is a substance contained in a fluid, and the fluid is one or more fluids selected from the group consisting of tears, saliva, sweat, urine, feces, exhaled breath, blood, lymph, interstitial fluid, cell fluid, tissue fluid, organ fluid, and other body fluids.

5. The sensor system according to claim 1, wherein the target object to be sensed includes at least one of glucose, lactate, urea, sodium, potassium, calcium, magnesium, chlorine, cortisol, catechol, exosomes, matrix metalloproteinase, procalcitonin, and ferritin.

6. The sensor system according to claim 1, wherein the sensor side resonant circuit is adapted to be located over a surface of or inside an object.

7. The sensor system according to claim 6, wherein the sensor side resonant circuit is located over a contact lens.

8. The sensor system according to claim 6, wherein the sensor side resonant circuit is adapted to be located inside a body.

9. The sensor system according to claim 1, further comprising
a contact lens, wherein
the sensor side resonant circuit is located over the contact lens or inside the contact lens, and
the sensor side resonant circuit comprises a coil portion, a number of turns of the coil portion in the sensor side resonant circuit being one.

10. The sensor system according to claim 1, wherein
the sensor element includes at least one of an enzyme-modified fiber, an enzyme electrode, a chemical resistor, a cell-type sensor using a working electrode, and an FET-type sensor using a graphene surface modified with an enzyme as a channel.

11. A reader used in a sensor system including a reader side resonant circuit and a sensor side resonant circuit, the reader comprising the reader side resonant circuit, wherein
the reader side resonant circuit is an LCR parallel resonant circuit and a gain circuit,
the sensor side resonant circuit is an LCR parallel resonant circuit and a loss circuit having, as a first resistance portion, a sensor element having a first resistance that changes according to a target object to be sensed,
the reader side resonant circuit and the sensor side resonant circuit are wirelessly connected to each other through magnetic field resonant coupling to constitute a gain-loss coupling circuit, and
the reader side resonant circuit and the sensor side resonant circuit are formed so that the gain-loss coupling circuit has parity-time symmetry.

12. The reader according to claim 11, wherein
the sensor side resonant circuit includes a first inductance portion having a first inductance, a first capacitance portion having a first capacitance, and the first resistance portion, at least one of a second resistance of a second resistance portion in the reader side resonant circuit, a second inductance of a coil portion in the reader side resonant circuit, and a second capacitance of a second capacitor portion in the reader side resonant circuit is variable, and at least one of the second resistance, the second inductance, and the second capacitance in the reader side resonant circuit is adjusted based on the first resistance that changes according to the target object to be sensed to maintain the parity-time symmetry.

13. The reader according to claim 11, wherein the first resistance changes according to a chemical reaction with the target object to be sensed or a physical quantity received from the target object to be sensed.

14. The reader according to claim 11, wherein the target object to be sensed is a substance contained in a fluid, and the fluid is one or more fluids selected from the group consisting of tears, saliva, sweat, urine, feces, exhaled breath, blood, lymph, interstitial fluid, cell fluid, tissue fluid, organ fluid, and other body fluids.

15. The reader according to claim 11, wherein the target object to be sensed includes at least one of glucose, lactate, urea, sodium, potassium, calcium, magnesium, chlorine, cortisol, catechol, exosomes, matrix metalloproteinase, procalcitonin, and ferritin.

16. The reader according to claim 11, wherein the sensor side resonant circuit is adapted to be located over a surface of or inside an object.

17. The reader according to claim 16, wherein the sensor side resonant circuit is located over a contact lens.

18. The reader according to claim 16, wherein the sensor side resonant circuit is adapted to be located inside a body.

19. A sensor used in a sensor system including a reader side resonant circuit and a sensor side resonant circuit, the sensor comprising the sensor side resonant circuit, wherein the reader side resonant circuit is an LCR parallel resonant circuit and a gain circuit, the sensor side resonant circuit is an LCR parallel resonant circuit and a loss circuit having, as a first resistance portion, a sensor element having a first resistance that changes according to a target object to be sensed, the reader side resonant circuit and the sensor side resonant circuit are wirelessly connected to each other through magnetic field resonant coupling to constitute a gain-loss coupling circuit, and the reader side resonant circuit and the sensor side resonant circuit are formed such-so that the gain-loss coupling circuit has parity-time symmetry.

20. The sensor according to claim 19, wherein the sensor side resonant circuit includes a first inductance portion having a first inductance, a first capacitance portion having a first capacitance, and the first resistance portion, at least one of a second resistance of a second resistance portion in the reader side resonant circuit, a second inductance of a coil portion in the reader side resonant circuit, and a second capacitance of a second capacitor portion in the reader side resonant circuit is variable, and at least one of the second resistance, the second inductance, and the second capacitance in the reader side resonant circuit is adjusted based on the first resistance that changes according to the target object to be sensed to maintain the parity-time symmetry.

21. The sensor according to claim 19, wherein the first resistance changes according to a chemical reaction with the target object to be sensed or a physical quantity received from the target object to be sensed.

22. The sensor according to claim 19, wherein the target object to be sensed is a substance contained in a fluid, and the fluid is one or more fluids selected from the group consisting of tears, saliva, sweat, urine, feces, exhaled breath, blood, lymph, interstitial fluid, cell fluid, tissue fluid, organ fluid, and other body fluids.

23. The sensor according to claim 19, wherein the target object to be sensed includes at least one of glucose, lactate, urea, sodium, potassium, calcium, magnesium, chlorine, cortisol, catechol, exosomes, matrix metalloproteinase, procalcitonin, and ferritin.

24. The sensor according to claim 19, wherein the sensor side resonant circuit is adapted to be located over a surface of or inside an object.

25. The sensor according to claim 24, wherein the sensor side resonant circuit is located over a contact lens.

26. The sensor according to claim 24, wherein the sensor side resonant circuit is adapted to be located inside a body.

27. The sensor system according to claim 3, wherein the physical quantity received from the target object to be sensed includes at least one of heat, light, current, voltage, electric field, magnetic field, speed, vibration, force including pressure, and shape change including strain.

28. The reader according to claim 13, wherein the physical quantity received from the target object to be sensed includes at least one of heat, light, current, voltage, electric field, magnetic field, speed, vibration, force including pressure, and shape change including strain.

29. The sensor according to claim 21, wherein the physical quantity received from the target object to be sensed includes at least one of heat, light, current, voltage, electric field, magnetic field, speed, vibration, force including pressure, and shape change including strain.

* * * * *